US009408816B2

(12) United States Patent
Adimoolam et al.

(10) Patent No.: US 9,408,816 B2
(45) Date of Patent: Aug. 9, 2016

(54) METHOD OF USING HISTONE DEACETYLASE INHIBITORS AND MONITORING BIOMARKERS IN COMBINATION THERAPY

(75) Inventors: Shanthi Adimoolam, Santa Clara, CA (US); Joseph J. Buggy, Mountain View, CA (US); Darren Magda, Cupertino, CA (US); Richard Miller, Portola Valley, CA (US)

(73) Assignee: Pharmacyclics LLC, Sunnyvale, CA (US)

( * ) Notice: Subject to any disclaimer, the term of this patent is extended or adjusted under 35 U.S.C. 154(b) by 1688 days.

(21) Appl. No.: 11/952,985

(22) Filed: Dec. 7, 2007

(65) Prior Publication Data

US 2008/0153877 A1  Jun. 26, 2008

Related U.S. Application Data

(60) Provisional application No. 60/871,900, filed on Dec. 26, 2006.

(51) Int. Cl.
| | |
|---|---|
| *A61K 31/4525* | (2006.01) |
| *A61K 31/164* | (2006.01) |
| *A61K 31/343* | (2006.01) |
| *A61K 31/40* | (2006.01) |

(Continued)

(52) U.S. Cl.
CPC ............ *A61K 31/164* (2013.01); *A61K 31/343* (2013.01); *A61K 31/40* (2013.01); *A61K 31/4525* (2013.01); *A61K 45/06* (2013.01)

(58) Field of Classification Search
CPC ............ A61K 2300/00; A61K 31/164; A61K 31/343; A61K 31/40; A61K 31/4525; A61K 45/06
See application file for complete search history.

(56) References Cited

U.S. PATENT DOCUMENTS

| | | | |
|---|---|---|---|
| 2,789,118 | A | 4/1957 | Bernstein et al. |
| 2,990,401 | A | 6/1961 | Bernstein et al. |

(Continued)

FOREIGN PATENT DOCUMENTS

| | | |
|---|---|---|
| CN | 1777675 A | 5/2006 |
| DE | 2201968 | 8/1973 |

(Continued)

OTHER PUBLICATIONS

Voskoglou-Nomikos et al. (Clinical Cancer Research, vol. 9, pp. 4227-4239; 2003).*

(Continued)

*Primary Examiner* — Savitha Rao
(74) *Attorney, Agent, or Firm* — Foley Hoag LLP

(57) ABSTRACT

Provided herein are methods for using at least one histone deacetylase inhibitor to decrease cellular DNA repair activity, methods for monitoring the decrease of cellular DNA repair activity using at least one biomarker, methods of treating cancer by using at least one histone deacetylase inhibitor to decrease cellular DNA repair activity in combination therapy, methods of combination therapy where at least one histone deacetylase inhibitor interferes with a DNA repairing mechanism involving RAD51, methods for predicting a induction time period between a first administration of at least one histone deacetylase inhibitor and a second administration of at least one other therapeutic treatment, and pharmaceutical compositions for combination therapy.

7 Claims, 11 Drawing Sheets

(51) Int. Cl.
  *A61K 35/00* (2006.01)
  *C12Q 1/68* (2006.01)
  *A61K 45/06* (2006.01)

(56) References Cited

U.S. PATENT DOCUMENTS

| | | | |
|---|---|---|---|
| 3,048,581 | A | 8/1962 | Fried |
| 3,126,375 | A | 3/1964 | Ringold et al. |
| 3,749,712 | A | 7/1973 | Cavazza et al. |
| 3,775,656 | A | 11/1973 | Romans |
| 3,871,236 | A | 3/1975 | De La Ceirva |
| 3,928,326 | A | 12/1975 | Brattsand et al. |
| 3,929,768 | A | 12/1975 | Brattsand et al. |
| 3,996,359 | A | 12/1976 | Brattsand et al. |
| 4,498,038 | A | 2/1985 | Malueg |
| 4,871,549 | A | 10/1989 | Ueda et al. |
| 4,999,378 | A | 3/1991 | Fujii et al. |
| 5,011,692 | A | 4/1991 | Fujioka et al. |
| 5,017,381 | A | 5/1991 | Maruyama et al. |
| 5,229,135 | A | 7/1993 | Philippon et al. |
| 5,254,731 | A | 10/1993 | Zimmer et al. |
| 5,260,068 | A | 11/1993 | Chen |
| 5,260,069 | A | 11/1993 | Chen |
| 5,448,938 | A | 9/1995 | Fernandez et al. |
| 5,508,040 | A | 4/1996 | Chen |
| 5,567,441 | A | 10/1996 | Chen |
| 5,612,059 | A | 3/1997 | Cardinal et al. |
| 5,698,220 | A | 12/1997 | Cardinal et al. |
| 5,798,119 | A | 8/1998 | Herbig et al. |
| 5,837,284 | A | 11/1998 | Mehta et al. |
| 5,840,329 | A | 11/1998 | Bai |
| 5,972,978 | A | 10/1999 | Andersen et al. |
| 6,211,197 | B1 | 4/2001 | Belley et al. |
| 6,611,662 | B1 | 8/2003 | Grober |
| 6,660,744 | B1 | 12/2003 | Hirst et al. |
| 6,921,763 | B2 | 7/2005 | Hirst et al. |
| 7,247,426 | B2 | 7/2007 | Yakhini et al. |
| 7,332,497 | B2 | 2/2008 | Hirst et al. |
| 7,834,054 | B2 * | 11/2010 | Verner et al. ............... 514/469 |
| 8,603,521 | B2 | 12/2013 | Loury et al. |
| 8,779,171 | B2 | 7/2014 | Verner et al. |
| 2003/0007795 | A1 | 1/2003 | Grober |
| 2003/0166026 | A1 | 9/2003 | Goodman |
| 2004/0053908 | A1 | 3/2004 | Funahashi et al. |
| 2004/0077726 | A1 | 4/2004 | Watkins et al. |
| 2004/0132825 | A1 | 7/2004 | Bacopoulos et al. |
| 2004/0134340 | A1 | 7/2004 | Quinn |
| 2004/0198830 | A1 | 10/2004 | Watkins et al. |
| 2005/0187261 | A1 * | 8/2005 | Verner et al. ............... 514/350 |
| 2005/0272755 | A1 | 12/2005 | Denis et al. |
| 2007/0293540 | A1 | 12/2007 | Verner et al. |
| 2008/0004331 | A1 | 1/2008 | Verner et al. |
| 2008/0255214 | A1 | 10/2008 | Verner et al. |
| 2008/0255221 | A1 | 10/2008 | Verner et al. |
| 2011/0021528 | A1 | 1/2011 | Verner et al. |
| 2011/0039840 | A1 | 2/2011 | Varasi et al. |
| 2011/0065734 | A1 | 3/2011 | Bar et al. |
| 2011/0311624 | A1 | 12/2011 | Loury et al. |
| 2012/0064032 | A1 | 3/2012 | Verner et al. |
| 2013/0064880 | A1 | 3/2013 | Kloos et al. |
| 2013/0142758 | A1 | 6/2013 | Verner et al. |
| 2014/0057862 | A1 | 2/2014 | Loury et al. |
| 2014/0301976 | A1 | 10/2014 | Verner et al. |

FOREIGN PATENT DOCUMENTS

| | | |
|---|---|---|
| EP | 0084236 A2 | 7/1983 |
| EP | 0394440 A1 | 10/1990 |
| EP | 1233017 A1 | 8/2002 |
| EP | 1400806 A1 | 3/2004 |
| EP | 1426054 A1 | 6/2004 |
| EP | 1595952 A1 | 11/2005 |
| EP | 1611088 B1 | 6/2009 |
| GB | 1381319 A | 1/1975 |
| JP | 3-215470 | 9/1991 |
| JP | 2006-0522157 | 9/2006 |
| JP | 2006526031 A | 11/2006 |
| RU | 2286784 C2 | 11/2006 |
| WO | WO-95-05358 A1 | 2/1995 |
| WO | WO-00-20371 A1 | 4/2000 |
| WO | WO-01-11369 A1 | 2/2001 |
| WO | WO-01-14331 A2 | 3/2001 |
| WO | WO-01-38322 A1 | 5/2001 |
| WO | WO-02-26703 A1 | 4/2002 |
| WO | WO-02-30879 A2 | 4/2002 |
| WO | WO-02-053775 | 7/2002 |
| WO | WO-03-013493 A1 | 2/2003 |
| WO | WO-03-066892 | 8/2003 |
| WO | WO-03-070691 A1 | 8/2003 |
| WO | WO-2004-013130 A1 | 2/2004 |
| WO | WO-2004-92115 A2 | 10/2004 |
| WO | WO-2005030239 A2 | 4/2005 |
| WO | WO-2005-059108 A2 | 6/2005 |
| WO | WO-2005-097770 A1 | 10/2005 |
| WO | WO-2005105055 A1 | 11/2005 |
| WO | WO-2006-042035 | 4/2006 |
| WO | WO-2006-101454 A1 | 9/2006 |
| WO | WO-2008-082856 A1 | 7/2008 |
| WO | WO-2008-095050 | 8/2008 |
| WO | WO-2013-039488 | 3/2013 |

OTHER PUBLICATIONS

Stella (Expert Opinion on Therapeutic Patents, Prodrugs as therapeutics, vol. 14, No. 3, pp. 277-280; 2004).*
Wolff (Burger's Medicinal Chemistry, 5th Ed., vol. 1, pp. 975-977; 1994).*
Testa (Biochemical Pharmacology, Prodrug Research: futile or fertile?, vol. 68, pp. 2097-2106; 2004).*
Ettmayer et al. (Medicinal Chemistry, Lessons Learned from Marketed and Investigational Prodrugs, vol. 47, No. 10, pp. 2394-2404; 2004).*
Bolden et al. (Nature Reviews, vol. 5, pp. 769-784; Sep. 2006).*
Connell et al. (Int J Oncol, vol. 28, No. 5, Abstract; May 2006).*
Lose et al. (Breast Cancer Research, vol. 8, No. 3, pp. 1-7 of the document; 2006).*
PCT/US07/086874 Search Report dated May 22, 2008.
Supp EP Search Report for EP07869059.1 dated Apr. 26, 2010.
Adimoolam et al., "HDAC inhibitor PCI-24781 decreases RAD51 expression and inhibits homologous recombination," PNAS 104 (49):19482-19487 (2007).
Chinnaiyan et al., "Modulation of radiation response by histone deaceytlase inhibition," Int. J. Radiation Oncology Biol. Phys. 63(1):223-229 (2005).
Raderschall et al., "Elevated Levels of Rad51 Recombination Protein in Tumor Cells," J. Cancer Res. 62:219-225 (2002).
U.S. Appl. No. 13/744,65, filed Jan. 17, 2013, Verner et al.
Bristow et al., "Homologous recombination and prostate cancer: A model for novel DNA repair targets and therapies," Radiotherapy and Oncology, 2007, 11 pgs.
Brzozowski, Z. et al., "Derivatives of 2-Mercapobenzenesulphonamide XI. Synthesis and Some Pharmacological Properties of 2-{2 —[2-(3,4,5-Trimethoxybenzamido)Ethylthio]Benzenesulphonyl} Guanadines," Acta Poloniac Pharmaceutica—Drug Research 50(4-5):345-352 (1993).
Carter et al., Chemotherapy of Cancer, 2nd ed., John Wiley & Sons, N.Y., N.Y. 1981, pp. 362-365.
Delacote et al., "An xrcc4 defect or Wormannin stimulates homologous recombination specifically induced by double-strand breaks in mammalian cells," Nucleicu Acids Research, 2002, vol. 30, No. 15, pp. 3454-3463.
Hines, J.W. and Stammer, C.H., "3-Hydroxyisoxazole-5-hydroxamic Acid," J. Med. Chem 20(7):965-967 (1977).
LaVoie R., "Design and Synthesis of a Novel Class of Histone Deacetylase Inhibitors," Bioorg. Med. Chem. Ltrs. 11:2847-2850 (2001).
PCT/US2006/03341 Search Report dated Jul. 3, 2008.
PCT/US2004/010549 International Search Report dated Dec. 20, 2004.

(56) References Cited

OTHER PUBLICATIONS

PCT/US2004/010549 Written Opinion dated Oct. 7, 2005.
Pierce et al., "Ku DNA end-binding protein modulates homologous repair of double-strand breaks in mammalian cells," Genes Dev. 2001, 15:3237-3242.
Uesato, S., "Novel Histone Deacetylase Inhibitors: N-Hydroxycarboxamides Possessing a Terminal Bicyclic Aryl Group," Bioorg. Med. Chem. Ltrs. 12:1347-1349 (2002).
Watanabe, S. et al., "Synthesis of 4-[1-(substituted phenyl)-2-oxo-pyrrolidin4-yl]methyloxybenzoic acids and related compounds, and their inhibitory capacities toward fatty-acid and sterol biosynthesis," Eur. J. Med. Chem. 29:675-686 (1994).
Chinnaiyan et al., "Modulation of radiation response by histone deacetylase inhibition.," Int. J. Radiation Oncology Biol Phys., 2005, vol. 62, No. 1, p. 223-229.
Adimoolam et al., "HDAC inhibitor PCI-24781 decreases RAD51 expression and inhibits homologous recombination," PNAS, 2007, vol. 104, No. 49, p. 19482-19487.
Catalano et al., "Valproic acid, a histone deacetylase inhibitor, enhances sensitivity to doxorubicin in anaplastic thyroid cancer cells," Journal of Endocrinology. 2006, vol. 191, p. 465-472.
Buggy et al, CRA-024781: a novel synthetic inhibitor of histone deacetylase enzymes with antitumor activity in vitro and invivo, Mol Cancer Ther, 5(5):1309-1317.
U.S. Appl. No. 13/744,265 Final Action dated Oct. 23, 2013.
Bau et al. "Breast Cancer Risk and the DNA Double-Strand Break End-Joining Capacity of Nonhomologous End-Joining Genes Are Affected by BRCA1." *Cancer Research*, 2004, 64(14):5013-5019.
Belikov et al. "Farmatsevticheskaya chimiya." *M, Vysshaya shkola*, 1993, vol. 1, pp. 43-47 (Eng. Abstract included).
Deans et al. "Cyclin-Dependent Kinase 2 Functions in Normal DNA Repair and Is a Therapeutic Target in BRCA1-Deficient Cancers." *Cancer Research*, Aug. 2006, 66(16):8219-8226.
Dowdy et al. "Histone deacetylase inhibitors and paclitaxel cause synergistic effects on apoptosis and microtubule stabilization in papillary serous endometrial cancer cells". *Molecular Cancer Therapeutics*, 2006, 5(11):2767-2776.
Donovan et al. "Homotypic and Heterotypic Protein Associations Control RAD51 Function in Double-Strand Break Repair." *Genes & Development*, 1994, 8(21):2552-2562.
Maacke et al. "Over-expression of wild-type Rad51 correlates with histological grading of invasive ductal breast cancer." *International Journal of Cancer*, 2000, 88(6):907-913.
Zhang et el. "Chk2 Phosphorylation of BRCA1 Regulates DNA Double-Strand Break Repair." *Molecular & Cellular Biology*, 2004, 24(2):708-718.
Zhou et al. "Role of BRCA1 in Cellular Resistance to Paclitaxel and Ionising Radiation in an Ovarian Cancer Cell Line Carrying a Defective BRCA1." *Oncogene*, 2003, 22(16):2396-2404.
AU2007340120 Office Action mailed Apr. 20, 2010.
RU2009126655 Office Action mailed Oct. 22, 2010.
EP07869059 Office Communication mailed Feb. 3, 2011.
CN200780051772.6 Second Office Action mailed Aug. 24, 2011.
EP07869059 Office Communication mailed Nov. 28, 2011.
KR10-2009-7015579 Office Action mailed Feb. 29, 2012.
JP2009-544149 Office Action dated Feb. 6, 2012.
Catalano et al. "Valproic acid, a histone deacetylast inhibitor, enhances sensitivity to doxorubicin in anaplastic thyroid cancer cells." *Journal of Endocrinology*, 2006, 191:465-472.
Yaneva et al. "Non-homologous end joining, but not homologous recombination, enables survival for cells exposed to a histone deacetylase inhibitor." *Nucleic Acids Research*, 2005, 33(16):5320-5330.
NZ598066 Examination Report dated Feb. 8, 2012.
PCT/US2007/086874 IPRP dated Jun. 30, 2009.

Banwell, et al., "Antiproliferative signalling by 1,25(OH)2D3 in prostate and breast cancer is suppressed by a mechanism involving histone deacetylation." Recent Results Cancer Res.: 164:83-98 (2003).
De Schepper, et al. "Inhibition of Histone Deacetylases by chlamydocin Induces Apoptosis and Proteasome-Mediated Degradation of Survivin." The Journal of Pharmacology and Experimental Therapeutics, vol. 304, No. 2, pp. 881-888 (2003).
EP 131537573 Extended European search report dated Jul. 12, 2013.
EP 08728620 Supplementary Search Report mailed Aug. 24, 2010.
Hardiman, "Microarray Platforms-Comparisons and Contrasts," Pharmacogenomics 5(5):487-502 (2004).
Kelly, et al., "Histone deacetylase inhibitors: from target to clinical trials." Expert Opin Investig Drugs. Dec.;11(12):1695-713 (2002).
LePage, C. et al., "From gene profiling to diagnostic markers: IL-18 and FGF-2 complement CA125 as serum-based markers in epithelial ovarian cancer," Int. J. Cancer 118(7):1750-1758 (2006).
Mori et al., "FR235222, a fungal metabolite, is a novel immunosuppressant that inhibits mammalian histone deacetylase (HDAC). I. Taxonomy, fermentation, isolation and biological activities." J Antibiot (Tokyo). Feb.; 56(2):72-9 (2003).
Natrajan, R. et al., "Array CGH profiling of favourable histology Wilms tumours reveals novel gains and losses associated with relapse," J. Pathol. 210(1):49-58 (2006).
PCT/US08/52540 Search Report dated Jun. 17, 2008.
Piekarz et al. "T-cell lymphoma as a model for the use of histone deacetylase inhibitors in cancer therapy: impact of depsipeptide on molecular markers, therapeutic targets, and mechanisms of resistance," Blood 103(12):4636-4643 (2004).
Sasakawa et al., "Marker genes to predict sensitivity to FK 228, a histone deacetylase inhibitor," Biochem. Pharmacol. 69(4):603-616 (2005).
U.S. Appl. No. 13/744,265 Office action mailed Jun. 10, 2013.
Furumai et al. Potent histone deacetylase inhibitors built from trichostatin A and cyclic tetrapeptide antibiotics including trapoxin. PNAS. Jan. 2, 2001. 98(1):87-92.
Marks et al. Histone Deacetylase Inhibitors: Inducers of Differentiation or Apoptosis of Transformed Cells. Journal of the National Cancer Institute 92(15):1210-1216 , Aug. 2, 2000.
U.S. Appl. No. 14/069,233 Office Action mailed Jul. 22, 2014.
U.S. Appl. No. 14/311,025 Office Action mailed Sep. 30, 2014.
PCT/US2011/051470 International Search Report and Written Opinion dated Apr. 20, 2012.
U.S. Appl. No. 10/818,755 Office Action mailed Mar. 15, 2007.
U.S. Appl. No. 11/834,558 Office Action mailed Feb. 5, 2008.
U.S. Appl. No. 12/761,588 Office Action mailed Feb. 20, 2013.
U.S. Appl. No. 12/761,588 Office Action mailed Jul. 24, 2012.
U.S. Appl. No. 12/896,535 Office Action mailed Mar. 8, 2011.
U.S. Appl. No. 13/209,147 Office Action mailed Apr. 18, 2012.
U.S. Appl. No. 14/069,233 Office Action mailed Dec. 18, 2013.
Bhalla et al. PCI-24781 induces caspase and reactive oxygen species-dependent apoptosis through NF-kappB mechanisms and is synergistic with bortezomib in lymphoma cells. Clin Cancer Res 15:3354-3365 (2009).
Burma et al. Role of non-homologous end joining (NHEJ) in maintaining genomic integrity. DNA Repair 5:1042-1048 (2006).
Co-pending U.S. Appl. No. 14/671,384, filed Mar. 27, 2015.
Co-pending U.S. Appl. No. 14/620,075, filed Feb. 11, 2015.
PCT/US2011/051470 International Search Report and Written Opinion dated Sep. 13, 2011.
Tennstedt et al. RAD51 overexpression is a negative prognostic marker for colorectal adenocarcinoma. Int. J. Cancer 132:2118-2126 (2013).
U.S. Appl. No. 12/393,923 Office Action mailed Mar. 19, 2010.
Yang et al. Histone deacetylase inhibitor (HDACI) PCI-24781 potentiates cytotoxic effects of doxorubicin in bone sarcoma cells. Cancer Chemother Pharmacol. 67(2):439-46 (2011).
De Miranda et al. DNA repair genes are selectively mutated in diffuse large B cell lymphomas. J Exp Med 210(9):1729-1742 (2013).

* cited by examiner

Dose mouse orally with 3-((dimethylamino)methyl)-N-(2-(4-(hydroxycarbamoyl)phenoxy)ethyl)benzofuran-2-carboxamide

A

B

| Cell Line | RAD51 mRNA Decrease | RAD51 protein decrease | % Apoptosis |
|---|---|---|---|
| HH | 0.92 | 1.16 | 15.0 |
| DB | 1.00 | 0.39 | 23.0 |
| DHL-4 | 3.99 | 0.31 | 24.0 |
| K562 | 4.70 | 0.36 | 30.0 |
| RAJI | 10.00 | 0.42 | 41.0 |
| DLCL2 | 10.00 | 0.31 | 70.0 |
| DOHH2 | 5.21 | 0.04 | 70.0 |
| Jurkat | 3.48 | 0.28 | 71.3 |
| Ramos | 6.21 | 0.48 | 72.0 |
| SupT1 | 5.08 | 0.51 | 84.0 |

Figure 8C

METHOD OF USING HISTONE DEACETYLASE INHIBITORS AND MONITORING BIOMARKERS IN COMBINATION THERAPY

CROSS-REFERENCE TO RELATED APPLICATIONS

This application claims benefit of U.S. Provisional Application No. 60/871,900, entitled "Method of Using Histone Deacetylase Inhibitors and Monitoring Biomarkers in Combination Therapy" filed Dec. 26, 2006, which is hereby incorporated by reference.

BACKGROUND

DNA damage causes chromosomal instability, oncogensis, cell death, and severe dysfunction of cells. The DNA repair system is crucially important for the survival of living cells. The two major DNA repair mechanisms involved in the repair of double stranded DNA breaks are homologous recombination (HR) and non-homologous end-joining (NHEJ). The eukaryotic RAD51 gene is an ortholog of *Escherichia coli* RecA, and the gene product RAD51 protein plays a central role in homologous recombination.

Many therapeutic treatments, such as anti-cancer agents, exert their therapeutic effects through their capability of producing DNA damage to cells. If the cells, such as cancer cells, have active DNA repair mechanisms, the therapeutic effects of such treatments may be compromised and high dosages may be needed for achieving the desired therapeutic effects.

SUMMARY OF THE INVENTION

Described herein are methods for using at least one histone deacetylase inhibitor to decrease cellular DNA repair activity. Also described herein are methods for monitoring the decrease of cellular DNA repair activity using at least one biomarker.

Described herein are methods of treating cancer by using at least one histone deacetylase inhibitor to decrease cellular DNA repair activity in combination therapy. Described are methods of combination therapy where at least one histone deacetylase inhibitor interferes with a DNA repairing mechanism involving RAD51. Also described are methods for predicting the time period between the administration of at least one histone deacetylase inhibitor and a second administration of at least one other therapeutic treatment. Also described herein are pharmaceutical compositions for combination therapy.

In one aspect are methods for treating diseases, disorders, or conditions associated with a defect in non-homologous end joining of DNA, comprising:
(a) administering to a human patient having a disease, disorder, or condition associated with a defect in non-homologous end joining of DNA, a therapeutically effective amount of at least one agent that inhibits the activity of RAD51, disrupts the formation of RAD51 foci, or disrupts the assembly of a functional repair complex for homologous recombination of DNA; and
(b) administering to the human patient a treatment capable of damaging cellular DNA.

In another embodiment, the agent disrupts the assembly of a functional repair complex for homologous recombination of DNA. In another embodiment, the agent that inhibits the activity of RAD51 reduces cellular levels of RAD51. In another embodiment, the agent that disrupts the assembly of a functional repair complex for homologous recombination of DNA is a therapeutically effective amount of at least one histone deacetylase inhibitor, or its pharmaceutically acceptable derivative.

In another embodiment, the agent that disrupts the formation of RAD51 foci is a therapeutically effective amount of at least one histone deacetylase inhibitor, or its pharmaceutically acceptable derivative. In another embodiment, the defect in non-homologous end joining of DNA comprises a defect in a gene selected from the group consisting of: Ku70, Ku80, Ku86, Ku, PRKDC, LIG4, XRCC4, DCLRE1C, and XLF. In another embodiment, the disease, disorder, or condition is cancer. In another embodiment, the disease, disorder, or condition is selected from Burkitt's lymphoma, chronic myelogenous leukemia, and B-cell lymphoma. In another embodiment, the DNA damaging agent is administered when the expression of RAD51 is within a predetermined range. In another embodiment, the therapeutically effective amount of the at least one histone deacetylase inhibitor is from about 0.2 mg to about 2000 mg.

In another embodiment, the predetermined range of the expression level of RAD51 is less than about 70% as compared to the expression level of RAD51 before the administration of the at least one histone deacetylase inhibitor. In another embodiment, the cancer is selected from the group consisting of: breast cancer, colon cancer, colorectal carcinomas, non-small cell lung cancer, small-cell lung cancer, liver cancer, ovarian cancer, prostate cancer, uterine cervix cancer, urinary bladder cancer, gastric carcinomas, gastrointestinal stromal tumors, pancreas cancer, germ cell tumors, mast cell tumors, neuroblastoma, mastocytosis, testicular cancers, glioblastomas, astrocytomas, lymphomas, melanoma, myelomas, acute myelocytic leukemia (AML), acute lymphocytic leukemia (ALL), myelodysplastic syndrome, and chronic myelogenous leukemia.

In another embodiment, the treatment capable of damaging cellular DNA comprises radiotherapy, or administration of a pharmaceutically effective amount of at least one anticancer agent, a combination scheme for cancer therapy, or any combination thereof. In another embodiment, the treatment capable of damaging cellular DNA is radiotherapy or an administration of a pharmaceutically effective amount of at least one agent selected from the group consisting of topoisomerase inhibitors, tubulin interactors, DNA-interactive agents, DNA-alkylating agents, and platinum complexes.

In another embodiment, the treatment capable of damaging cellular DNA comprises radiotherapy. In another embodiment, the anticancer agent comprises cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, biphosphonates, or any combination thereof.

In another aspect are methods for treating cancer, comprising:
(a) administering to a human patient having cancer a therapeutically effective amount of at least one histone deacetylase inhibitor, or its pharmaceutically acceptable derivative; and
(b) administering at least one other anticancer treatment when the expression level of a predetermined biomarker is within a predetermined range.

In another embodiment, the cancer is selected from the group consisting of: breast cancer, colon cancer, colorectal carcinomas, non-small cell lung cancer, small-cell lung cancer, liver cancer, ovarian cancer, prostate cancer, uterine cervix cancer, urinary bladder cancer, gastric carcinomas, gastrointestinal stromal tumors, pancreas cancer, germ cell tumors, mast cell tumors, neuroblastoma, mastocytosis, testicular cancers, glioblastomas, astrocytomas, lymphomas, melanoma, myelomas, acute myelocytic leukemia (AML), acute lymphocytic leukemia (ALL), myelodysplastic syndrome, and chronic myelogenous leukemia.

In another embodiment, the cancer is associated with a defect in non-homologous end joining of DNA. In another embodiment, the defect in non-homologous end joining of DNA comprises a defect in a gene selected from the group consisting of: Ku70, Ku80, Ku86, Ku, PRKDC, LIG4, XRCC4, DCLRE1C, and XLF. In another embodiment, the disease, disorder, or condition is selected from Burki's lymphoma, chronic myelogenous leukemia, and B-cell lymphoma. In another embodiment, the cancer is associated with overexpression of RAD51. In another embodiment, the cancer is associated with overexpression of homologous recombination of DNA or wherein the pathogenesis of the cancer involves homologous recombination of DNA. In another embodiment, the therapeutically effective amount of the at least one histone deacetylase inhibitor is from about 0.2 mg to about 2000 mg.

In another embodiment, the therapeutically effective amount is sufficient to disrupt the assembly of a functional repair complex for homologous recombination of DNA. In another embodiment, the therapeutically effective amount is sufficient to reduce cellular levels of RAD51 in a cell. In another embodiment, the therapeutically effective amount is sufficient to disrupt the formation of RAD51 foci in a cell.

In another embodiment, the pre-determined biomarker is RAD51. In another embodiment, the pre-determined biomarker is disruption of RAD51 foci. In another embodiment, the pre-determined range of the biomarker's expression level is less than about 70% as compared to the biomarker's expression level before the administration of the at least one histone deacetylase inhibitor. In another embodiment, the at least one other anticancer treatment comprises radiotherapy, or an administration of a pharmaceutically effective amount of at least one anticancer agent, a known combination scheme for cancer therapy, or any combination thereof.

In another embodiment, the at least one other anticancer treatment comprises a treatment capable of damaging cellular DNA. In another embodiment, the treatment capable of damaging cellular DNA is radiotherapy or an administration of a pharmaceutically effective amount of at least one agent selected from the group consisting of topoisomerase inhibitors, tubulin interactors, DNA-interactive agents, DNA-alkylating agents, and platinum complexes.

In another embodiment, the at least one other anticancer treatment comprises radiotherapy. In another embodiment, the anticancer agent comprises cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, biphosphonates or any combination thereof.

In another aspect are methods for using histone deacetylase inhibitors, comprising:
(a) administering to a subject a therapeutically effective amount of at least one histone deacetylase inhibitor, or its pharmaceutically acceptable derivative;
(b) monitoring a decrease of expression level of a pre-determined biomarker in at least one cell of the subject; and (c) administering at least one other therapeutic treatment when the expression level of the biomarker is within a pre-determined range.

In another embodiment, the subject is a human patient. In another embodiment, the subject has a disease, disorder, or condition associated with a defect in non-homologous end joining of DNA. In another embodiment, the defect in non-homologous end joining of DNA comprises a defect in a gene selected from the group consisting of: Ku70, Ku80, Ku86, Ku, PRKDC, LIG4, XRCC4, DCLRE1C, and XLF.

In another embodiment, the disease, disorder, or condition is selected from Burkitt's lymphoma, chronic myelogenous leukemia, and B-cell lymphoma. In another embodiment, the subject has a disease, disorder, or condition associated with overexpression of RAD51. In another embodiment, the subject has a disease, disorder, or condition associated with overexpression of homologous recombination of DNA or wherein the pathogenesis of the disease, disorder, or condition involves homologous recombination of DNA. In another embodiment, the disease, disorder, or condition is selected from Bloom's Syndrome or viral infection. In another embodiment, the therapeutically effective amount of the at least one histone deacetylase inhibitor is from about 0.2 mg to about 2000 mg.

In another embodiment, the pre-determined biomarker is RAD51. In another embodiment, the pre-determined range of the biomarker's expression level is less than about 70% as compared to the biomarker's expression level before the administration of the at least one histone deacetylase inhibitor. In another embodiment, the at least one other therapeutic treatment is selected from the group consisting of radiotherapy, surgery, gene therapy, siRNA or RNAi therapy, an administration of a pharmaceutically effective amount of at least one anticancer agent, a known combination scheme for cancer therapy, and any combination thereof.

In another embodiment, the at least one other therapeutic treatment comprises a treatment capable of damaging cellular DNA. In another embodiment, the treatment capable of damaging cellular DNA is radiotherapy or an administration of a pharmaceutically effective amount of at least one agent selected from the group consisting of topoisomerase inhibitors, tubulin interactors, DNA-interactive agents, DNA-alkylating agents, and platinum complexes.

In another embodiment, the at least one other therapeutic treatment comprises radiotherapy. In another embodiment, the anticancer agent comprises cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, biphosphonates, or any combination thereof.

In another aspect are methods for treating diseases, disorders, or conditions associated with overexpression of RAD51, comprising:
(a) administering to a human patient having a disease, disorder, or condition associated with overexpression of RAD51 a therapeutically effective amount of at least one agent that inhibits activity of RAD51, disrupts the formation of RAD51 foci, or disrupts the assembly of a functional repair complex for homologous recombination of DNA; and
(b) administering to the human patient a treatment capable of damaging cellular DNA.

In another embodiment, the agent disrupts the assembly of a functional repair complex for homologous recombination of DNA. In another embodiment, the agent that inhibits activity of RAD51 reduces cellular levels of RAD51. In another embodiment, the agent disrupts the formation of RAD51 foci.

In another embodiment, the agent that disrupts the assembly of a functional repair complex for homologous recombination of DNA is a therapeutically effective amount of at least one histone deacetylase inhibitor, or its pharmaceutically acceptable derivative. In another embodiment, the disease, disorder, or condition is cancer. In another embodiment, the DNA damaging agent is administered when the expression of RAD51 is within a pre-determined range. In another embodiment, the therapeutically effective amount of the at least one histone deacetylase inhibitor is from about 0.2 mg to about 2000 mg.

In another embodiment, the pre-determined range of the expression level of RAD51 is less than about 70% as compared to the expression level of RAD51 before the administration of the at least one histone deacetylase inhibitor. In another embodiment, the cancer is selected from the group consisting of: breast cancer, colon cancer, colorectal carcinomas, non-small cell lung cancer, small-cell lung cancer, liver cancer, ovarian cancer, prostate cancer, uterine cervix cancer, urinary bladder cancer, gastric carcinomas, gastrointestinal stromal tumors, pancreas cancer, germ cell tumors, mast cell tumors, neuroblastoma, mastocytosis, testicular cancers, glioblastomas, astrocytomas, lymphomas, melanoma, myelomas, acute myelocytic leukemia (AML), acute lymphocytic leukemia (ALL), myelodysplastic syndrome, and chronic myelogenous leukemia.

In another embodiment, the treatment capable of damaging cellular DNA comprises radiotherapy, or administration of a pharmaceutically effective amount of at least one anticancer agent, a known combination scheme for cancer therapy, or any combination thereof. In another embodiment, the treatment capable of damaging cellular DNA is radiotherapy or an administration of a pharmaceutically effective amount of at least one agent selected from the group consisting of topoisomerase inhibitors, tubulin interactors, DNA-interactive agents, DNA-alkylating agents, and platinum complexes.

In another embodiment, the treatment capable of damaging cellular DNA comprises radiotherapy. In another embodiment, the anticancer agent comprises cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, biphosphonates, or any combination thereof.

In another aspect are methods for treating diseases, disorders, or conditions associated with overexpression of homologous recombination of DNA or wherein the pathogenesis involves homologous recombination of DNA, comprising:
(a) administering to a human patient a therapeutically effective amount of at least one agent that inhibits activity of RAD51, disrupts the formation of RAD51 foci, or disrupts the assembly of a functional repair complex for homologous recombination of DNA, wherein the human patient has a disease, disorder, or condition associated with overexpression of homologous recombination of DNA or wherein the disease, disorder, or condition has a pathogenesis that involves homologous recombination; and
(b) administering to the human patient a treatment capable of damaging cellular DNA.

In another embodiment, the agent disrupts the assembly of a functional repair complex for homologous recombination of DNA. In another embodiment, the agent that inhibits activity of RAD51 reduces cellular levels of RAD51. In another embodiment, the agent disrupts formation of RAD51 foci.

In another embodiment, the agent that disrupts the assembly of a functional repair complex for homologous recombination of DNA is a therapeutically effective amount of at least one histone deacetylase inhibitor, or its pharmaceutically acceptable derivative. In another embodiment, the disease, disorder, or condition is cancer. In another embodiment, the disease, disorder, or condition is a viral infection. In another embodiment, the disease, disorder, or condition is Bloom's syndrome. In another embodiment, the DNA damaging agent is administered when the expression of RAD51 is within a pre-determined range. In another embodiment, the therapeutically effective amount of the at least one histone deacetylase inhibitor is from about 0.2 mg to about 2000 mg.

In another embodiment, the pre-determined range of the expression level of RAD51 is less than about 70% as compared to the expression level of RAD51 before the administration of the at least one histone deacetylase inhibitor. In another embodiment, the cancer is selected from the group consisting of: breast cancer, colon cancer, colorectal carcinomas, non-small cell lung cancer, small-cell lung cancer, liver cancer, ovarian cancer, prostate cancer, uterine cervix cancer, urinary bladder cancer, gastric carcinomas, gastrointestinal stromal tumors, pancreas cancer, germ cell tumors, mast cell tumors, neuroblastoma, mastocytosis, testicular cancers, glioblastomas, astrocytomas, lymphomas, melanoma, myelomas, acute myelocytic leukemia (AML), acute lymphocytic leukemia (ALL), myelodysplastic syndrome, and chronic myelogenous leukemia.

In another embodiment, the treatment capable of damaging cellular DNA comprises radiotherapy, or an administration of a pharmaceutically effective amount of at least one anticancer agent, a known combination scheme for cancer therapy, or any combination thereof. In another embodiment, the treatment capable of damaging cellular DNA is radiotherapy or an administration of a pharmaceutically effective amount of at least one agent selected from the group consisting of topoisomerase inhibitors, tubulin interactors, DNA-interactive agents, DNA-alkylating agents, and platinum complexes.

In another embodiment, the treatment capable of damaging cellular DNA comprises radiotherapy. In another embodiment, the anticancer agent comprises cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, biphosphonates, or any combination thereof.

In another embodiment are methods for treating cancer comprising
(a) administering to a human patient a therapeutically effective amount of at least one agent that inhibits activity of RAD51, disrupts the formation of RAD51 foci, or disrupts the assembly of a functional repair complex for homologous recombination of DNA, wherein the human patient has a cancer that maintains the length of its telomeres using a mechanism that does not involve telomerase, but rather via a mechanism known as the Alternative Lengthening of Telomere (ATL) pathway; and
(b) administering to the human patient an additional anticancer agent.

As many as 12% of all cancers and more than 50% of sarcomas, thyroid carcinomas, osteosarcomas, and glioblastomas fall within the aforementioned class of cancers. There is evidence that homologous recombination, including RAD51 specifically, is involved in the ALT pathway. RAD51 is found in ALT-associated PML bodies (APBs), and the mechanism of ALT is dependent on DNA double strand break machinery, especially homologous recombination and RAD51 in particular. HDAC inhibitors that mis-regulate RAD51 will be particularly useful in ALT positive cancers. In some embodiments, ALT is screened for by a relatively simple and robust assay.

In one aspect is a method for treating diseases, disorders, or conditions associated with a defect in non-homologous end joining of DNA, comprising: a) administering to a patient having a disease, disorder, or condition associated with a defect in non-homologous end joining of DNA, a therapeutically effective amount of at least one agent that inhibits the activity of BRCA1 or disrupts the interaction of BRCA1 and RAD51, or disrupts the assembly of a functional repair complex for homologous recombination for which BRCA1 is implicated; and b) administering to the patient a treatment capable of damaging cellular DNA.

In another aspect are pharmaceutical compositions comprising:
(a) a first coating for a first release of a therapeutically effective amount of at least one agent that inhibits activity of RAD51, disrupts the formation of RAD51 foci, or disrupts the assembly of a functional repair complex for homologous recombination of DNA; and
(b) a second coating for a second release of at least one other therapeutic agent.

In another aspect are pharmaceutical compositions comprising:
(a) a first coating for a first release of a therapeutically effective amount of at least one agent that inhibits the activity of BRCA1 or disrupts the interaction of BRCA1 and RAD51, or disrupts the assembly of a functional repair complex for homologous recombination for which BRCA1 is implicated; and
(b) a second coating for a second release of at least one other therapeutic agent.

In another embodiment, the second release occurs after the first release. In another embodiment, the agent that inhibits activity of RAD51 is at least one histone deacetylase inhibitor, or its pharmaceutically acceptable derivative. In another embodiment, the therapeutically effective amount of the at least one histone deacetylase inhibitor is from about 0.2 mg to about 2000 mg.

In a further embodiment, the second release occurs after the first release. In yet a further embodiment, the agent that inhibits the activity of BRCA1 is at least one histone deacetylase inhibitor, or its pharmaceutically acceptable derivative. In another embodiment, the therapeutically effective amount of the at least one histone deacetylase inhibitor is from about 0.2 mg to about 2000 mg.

In another embodiment, the at least one other therapeutic agent comprises an agent capable of damaging cellular DNA. In another embodiment, the agent capable of damaging cellular DNA is selected from the group consisting of topoisomerase inhibitors, tubulin interactors, DNA-interactive agents, DNA-alkylating agents, and platinum complexes.

In another embodiment, the at least one other therapeutic agent comprises cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, biphosphonates or any combination thereof.

In any of the aforementioned embodiments and aspects, the at least one histone deacetylase inhibitor is selected from the group consisting of carboxylates, short-chain fatty acids, hydroxamic acids, electrophilic ketones, epoxides, cyclic peptides, and benzamides.

In further embodiments, the histone deacetylase inhibitor is a compound selected from a compound or formula disclosed in U.S. patent application Ser. Nos. 10/818,755; 10/537,115; 10/922,119; 11/100,781; or PCT patent application No. PCT/US2005/046255.

In further embodiments, the histone deacetylase inhibitor is a hydroxamic acid having the structure of Formula (A):

Formula (A)

wherein:

Q is an optionally substituted $C_{5-12}$ aryl or an optionally substituted $C_{5-12}$ heteroaryl;

L is a linker having at least 4 atoms;

$R^1$ is H or alkyl;

and a pharmaceutically acceptable salt, pharmaceutically acceptable N-oxide, pharmaceutically active metabolite, pharmaceutically acceptable prodrug, pharmaceutically acceptable solvate thereof.

In another embodiment, the histone deacetylase inhibitor has the structure of Formula (I):

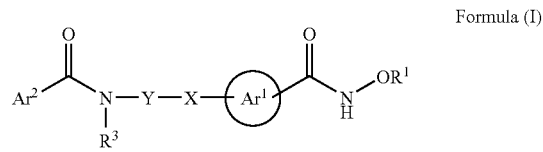

Formula (I)

wherein:

$R^1$ is hydrogen or alkyl

X is —O—, —$NR^2$—, or —$S(O)_n$— where n is 0-2 and $R^2$ is hydrogen or alkyl

Y is alkylene optionally substituted with cycloalkyl, optionally substituted phenyl, alkylthio, alkylsulfinyl, alkylsulfonyl, optionally substituted phenylalkylthio, optionally substituted phenylalkylsulfonyl, hydroxy, or optionally substituted phenoxy;

$Ar^1$ is phenylene or heteroarylene wherein said $Ar^1$ is optionally substituted with one or two groups independently selected from alkyl, halo, hydroxy, alkoxy, haloalkoxy, or haloalkyl;

$R^3$ is hydrogen, alkyl, hydroxyalkyl, or optionally substituted phenyl; and $Ar^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl;

and individual stereoisomers, individual geometric isomers, or mixtures thereof, or a pharmaceutically acceptable salt thereof.

In another embodiment, the histone deacetylase inhibitor has the structure:

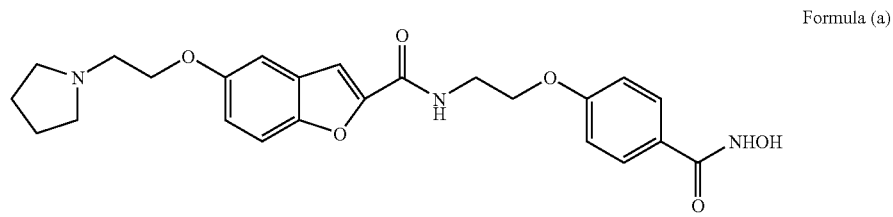

Formula (a)

or a pharmaceutically acceptable salt thereof.

In another embodiment, the histone deacetylase inhibitor has the structure:

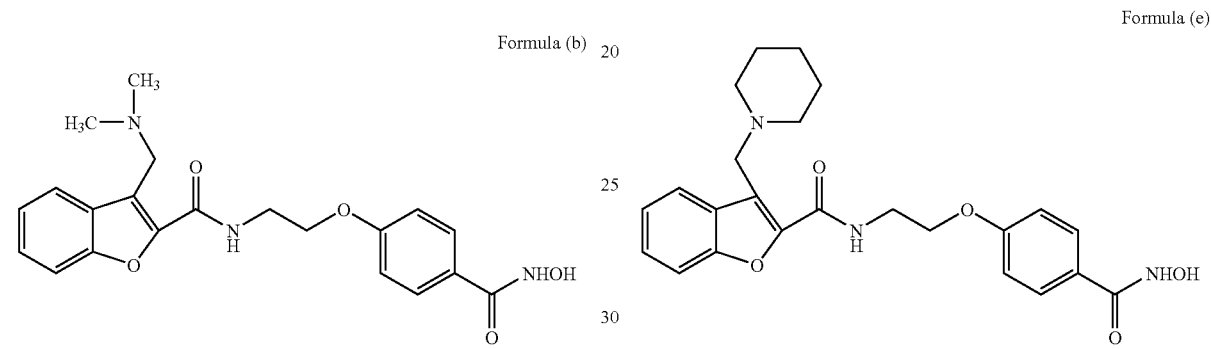

or a pharmaceutically acceptable salt thereof.

In another embodiment, the histone deacetylase inhibitor has the structure:

Formula (e)

or a pharmaceutically acceptable salt thereof.

In one aspect is a method for selecting a cancer treatment for a patient in need thereof, comprising: a) determining an expression level of RAD51 mRNA or a level of RAD51 protein in at least one cancer cell from the patient; and b) indicating that at least one histone deacetylase inhibitor is effective for treatment; if the expression level of RAD51 mRNA or the level of RAD51 protein in the biological sample is greater than an expression level of RAD51 mRNA or the level of RAD51 protein in a reference sample.

Other features and objects will be apparent from the description and from the claims. The details of one or more embodiments are set forth in the accompanying drawings and the description below. Other features and objects of the methods and pharmaceutical compositions described herein will be apparent from the description and drawings, and from the claims.

BRIEF DESCRIPTION OF THE DRAWINGS

FIG. 8C shows RAD51 protein and mRNA level decreases correlated with % Apoptosis.

DETAILED DESCRIPTION OF THE INVENTION

Figure 1:
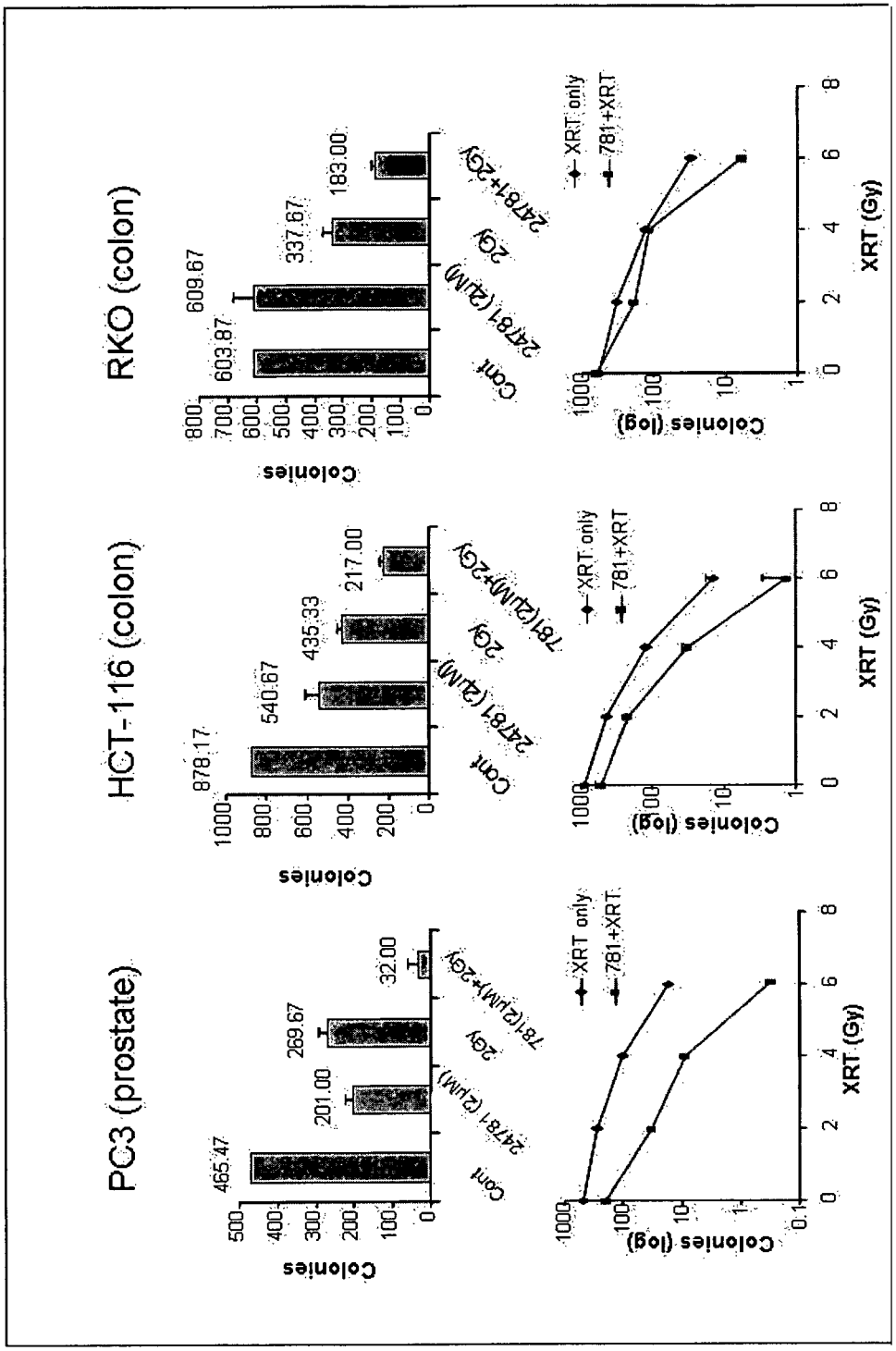
FIG. 1 shows the effects of pretreatment of a HDAC inhibitor test compound having the structure of Formula (A) or Formula (I) followed by ionizing radiation.

Unless defined otherwise, all technical and scientific terms used herein have the same meaning as is commonly understood by one of skill in the art to which the claimed subject matter belongs.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural references unless the context clearly dictates otherwise. In this application, the use of "or" means "and/or" unless stated otherwise. Furthermore, the use of the term "including" as well as other forms, such as "include", "includes," and "included," is not limiting.

Disruption of homologous recombination (HR) by HDAC inhibitors enables treatments with lower dosages of DNA-interacting agents or anticancer agents after pretreatment of HDAC inhibitors. In other embodiments, HR is directly disrupted by HDAC inhibitors, so HR mediated DNA repair is inhibited by HDAC inhibitors. In further embodiments, the disruption of HR is observed by monitoring RAD51 foci formation in the nucleus. In yet further embodiments, DNA double strand breaks (DSBs) are induced by ionizing radiation, and the radiation induced DSBs are typically repaired by HR during S-phase. Because RAD51 foci are disrupted in cells pre-treated with an HDAC inhibitor, repair of DSBs by HR is inhibited and cells become more sensitive to DNA interacting agents, such as certain anti-cancer agents.

In addition, RAD51 protein and mRNA levels are decreased following treatment with an HDAC inhibitor. Because DNA DSBs induced by radiation are unable to be repaired by HR after HDAC inhibitor treatment, DNA damage induced by DNA-interacting cancer drugs cannot be repaired by HR. Thus, tumor cells pretreated with at least one HDAC inhibitor will be hypersensitive to subsequent administration of (1) radiation, (2) DNA interacting drugs, and/or (3) any therapy that causes DSBs that are repaired by HR. In another embodiment, a synergistic effect is observed between at least one HDAC inhibitor and radiation, or between at least one HDAC inhibitor and one or more platinum agents.

Provided are methods for pre-treating a cancer patient with at least one HDAC inhibitor with an appropriate dose and scheduling a subsequent therapeutic treatment until HR is disrupted by the effect of the at least one HDAC inhibitor. In another embodiment, the disruption of HR for the cancer patient is monitored by (1) direct measurement of RAD51 foci formation in blood; (2) measurement of any surrogate biomarker in blood that reflects RAD51 foci formation in the tumor (for example, RAD51 level in PBMCs); (3) measurement of any marker that reflects the assembly of the machinery of homologous repair.

In other embodiments, patients with tumors which overexpress RAD51 are specifically targeted by the methods provided herein. Tumors which overexpress RAD51 typically have increased HR activity and are resistant to DNA interacting agents or DNA damaging agents. For example, most pancreatic tumors are RAD51 over-expressing tumors. In some embodiments, the methods provided herein with pre-treatment of at least one HDAC inhibitor at least partially overcome the resistance to DNA interacting agents or DNA damaging agents used for subsequent therapeutic treatments.

In some embodiments patients with tumors which have certain defects in Non-Homologous End Joining (NHEJ) are specifically targeted by the methods provided herein. Because the HR mechanism of DNA repair is the dominant pathway of DNA repair in tumors which have certain defects in NHEJ, in some embodiments, disruption of HR in these tumor cells completely block DNA repair activity and render these tumor cells sensitive to DNA interacting agents or DNA damaging agents used for subsequent therapeutic treatments. For example, tumor cells with mutations in Ku, a key player in NHEJ, are hypersensitive to HDAC inhibitor treatment.

In other embodiments, patients with any disease whose pathogenesis involves HR are also specifically targeted by the methods provided herein. For example, the HIV virus uses host HR during genome integration. Thus, in some embodiments, pretreatment of HDAC inhibitor are useful in viral diseases as well.

DEFINITIONS

Unless otherwise stated, the following terms used in the specification and claims are defined for the purposes of this application and have the following meanings:

In one embodiment, "alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

In another embodiment, "aryl" means a monovalent monocyclic or bicyclic aromatic hydrocarbon radical of 6 to 12 ring atoms e.g., phenyl, naphthyl or anthracenyl. Unless stated otherwise, the aryl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted phenylalkyl, optionally substituted heteroaryl, cycloalkyloxy, cycloalkenyloxy, optionally substituted phenylcarbonylamino, optionally substituted heteroaryloxy, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$—R$^a$ (where n is 0 to 2 and R$^a$ is alkyl, haloalkyl, hydroxyalkyl, alkoxyalkyl, optionally substituted phenyl, optionally substituted phenylalkyl, optionally substituted heteroaryl, or optionally substituted heteroaralkyl), -alkylene-NHSO$_2$—R$^b$ (where R$^b$ is alkyl, haloalkyl, optionally substituted phenyl, optionally substituted phenylalkyl, optionally substituted heteroaryl, optionally substituted heteroaralkyl, or optionally substituted heterocycloalkyl), -alkylene-NHCO—R$^c$ (where R$^c$ is alkyl, haloalkyl, optionally substituted phenyl, optionally substituted phenylalkyl, optionally substituted heteroaryl, optionally substituted heteroaralkyl, or optionally substituted heterocycloalkyl), or -(alkylene)$_{n1}$-CONR$^d$R$^e$ (where n$^1$ is 0 or 1, R$^d$ and R$^e$ are independently, hydrogen, alkyl, haloalkyl, hydroxyalkyl, alkoxyalkyl, aminoalkyl, optionally substituted phenyl, optionally substituted phenylalkyl, optionally substituted heteroaryl, optionally substituted heteroaralkyl, or optionally substituted heterocycloalkylalkyl, or R$^d$ and R$^e$ together with the nitrogen atom to which they are attached form heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. In some embodiments, the substituents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)-ethoxy, methoxymethyl, phenoxymethyl, 2-morpholino-4-ylethyl, morpholino-4-ylmethyl, N,N-dimethylaminomethyl, i-propoxymethyl, or phenoxymethyl.

The term "carrier," as used herein, refers to relatively non-toxic chemical compounds or agents that facilitate the incorporation of a compound into cells or tissues.

"EC$_{50}$," as used herein, refers to a dosage, concentration or amount of a particular test compound that elicits a dose-dependent response at 50% of maximal expression of a particular response that is induced, provoked or potentiated by the particular test compound.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism of the compound of Formula (A) or Formula (I), age, weight, general condition of the subject, the condition being treated, the severity of the condition being treated, and the judgment of the prescribing physician.

In some embodiments, "heterocycloalkyl" means a saturated or unsaturated monovalent cyclic group of 3 to 8 ring atoms in which one or two ring atoms are heteroatom selected from N, O, or S(O)$_n$, where n is an integer from 0 to 2, the remaining ring atoms being C. In other embodiments, one or two ring carbon atoms are optionally replaced by a —CO— group. In other embodiments, the term heterocycloalkyl includes, but is not limited to, pyrrolidino, piperidino, morpholino, piperazino, tetrahydropyranyl, tetrahydroquinolinyl and thiomorpholino, and the derivatives thereof (formed when the heterocyloalkyl ring is substituted with a substituent listed below); and an N-oxide or a protected derivative thereof. The heterocycloalkyl is optionally fused to aryl. Unless stated otherwise, the heterocyloalkyl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted phenylalkyl, cycloalkyloxy, cycloalkenyloxy, optionally substituted phenylcarbonylamino, optionally substituted heteroaryl, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$—R$^a$ (where n is 0 to 2 and R$^a$ is alkyl, haloalkyl, hydroxyalkyl, alkoxyalkyl, optionally substituted phenyl, optionally substituted phenylalkyl, optionally substituted heteroaryl, or optionally substituted heteroaralkyl), -alkylene-NHSO$_2$—R$^b$ (where R$^b$ is alkyl, haloalkyl, optionally substituted phenyl, optionally substituted phenylalkyl, optionally substituted heteroaryl, or optionally substituted heteroaralkyl), -alkylene-NHCO—R$^c$ (where R$^c$ is alkyl, haloalkyl, optionally substituted phenyl, optionally substituted phenylalkyl, optionally substituted heteroaryl, or optionally substituted heteroaralkyl), or -(alkylene)$_{n1}$-CONR$^d$R$^e$ (where n1 is 0 or 1, R$^d$ and R$^e$ are independently, hydrogen, alkyl, haloalkyl, hydroxyalkyl, alkoxyalkyl, aminoalkyl, optionally substituted phenyl, optionally substituted phenylalkyl, optionally substituted heteroaryl, optionally substituted heteroaralkyl, or optionally substituted heterocycloalkylalkyl, or $R^d$ and $R^e$ together with the nitrogen atom to which they are attached form heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. In some embodiments, the substituents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, i-propoxymethyl, or phenoxymethyl.

In other embodiments, "heteroaryl" means a monovalent monocyclic or bicyclic aromatic radical of 5 to 10 ring atoms where one or more (in some embodiments one, two, or three, ring atoms) are heteroatom selected from N, O, or S, the remaining ring atoms being carbon. In further embodiments, the term heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isoxazolyl, benzoxazolyl, benzothiophenyl, benzthiazolyl, quinolinyl, isoquinolinyl, benzofuranyl, benzopyranyl, and thiazolyl, and the derivatives thereof (formed when the heterocycloalkyl ring is substituted with a substituent listed below); or an N-oxide or a protected derivative thereof. Unless stated otherwise, the heteroaryl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, cycloalkyloxy, cycloalkenyloxy, optionally substituted phenylcarbonylamino, optionally substituted heteroaryl, optionally substituted heteroaryloxy, optionally substituted heteroaralkyloxy, aminoalkyl, aminoalkoxy, alkoxyalkyl, alkoxyalkyloxy, methylenedioxy, haloalkoxyalkyl, optionally substituted phenylalkyl, optionally substituted phenyloxy, optionally substituted phenylalkyloxy, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$—$R^a$ (where n is 0 to 2 and $R^a$ is alkyl, hydroxyalkyl, haloalkyl, optionally substituted phenyl, optionally substituted phenylalkyl, optionally substituted heteroaryl, or optionally substituted heteroaralkyl), -alkylene-NHSO$_2$—$R^b$ (where $R^b$ is alkyl, haloalkyl, optionally substituted phenyl, optionally substituted phenylalkyl, optionally substituted heteroaryl, optionally substituted heteroaralkyl, or optionally substituted heterocycloalkyl), -alkylene-NHCO—$R^c$ (where $R^c$ is alkyl, haloalkyl, hydroxyl, optionally substituted phenyl, optionally substituted phenylalkyl, optionally substituted heteroaryl, optionally substituted heteroaralkyl, or optionally substituted heterocycloalkyl), -(alkylene)$_{n1}$-CONR$^d$R$^f$ (where n1 is 0 or 1, $R^d$ is hydrogen or alkyl, and $R^f$ is hydrogen, alkyl, hydroxylalkyl, alkoxyalkyl, optionally substituted phenyl, optionally substituted phenylalkyl, optionally substituted heteroaryl, optionally substituted heteroaralkyl, or optionally substituted heterocycloalkylalkyl, or $R^d$ and $R^f$ together with the nitrogen atom to which they are attached form heterocycloalkyl, -alkylene-NR$^e$-alkyleneCONR$^c$R$^d$ (where $R^c$ is as defined above and $R^d$ and $R^e$ are independently hydrogen or alkyl), or carboxyalkylaminoalkyl wherein the alkyl chain in haloalkoxyalkyl, optionally substituted phenyloxyalkyl, optionally substituted heteroaryloxyalkyl, or aminoalkyl is optionally substituted with one or two fluoro. In some embodiments, the substituents are independently methoxy, methyl, ethyl, chloro, trifluoromethyl, fluoro, 2-methoxyethoxy, 2-(morpholin -4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylamino-methyl, i-propoxymethyl, or phenoxymethyl.

When the heteroaryl ring is divalent it has been referred to as heteroarylene in this application.

"IC$_{50}$," as used herein refers to an amount, concentration or dosage of a particular test compound that achieves a 50% inhibition of a maximal response in an assay that measures such response.

"Isomer" or "isomers" means compounds of Formula (A) or Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are non-superimposable mirror images are termed "enantiomers" or sometimes "optical isomers." An atom bonded to four non-identical substituents is termed a "chiral center." A compound with one chiral center has two enantiomeric forms of opposite chirality; and a mixture of both enantiomeric forms in equal amounts is termed racemic. A compound that has one or more chiral centers has $2^{n-1}$ enantiomeric pair(s), where n is the number of chiral centers, unless the compound is meso (i.e. the compound has 2 or more asymmetric or chiral centers but which is achiral because it contains an internal plane of symmetry). In some embodiments, compounds with more than one chiral center exist as either an individual diastereomer or as a mixture of diastereomers, termed a "diastereomeric mixture." In some other embodiments, when one chiral center is present a stereoisomer is characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "*Advanced Organic Chemistry,*" 4th edition, March, Jerry, John Wiley & Sons, New York, 1992). It is understood that the names and illustration used in this application to describe compounds of Formula (A) or Formula (I) are meant to be encompassed all possible stereoisomers and any mixture, racemic or otherwise, thereof.

Also described herein are prodrugs of compounds of Formula (A) or Formula (I). The term prodrug is intended to represent covalently bonded carriers, which are capable of releasing the active ingredient of Formula (A) or Formula (I) when the prodrug is administered to a mammalian subject. Release of the active ingredient occurs in vivo. In some embodiments, techniques for preparing prodrugs generally modify appropriate functional groups in a given compound. These modified functional groups however regenerate original functional groups by routine manipulation or in vivo. Prodrugs of compounds of Formula (A) or Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (A) or Formula (I)), amides (e.g., trifluoroacetylamino, acetylamino, and the like), and the like.

Also described herein are N-oxide derivatives and protected derivatives of compounds of Formula (A) or Formula (I). For example, in some embodiments, when compounds of Formula (A) or Formula (I) contain an oxidizable nitrogen atom, the nitrogen atom is converted to an N-oxide by known methods. In other embodiments, when compounds of Formula (A) or Formula (I) contain groups such as hydroxy, carboxy, thiol or any group containing a nitrogen atom(s), these groups are protected with a suitable protecting groups. A comprehensive list of suitable protective groups is found in T. W. Greene, *Protective Groups in Organic Synthesis*, John Wiley & Sons, Inc. 1981, the suitable list of protective groups of which is incorporated herein by reference. In other embodiments, the protected derivatives of compounds of Formula (A) or Formula (I) are prepared by known methods.

A "pharmaceutically acceptable derivative" includes, but not limited to, a pharmaceutically acceptable salt, pharmaceutically acceptable N-oxide, pharmaceutically active metabolite, pharmaceutically acceptable prodrug, pharmaceutically acceptable solvate, or pharmaceutically acceptable ester thereof.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts are found in *Remington's Pharmaceutical Sciences*, 17th ed., Mack Publishing Company, Easton, Pa., 1985, the list of pharmaceutically acceptable salts which is incorporated herein by reference.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. In some embodiments, a "pharmaceutically acceptable carrier/excipient" as used in the specification and claims includes both one and more than one such excipient.

In other embodiments, the compounds of Formula (A) or Formula (I) have asymmetric centers. In other embodiments, compounds of Formula (A) or Formula (I) containing an asymmetrically substituted atom are isolated in optically active or racemic forms. All chiral, diastereomeric, racemic forms are described herein, unless the specific stereochemistry or isomeric form is specifically indicated.

In some embodiments, certain compounds of Formula (A) or Formula (I) exist as tautomers and/or geometric isomers. All possible tautomers and cis and trans isomers, individual and mixtures thereof are intended to be covered. Additionally, as used herein the terms alkyl includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth. Furthermore, all polymorphic forms and hydrates of a compound of Formula (A) or Formula (I) are intended to be covered.

"Optionally substituted" when modifying a particular group, means that the group the term modifies may, but does not have to, be substituted. Where the term "optionally substituted" is used to modify a particular group, this does not mean, unless otherwise stated, that any other groups not so modified cannot also be optionally substituted. Furthermore, where a group is defined as being substituted by one of a number of enumerated alternative substituents, it does not mean, unless otherwise stated, that the group cannot be substituted further with one or more substituents not enumerated. For example, "optionally substituted heterocycloalkyl" means that the heterocycloalkyl may but need not be substituted with the enumerated substituents within the definition of "optionally substituted heterocycloalkyl"; and the description includes situations where the heterocycloalkyl group is substituted and situations where the heterocycloalkyl group is not substituted.

"Optionally substituted phenyl" means a phenyl ring optionally substituted with one, two, or three substituents independently selected from alky, halo, alkoxy, alkylthio, haloalkyl, haloalkoxy, heteroaryl (that is optionally substituted with one or two substituents independently selected from alky, halo, hydroxy, alkoxy, carboxy, amino, alkylamino, or dialkylamino), heterocycloalkyl (that is optionally substituted with one or two substituents independently selected from alkyl, halo, hydroxy, alkoxy, carboxy, amino, alkylamino, or dialkylamino), amino, alkylamino, dialkylamino, hydroxy, cyano, nitro, methylenedioxy, aminocarbonyl, acylamino, hydroxyalkyl, alkoxycarbonyl, aminoalkyl, or carboxy or optionally substituted with five fluorine atoms. When the phenyl is substituted it is referred herein as "substituted phenyl."

In some embodiments, "optionally substituted heteroaryl" means a monovalent monocyclic or bicyclic aromatic radical of 5 to 10 ring atoms where one or more (in some embodiments one, two, or three, ring atoms) are heteroatoms selected from N, O, or S, the remaining ring atoms being carbon that is optionally substituted with one, two, or three substituents independently selected from alkyl, halo, alkoxy, haloalkyl, haloalkoxy, amino, alkylamino, dialkylamino, hydroxy, cyano, nitro, aminocarbonyl, hydroxyalkyl, alkoxycarbonyl, aminoalkyl, optionally substituted phenyl, optionally substituted phenoxy, carboxy, or heteroaryl that is optionally substituted with alkyl, halo, hydroxy, alkoxy, carboxy, amino, alkylamino, or dialkylamino, heterocycloalkyl optionally substituted with one or two substituents independently selected from alkyl, halo, hydroxy, alkoxy, amino, alkylamino or dialkylamino, heterocycloalkylalkyl optionally substituted with one or two substituents independently selected from alkyl, halo, hydroxy, alkoxy, amino, alkylamino or dialkylamino, or heteroarylamino optionally substituted with one or two substituents independently selected from alkyl, halo, hydroxy, alkoxy, amino, alkylamino or dialkylamino. More specifically the term optionally substituted heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isoxazolyl, benzoxazolyl, quinolinyl, isoquinolinyl, benzopyranyl, and thiazolyl, and the derivatives thereof (formed when the heteroaryl ring is substituted with a substituent listed above); or an N-oxide or a protected derivative thereof.

In further embodiments, "optionally substituted heterocycloalkyl" means a saturated or unsaturated monovalent cyclic group of 3 to 8 ring atoms in which one or two ring atoms are heteroatoms selected from N, O, or $S(O)_n$, where n is an integer from 0 to 2, the remaining ring atoms being C. In another embodiment, one or two ring carbon atoms are optionally replaced by a —CO— group. In other embodiments, the term heterocycloalkyl includes, but is not limited to, pyrrolidino, piperidino, morpholino, piperazino, tetrahydropyranyl, and thiomorpholino and the derivatives thereof (formed when the heterocycloalkyl ring is substituted with a substituent listed below); or an N-oxide or a protected derivative thereof. The heterocycloalkyl is optionally fused to aryl and is optionally substituted with one, two, or three substituents independently selected from alkyl, cycloalkyl, halo, alkoxy, haloalkyl, haloalkoxy, amino, alkylamino, dialkylamino, hydroxy, cyano, nitro, optionally substituted phenylalkyl, optionally substituted heteroaralkyl aminocarbonyl, hydroxyalkyl, alkoxycarbonyl, aminoalkyl, or carboxy.

"RNAi" or "RNA interference" refers to the introduction of homologous double-stranded RNA (dsRNA) to specifically target a gene transcript, resulting in null or hypomorphic levels of the resulting protein. RNAi methods are highly sequence-specific and very sensitive with only a few dsRNA molecules required per cell for effective interference.

In some embodiments, "treating" or "treatment" of a disease, disorder, or condition includes at least partially:

(1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition;

(2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

By way of convenience only, unless stated otherwise, the term "Formula (A) or Formula (I)" is used as an abbreviation for any compound having the structure of Formula (A), Formula (I), Formula (a), Formula (b), Formula (c), Formula (d), Formula (e), compounds of any specific embodiments described herein, and any specific compound described herein covered by any of the above mentioned generic formulas.

Homologous Recombination and DNA Repair

Cellular DNA undergoes double strand breakage (DSB) during the course of many physiological events as well as in response to a variety of environmental insults. In some cases, if left unrepaired, such DSBs lead to mutations that will prove lethal to the organism. In human cells, repair of DNA DSBs occurs either by homologous recombination (HR) or by non-homologous end-joining (NHEJ). Homologous recombination is known to involve the RAD51, RAD52, RAD54, RAD55-57 and RPA proteins. More recently, the BRCA1 and BRCA2 cancer-susceptibility proteins have also been suggested to play a role in homologous DSBR repair through interactions with RAD50 and RAD51. RAD51 is suggested as a stably-associated core component of the multi-protein HR-repair complex at sites of DNA damage and that its associated proteins, such as RAD52 and RAD54, rapidly and reversibly interact with the focal RAD51 DNA repair complex.

Homologous recombination is a fundamental process which is important for maintaining genome integrity. In *E. coli*, the RecA protein plays a central role in homologous genetic recombination in vivo and promotes homologous pairing of double-stranded DNA with single-stranded DNA or partially single-stranded DNA molecules in vitro. In the yeast *Saccharomyces cerevisiae*, there are several genes with homology to the RecA gene; i.e., RAD51, RAD57 and DMC1. All the members of the RAD51 family and their bacterial counterpart (RecA) share an important structural motif known as the "RecA signature sequence" (also called as "homologous core region" or Domain II.) This sequence forms the ATP binding sites, an important property of all these proteins. However, the eukaryotic members of the RAD51 family can be distinguished from the bacterial RecA protein by the presence of an N-terminal extension present only in the RAD51 family members and a C-terminal extension of about 100 amino acids that is present in RecA but not in RAD51 family members. All known members of the RAD52 epistasis group are required for DSB repair and genetic recombination. Functional analysis has revealed interactions of RAD57 with RAD51, RAD52 and RAD55 to form a "recombinosome" (Johnson, R. et al., 1995, *Mol. Cell. Biol.* 15: 4843 4850).

Many valuable and life-saving chemotherapeutic drugs, actively used in the clinic, achieve their effect by damaging DNA in proliferating cells, such as (1) alkylating agents, such as temozolomide, sarmustine, chlorambucil, melphalan, dacarbazine, BCNU and SCNU; (2) nucleoside analogues, such as fludarabine, iodouridinedeoxyribose, gemcitabine, and fluorodeoxyuridine; and (3) radiation therapy. These treatments result in cytotoxic modifications in DNA bases, which initially lead to Single Strand Breaks (SSB) in the drug-incorporated DNA strand as well as in the un-substituted complementary-strand DNA. These SSBs subsequently result in increase in the amount of DSBs which, if not repaired properly, result in cell death.

In some embodiments, where cells are resistant to certain DNA damaging agents, various radio- and chemo-sensitizing agents are used to increase the sensitivity to these DNA damaging agents. Often proliferating tumor or viral infected cells are resistant to chemo- and radiotherapy due to over-expression of the DNA repair mechanisms. Since SSBs can be converted to DSBs, even if one of these pathways is blocked, the other pathway may enable cells to repair damage and sustain viability. In some embodiments, agents that inhibit DNA repair in a specific and potent manner sensitize proliferating cells to a broad spectrum of anticancer agents. Since cancer cells rely on DNA repair to allow them to grow rapidly, this sensitization would enhance the specificity of cancer therapy and allow more effective therapy with lower side effects than is possible with current therapeutic regimens.

RAD51 and RAD51 Inhibitors

RAD51, a eukaryotic recombinase and a homolog of the bacterial RecA protein involved in homologous recombination, catalyzes double-stranded break repair (DSBR) in damaged cells. RAD51 is a member of the RAD52 epistasis group, which includes RAD50, RAD51, RAD52, RAD54, RAD55 and RAD57. In some embodiments, the methods provided herein alter the expression or the activity of at least one protein selected from the group consisting of the RAD52 epistasis group proteins RAD51, RAD52, RAD54, RAD55, MRE11 and XRS2, the mismatch repair group protein PMS1, and the nucleotide excision repair group protein RAD10. Phylogenetic analysis by Ogawa and co workers suggested the existence of two sub-families within eukaryotic RecA homologs: the RAD51-like (RAD51 of human, mouse, chicken, *S. cerevisiae, S. pombe* and Mei3 of *Neurospora crassa*) and the DMC 1-like genes (*S. cerevisiae* DMC 1 and *Lilium longiflorum* LIM15).

The RAD51 protein is important for the repair of DSB in damaged cells. In *S. cerevisiae*, genes with homology to RecA include RAD51, RAD57 and DMC1. RAD51 is highly overexpressed in certain tumor cells, and down-regulating its activity results in inhibition of DSB repair. The RAD51 protein plays a pivotal role in gene conversion during homologous recombination induced by ionizing (IR) or ultraviolet (UV) irradiation, DNA damaging agents, and replication elongation agents and is plays a role in sister-chromatid exchange (SCE). In further embodiments, increased expression level of *E. coli* RecA or RAD51 increases the resistance of cells to radiation or other DNA damaging agents.

In one embodiment, RAD51 includes homologs of RAD51. In one embodiment, RAD51 homologs are defined by the RAD51's role in recombinational repair. In another embodiment, RAD51 homologs are proteins which share significant sequence identity with residues 33-240 of *E. coli* RecA protein, which is the "RecA signature sequence" or "homologous core region" as described above. RAD51 homologs include RecA and RAD51 homologs in yeast and in mammals (see above). In another embodiment, RAD51 is a dimer. In a further embodiment, the dimer is a homodimer or heterodimer. In some embodiments, the heterodimer is formed from two different homologs. In one embodiment, the homologs are selected from the group consisting of RAD51A, RAD51B, RAD51C, and RAD51D. In some embodiments, the dimer includes RAD51C or RAD51B in any combination.

In a further embodiment, the level of RAD51 expression is determined by the level of RAD51 protein or nucleic acid. In some embodiments, a labeled binding agent that binds to RAD51 is used to detect RAD51 proteins. The term "labeled" herein refers to a compound having at least one element, isotope or chemical compound attached to enable the detection of the compound. In some embodiments, labels fall into three classes: (1) isotopic labels, which are radioactive or heavy isotopes; (2) immune labels, which are antibodies or antigens; (3) colored or fluorescent dyes. In another embodiment, the binding agent is either labeled directly, or indirectly, through the use of a labeled secondary agent which binds to the first binding agent. In one embodiment, the level is determined through the use of polyclonal antibodies. In some embodiments, the level is determined through the use of monoclonal antibodies. In some embodiments, said antibodies are raised against eukaryotic RAD51. In some embodiments, the eukaryotic RAD51 is a mammalian RAD51. In another embodiment, the antibodies are raised against a RAD51 homolog. In a further embodiment, the RAD51 expression is determined by the level of RAD51 nucleic acid, such as mRNA, with similar labeling strategies as described above.

By "biologicalactivity" of RAD51 herein includes, but not limited to, RAD51 DNA dependent ATPase activity, the nucleic acid strand exchange activity, the formation of foci, single-stranded and double-stranded binding activities, filament formation (similar to the RecA filament of yeast), pairing activity (D-loop formation), etc.

In another embodiment, inhibition of RAD51 biological or biochemical activity as used herein is measured from RAD51 activities selected from the group consisting of DNA dependent ATPase activity, formation of RAD51 foci, nucleic acid strand exchange, DNA binding, nucleoprotein filament formation, DNA pairing and DNA repair. DNA repair and recombination are generally considered biological activities of RAD51. In further embodiments, DNA repair are double stranded break repair, single stranded annealing, or post replication recombinational repair.

A RAD51 inhibitor or an agent or composition having RAD51 inhibitory activity is defined herein as an agent or composition that inhibits the expression or translation of a RAD51 nucleic acid or the biological activity of a RAD51 peptide by at least about 30%, at least about 40%, at least about 50%, at least about 70%, at least about 90%, and at least about 95%. In one embodiment, RAD51 inhibitors such as compounds having the structure of Formula (A) or Formula (I) inhibit expression or translation of a RAD51 nucleic acid or the activity of a RAD51 protein by at least about 70%. In another embodiment, inhibition of RAD51 activity is defined as any detectable decrease in RAD51 activity compared to a control not comprising the RAD51 inhibitor.

In one aspect is a method for treating a cancer, comprising:
(a) administering to a patient having the cancer a therapeutically effective amount of at least one agent that inhibits the activity of RAD51, disrupts the formation of RAD51 foci, or disrupts the assembly of a functional repair complex for homologous recombination of DNA; and
(b) administering to the patient a treatment capable of damaging cellular DNA.

In one embodiment, the at least one cancer cell from the patient has a defect in non-homologous end joining of DNA.

In one aspect are methods for treating diseases, disorders, or conditions associated with a defect in non-homologous end joining of DNA, comprising: (a) administering to a human patient having a disease, disorder, or condition associated with a defect in non-homologous end joining of DNA, a therapeutically effective amount of at least one agent that inhibits the activity of RAD51, disrupts the formation of RAD51 foci, or disrupts the assembly of a functional repair complex for homologous recombination of DNA; and (b) administering to the human patient a therapeutically effective amount of a DNA damaging agent. In a further embodiment, the DNA damaging agent is doxorubicin. In one embodiment, the at least one agent that inhibits the activity of RAD51, disrupts the formation of RAD51 foci, or disrupts the assembly of a functional repair complex for homologous recombination of DNA is at least one histone deacetylase inhibitor. In another embodiment, the administering of the at least one histone deacetylase inhibitor and doxorubicin are administered simultaneously. In a further embodiment, the administering of the at least one histone deacetylase inhibitor and doxorubicin have a synergistic effect. In another embodiment, the effect is additive. In yet a further embodiment, the disease, disorder, or condition is Non-Hodgkins lymphoma.

RAD51 inhibitors also include, but are not limited to, peptide inhibitors of RAD51 (including but not limited to amino acids 94-160 and 264-315 of p53 and RAD51 antibodies; including but not limited to single chain antibodies), small molecules, nucleotide analogues (including but not limited to ADP analogs, ATPγS), minor groove DNA binding drugs as inhibitors of RAD51 (including but not limited to distamycin and derivatives thereof), known radiation sensitizers (e.g., xanthine and xanthine derivatives including caffeine) on the biochemical activities of RAD51, antigenes against RAD51, particularly those which inhibit transcription by locked hybrids, and antisense molecules. In another embodiment, the inhibitor inhibits RAD51 directly or indirectly, by interacting with at least a portion of the RAD51 nucleic acid, RAD51 mRNA, or RAD51 protein. Additionally, the inhibitors herein are utilized individually or in combination with each other.

In a further embodiment, RAD51 inhibitors such as compounds having the structure of Formula (A) or Formula (I) include inhibitors of RAD51 homologs, which include, but not limited to, RAD51B, RAD51C, RAD51D, XRCC2 and XRCC3, and other RecA homologs (see above).

In further embodiments, in cultured human cells, RAD51 protein is detected in multiple discrete foci in the nucleoplasm by immunofluorescent antibodies. After DNA damage, the localization of RAD51 changes dramatically when multiple foci form in the nucleus and stain vividly with anti-RAD51 antibodies. Typically after DNA damage, the cells with focally concentrated RAD51 protein increases show unscheduled DNA-repair synthesis. Two main types of RAD51 foci have been identified and in situ immunostaining with RAD51 antibodies reveals three kinds of nuclei: (1) nuclei that did not show any staining at all (no foci); (2) nuclei that showed weak to medium staining and showed only a few foci (Type I nuclei); and (3) nuclei that showed strong staining and showed many foci (Type II nuclei). In normal cells, type I nuclei are typically found in 7-10% of cells and type II nuclei in less than 0.4 to 1% of cells, with generally about 90% of the cells showing no foci. In contrast, some cells involved in disease states show a marked increase in RAD51 foci.

RAD51 foci are determined in a variety of ways. In some embodiments, a labeled binding agent that binds to RAD51 is used to visualize the foci. In one embodiment, the labels are incorporated into the binding agent at any position. In some embodiments, the labels are fluorescent or radioactive labels. In another embodiment, the binding agent is either labeled directly, or indirectly, through the use of a labeled secondary agent which will bind to the first binding agent. The cells or tissue sample is prepared as is known for cellular or in situ staining, using standard techniques.

In some embodiments, the binding agent used to detect RAD51 foci is an antibody. In one embodiment the antibodies are either polyclonal or monoclonal. In some embodiments, the antibodies to the particular RAD51 under evaluation are used; that is, antibodies directed against human RAD51 are used in the evaluation of human patients. However, as the homology between different mammalian RAD51 molecules is quite high (73% identity as between human and chicken, for example), it is possible to use antibodies against RAD51 from one type of animal to evaluate a different animal (mouse antibodies to evaluate human tissue, etc.) Thus, in some embodiments, antibodies raised against eukaryotic RAD51 are used. In some embodiments, the eukaryotic RAD51 is a mammalian RAD51. Thus, in some embodiments, antibodies raised against yeast, human, rodent, primate, and avian RAD51 proteins are used. In addition, the protein used to generate the antibodies need not be the full-length protein; in some embodiments, fragments and derivatives are used, as long as there is sufficient immunoreactivity against the sample RAD51 to allow detection. In another embodiment, other binding agents which will bind to RAD51 at sufficient affinity to allow visualization are used.

RAD51 mRNA/Protein Patient Selection

In one aspect is a method for selecting a cancer treatment for a patient in need thereof, comprising: a) determining an expression level of RAD51 mRNA or a level of RAD51 protein in at least one cancer cell from the patient; and b) indicating that at least one histone deacetylase inhibitor is effective for treatment; if the expression level of RAD51 mRNA or the level of RAD51 protein in the biological sample is greater than an expression level of RAD51 mRNA or the level of RAD51 protein in a reference sample. In one embodiment, the method comprises determining the expression level of RAD51 mRNA in at least one cancer cell from the patient. In another embodiment, the method comprises determining the level of RAD51 protein in at least one cancer cell from the patient. In one embodiment is a method wherein indicating comprises providing results that at least one histone deacetylase inhibitor is likely to be effective for treatment. In another embodiment is a method wherein indicating comprises providing results that at least one histone deacetylase inhibitor is likely to respond to treatment. In yet another embodiment, the method further comprises administering a therapeutically effective amount of at least one histone deacetylase inhibitor. In yet a further embodiment, the at least one histone deacetylase inhibitor is selected from a compound of Formula (A) or (I). In another embodiment, the at least one histone deacetylase inhibitor is selected from a compound of Formula (A), (B), (C), and/or (D). In yet another embodiment, the at least one histone deacetylase inhibitor is 3-((dimethylamino)methyl)-N-(2-(4-(hydroxycarbamoyl)phenoxy)ethyl)benzofuran-2-carboxamide. In one embodiment, the reference sample is HH cutaneous T-cell lymphoma cell line. In another embodiment, the level of RAD51 protein in the reference sample is a reference level in a HH cutaneous T-cell lymphoma cell line. In another embodiment, the level of RAD51 protein in the reference sample is at least about 50%, at least about 60%, at least about 70%, at least about 75%, at least about 80%, at least about 90%, about 100% of the level of RAD51 protein a biological sample. In another embodiment, the level of RAD51 protein in the reference sample is at least about 1½ fold, at least about 2 fold, at least about 3 fold, at least about 4 fold, at least about 5 fold, at least about 6 fold, at least about 7 fold, at least about 8 fold, at least about 9 fold, at least about 10 fold, at least about 12 fold, at least about 15 fold, or at least about 20 fold the level of RAD51 in a biological sample. In a further embodiment, the reference sample is normalized to an internal protein. In yet a further embodiment, the internal protein is actin. In one embodiment, normalization of the reference sample is determined by Western blotting. In another embodiment, the reference sample correlates to an in vitro % level of Apoptosis. In a further embodiment, the % level of Apoptosis is below about 20%. In yet a further embodiment, the % level of Apoptosis is below about 15%. In another embodiment, the % level of Apoptosis is below about 10%. In a further embodiment, the % level of Apoptosis is below about 5%.

In one embodiment, the method for selecting a patient in need of treatment further comprises prescribing or administering at least one histone deacetylase inhibitor based on the results of the indicating step. In one embodiment, the expression level of RAD51 mRNA or the level of RAD51 protein in the biological sample is determined by standard immunodetection methods (e.g. Western Blot Analysis, radio-immunoassay, or ELISA).

BRCA1 and BRCA1 Modulators

BRCA1 is a human gene that belongs to a class of genes known as tumor suppressors, which maintains genomic integrity to prevent uncontrolled proliferation. The multifactorial BRCA1 protein functions in DNA damage repair, ubiquitination, transcriptional regulation as well as other processes. Variations in the gene have been implicated in a number of hereditary cancers, namely breast, ovarian and prostate. The BRCA1 protein is directly involved in the repair of damaged DNA.

In the nucleus of many types of normal cells, the BRCA1 protein is thought to interact with RAD51 to mend breaks in DNA. These breaks can be caused by natural radiation or other exposures, but also occur when chromosomes exchange genetic material in preparation for cell division. The BRCA2 protein, which has a function similar to that of BRCA1, also interacts with the RAD51 protein.

In some embodiments, the methods provided herein inhibit the expression or the activity of BRCA1. In one embodiment is a BRCA1 inhibitor or an agent or composition having BRCA1 inhibitory activity is defined herein as an agent or composition that reduces the level of BRCA1 mRNA or protein by at least about 30%, about 40%, about 50%, about 70%, about 90%, and about 95%. In one embodiment, BRCA1 inhibitors have the structure of Formula (A) or Formula (I) inhibit expression or translation of a BRCA1 nucleic acid or the activity of a BRCA1 protein by at least about 70%. In another embodiment, inhibition of BRCA1 activity is defined as any detectable decrease in BRCA1 activity compared to a sample that has not been exposed to the BRCA1 inhibitor.

In one aspect is a method for treating a cancer, comprising: (a) administering to a patient having the cancer a therapeutically effective amount of at least one agent that inhibits the activity of BRCA1, or disrupts the interaction of BRCA1 and RAD51, or disrupts the assembly of a functional repair complex for homologous recombination for which BRCA1 is implicated; and
(b) administering to the patient a treatment capable of damaging cellular DNA.

In one embodiment, the at least one cancer cell from the patient has a defect in non-homologous end joining of DNA.

BRCA1 is implicated in the upregulation of RAD51. Accordingly, in some embodiments provided herein is a method for treating a disease (e.g., a cancer), disorder, or condition comprising a) administering a BRCA1 inhibitor; and b) administering a treatment capable of damaging cellular DNA wherein the BRCA1 inhibitor downregulates RAD51. In one embodiment, the BRCA1 inhibitor is a histone deacetylase inhibitor described herein. In another embodiment, the inhibitor inhibits BRCA1 directly or indirectly, by interacting with at least a portion of the BRCA1 nucleic acid, BRCA1 mRNA, or BRCA1 protein. In other embodiments, the inhibitors herein are utilized individually or in combination with each other.

In one embodiment is a method for treating a disease, disorder, or condition wherein at least one histone deacetylase inhibitor interferes with a DNA repairing mechanism involving BRCA1.

In another embodiment is a method for treating a disease, disorder, or condition in a patient wherein BRCA1 is implicated in double stranded DNA repair comprising: a) administering to the patient a therapeutically effective amount of at least one agent that modulates the activity of BRCA1; and b) administering to the patient a treatment capable of damaging cellular DNA. In another embodiment is a method wherein modulation is inhibition of the activity of BRCA1.

In one embodiment, the at least one agent that modulates the activity of BRCA1 is at least one histone deacetylase inhibitor or its pharmaceutically acceptable derivative. In another embodiment, the at least one agent that modulates the activity of BRCA1 inhibits the activity of BRCA1. In a further embodiment, the at least one agent that modulates the activity of BRCA1 reduces cellular levels of BRCA1. In another embodiment, the activity of BRCA1 upregulates RAD51. In yet another embodiment, the at least one agent that modulates the activity of BRCA1 inhibits the activity of RAD51. In a further embodiment, the at least one agent that modulates the activity of BRCA1 reduces the cellular levels of RAD51. In another embodiment, the disease, disorder, or condition is cancer. In a further embodiment, the cancer is breast cancer, ovarian cancer, or prostate cancer. In one embodiment, the treatment capable of damaging cellular DNA is administered when the expression of BRCA1 is within a pre-determined range. In yet a further embodiment, the histone deacetylase inhibitor is from about 0.2 mg to about 2000 mg. In another embodiment, at least one histone deacetylase inhibitor is from about 0.2 mg to about 1000 mg, about 1 mg to about 200 mg, about 5 mg to about 100 mg, about 5 to about 50 mg, and about 5 to about 20 mg. In another embodiment, the patient is human.

In one aspect is a method for treating diseases, disorders, or conditions associated with a defect in non-homologous end joining of DNA, comprising: a) administering to a patient having a disease, disorder, or condition associated with a defect in non-homologous end joining of DNA, a therapeutically effective amount of at least one agent that modulates the activity of BRCA1 or disrupts the interaction of BRCA1 and RAD51, or disrupts the assembly of a functional repair complex for homologous recombination for which BRCA1 is implicated; and b) administering to the patient a treatment capable of damaging cellular DNA. In another embodiment, the at least one agent modulates the activity of BRCA1. In another embodiment, the at least one agent disrupts the interaction of BRCA1 and RAD51. In a further embodiment, the at least one agent disrupts the assembly of a functional repair complex for homologous recombination for which BRCA1 is implicated. In a further embodiment, the at least one agent is at least one histone deacetylase inhibitor. In yet a further embodiment, the at least one histone deacetylase inhibitor is a hydroxamic acid having the structure of Formula (A):

Formula (A)

wherein:
Q is an optionally substituted $C_{5-12}$ aryl or an optionally substituted $C_{5-12}$ heteroaryl;
L is a linker having at least 4 atoms;
$R^1$ is H or alkyl;
and a pharmaceutically acceptable salt, pharmaceutically acceptable N-oxide, pharmaceutically active metabolite, pharmaceutically acceptable prodrug, pharmaceutically acceptable solvate thereof. In another embodiment, the histone deacetylase inhibitor has the structure of Formula (I):

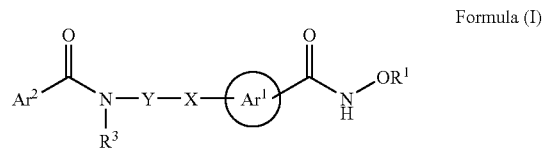

Formula (I)

wherein:

R¹ is hydrogen or alkyl;

X is —O—, —NR²—, or —S(O)$_n$ where n is 0-2 and R² is hydrogen or alkyl;

Y is alkylene optionally substituted with cycloalkyl, optionally substituted phenyl, alkylthio, alkylsulfinyl, alkysulfonyl, optionally substituted phenylalkylthio, optionally substituted phenylalkylsulfonyl, hydroxy, or optionally substituted phenoxy;

Ar¹ is phenylene or heteroarylene wherein said Ar¹ is optionally substituted with one or two groups independently selected from alkyl, halo, hydroxy, alkoxy, haloalkoxy, or haloalkyl;

R³ is hydrogen, alkyl, hydroxyalkyl, or optionally substituted phenyl; and

Ar² is aryl, aralkyl, aralkenyl, heteroaryl, heteroaralkyl, heteroaralkenyl, cycloalkyl, cycloalkylalkyl, heterocycloalkyl, or heterocycloalkylalkyl;

and individual stereoisomers, individual geometric isomers, or mixtures thereof; or a pharmaceutically acceptable salt thereof.

In another embodiment, the histone deacetylase inhibitor has the structure of a compound of Formula (A), (B), (C), or (D) or it's pharmaceutically acceptable salt thereof. In a further embodiment, the histone deacetylase inhibitor is 3-((dimethylamino)methyl)-N-(2-(4-(hydroxycarbamoyl)phenoxy)ethyl)benzofuran-2-carboxamide.

In one aspect is a method for treating diseases, disorders, or conditions associated with overexpression of homologous recombination of DNA or wherein the pathogenesis involves homologous recombination of DNA, comprising: a) administering to the patient having a disease, disorder, or condition associated with overexpression of homologous recombination of DNA or wherein the pathogenesis involves homologous recombination of DNA, a therapeutically effective amount of at least one agent that modulates the activity of BRCA1 or disrupts the interaction of BRCA1 and RAD51, or disrupts the assembly of a functional repair complex for homologous recombination for which BRCA1 is implicated; and b) administering to the patient a treatment capable of damaging cellular DNA.

In another embodiment, the agent disrupts the assembly of a functional repair complex for homologous recombination of DNA. In another embodiment, the agent that modulates the activity of BRCA1 reduces cellular levels of BRCA1.

In another embodiment, the agent that disrupts the assembly of a functional repair complex for homologous recombination of DNA is a therapeutically effective amount of at least one histone deacetylase inhibitor, or its pharmaceutically acceptable derivative. In another embodiment, the disease, disorder, or condition is cancer. In another embodiment, the disease, disorder, or condition is breast cancer, ovarian cancer, or prostate cancer. In another embodiment, the DNA damaging agent is administered when the expression of BRCA1 is within a predetermined range. In another embodiment, the therapeutically effective amount of the at least one histone deacetylase inhibitor is from about 0.2 mg to about 2000 mg.

In another embodiment, the treatment capable of damaging cellular DNA comprises radiotherapy, or administration of a pharmaceutically effective amount of at least one anticancer agent, a known combination scheme for cancer therapy, or any combination thereof. In another embodiment, the treatment capable of damaging cellular DNA is radiotherapy or an administration of a pharmaceutically effective amount of at least one agent selected from the group consisting of topoisomerase inhibitors, tubulin interactors, DNA-interactive agents, DNA-alkylating agents, and platinum complexes.

In another embodiment, the treatment capable of damaging cellular DNA comprises radiotherapy. In another embodiment, the anticancer agent comprises cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, biphosphonates or any combination thereof.

HDAC and HDAC Inhibitors

In eukaryotic cells, genomic DNA in chromatin associates with histones to form nucleosomes. Each nucleosome consists of a protein octamer made up of two copies of each histones H2A, H2B, H3 and H4. DNA winds around this protein core, with the basic amino acids of the histones interacting with the negatively charged phosphate groups of the DNA. The most common posttranslational modification of these core histones is the reversible acetylation of the ε-amino groups of conserved, highly basic N-terminal lysine residues. Reversible acetylation of histones is a major regulator of gene expression that acts by altering accessibility of transcription factors to DNA. In normal cells, histone deacetylases (HDAC) and histone acetyltransferases (HAT) together control the level of acetylation of histones to maintain a balance. Inhibition of HDAC results in the accumulation of hyperacetylated histones, which results in a variety of cellular responses.

Histone acetylation and deacetylation has long been linked to transcriptional control. In some embodiments, HDAC inhibitors, including trichostatin A, sodium butyrate, suberoylanilide hydroxamic acid (SAHA), depsipeptide, MS-275, and aphicidin, among others, promote histone acetylation, resulting in relaxation of the chromatin structure. Chromatin relaxation and uncoiling permits and enhances the expression of diverse genes, including those involved in the differentiation process, e.g. p21$^{CIP1}$. In fact, HDIs, e.g. SAHA, sodium butyrate, have been shown to induce maturation in various human leukemia cell lines. Surprisingly, RAD51 expression level is down regulated rather than enhanced after HDAC inhibitor treatment.

Mammalian HDACs are divided into three major classes based on their structural or sequence homologies to the three distinct yeast HDACs: Rpd3 (class I), Hda1 (class II), and Sir2/Hst (class III). The Rpd3 homologous class I includes HDACs 1, 2, 3, 8, and 11; the Hda1 homologous class II includes HDACs 4, 5, 6, 7, 9 (9a and 9b), and 10; the Sir2/Hst homologous class III SIR T1, 2, 3, 4, 5, 6, and 7. Recent studies revealed an additional family of cellular factors that possesses intrinsic HAT or HDAC activities. These appear to be non-histone proteins that participate in regulation of the cell cycle, DNA repair, and transcription. A number of transcriptional coactivators, including but not limited to p400AF, BRCA2, and ATM-like proteins, function as HAT's. Some transcriptional repressors exhibit HDAC activities in the context of chromatin by recruiting a common chromatin-modifying complex. For instance, the Mas protein family (Mas1, Mxi1, Mad3, and Mad4) comprises a basic-helix-loop-helix-loop-helix-zipper class of transcriptional factors that heterodimerize with Max at their DNA binding sites. Mad:Max heterodimers act as transcriptional repressors at their DNA binding sites through recruitment of "repressor complexes." Mutations that prevent interaction with either Max or the msin3 corepressor complex fail to arrest cell growth. Accordingly, HDAC inhibitor used herein refers to any agent capable of inhibiting the HDAC activity from any of the proteins described above.

As used herein, the terms "histone deacetylase" and "HDAC" refer to any one of a family of enzymes that remove acetyl groups from the s-amino groups of lysine residues at the N-terminus of a histone. Unless otherwise indicated by context, the term "histone" is meant to refer to any histone protein, including H1, H2A, H2B, H3, H4, and H5, from any species. Human HDAC proteins or gene products, include, but are not limited to, HDAC-1, HDAC-2, HDAC-3, HDAC4, HDAC-5, HDAC-6, HDAC-7, HDAC-8, HDAC-9, HDAC-10, and HDAC-11. In some embodiments, the HDAC is also derived from a protozoal or fungal source.

Inhibitors of HDAC have been studied for their therapeutic effects on cancer cells. For example, butyric acid and its derivatives, including sodium phenylbutyrate, have been reported to induce apoptosis in vitro in human colon carcinoma, leukemia and retinoblastoma cell lines. However, butyric acid and its derivatives are not useful pharmacological agents because they tend to be metabolized rapidly and have a very short half-life in vivo. Other inhibitors of HDAC that have been widely studied for their anti-cancer activities are trichostatin A and trapoxin.

The terms "histone deacetylase inhibitor," "inhibitor of histone deacetylase," "HDAC inhibitor," and "inhibitor of HDAC" are used interchangeably to identify a compound, which is capable of interacting with a HDAC and inhibiting its activity, more particularly its enzymatic activity. Inhibiting HDAC enzymatic activity means reducing the ability of a HDAC to remove an acetyl group from a histone. In some embodiments, such inhibition is specific, i.e. the HDAC inhibitor reduces the ability of a HDAC to remove an acetyl group from a histone at a concentration that is lower than the concentration of the inhibitor that is required to produce some other, unrelated biological effect.

HDAC inhibitors include, but not limited to, (1) short-chain fatty acids for example butyrate, 4-phenylbutyrate or valproic acid; (2) hydroxamic acids for example suberoylanilide hydroxamic acid (SAHA), biaryl hydroxamate A-161906, bicyclic aryl-N-hydroxycarboxamides, CG-1521, PXD-101, sulfonamide hydroxamic acid, LAQ-824, oxamflatin, scriptaid, m-carboxy cinnamic acid bishydroxamic acid, trapoxin-hydroxamic acid analogue, trichostatins like trichostatin A (TSA), m-carboxycinnamic acid bis-hydroxamideoxamflatin (CBHA), ABHA, Scriptaid, pyroxamide, and propenamides; (3) epoxyketone-containing cyclic tetrapeptides for example trapoxins, apidicin, depsipeptide, HC-toxin, chlamydocin, diheteropeptin, WF-3161, Cyl-1 and Cyl-2; (4) benzamides or non-epoxyketone-containing cyclic tetrapeptides for example FR901228; apicidin, cyclic-hydroxamic-acid-containing peptides (CHAPs), benzamides, MS-275 (MS-27-275), and CI-994; (5) depudecin; (6) PXD101; and (7) organosulfur compounds. Additional examples of HDAC inhibitors include TSA, TPXA and B, oxamflatin, FR901228 (FK228), trapoxin B, CHAP1, aroyl-pyrrolylhydroxy-amides (APHAs), apicidin, and depudecin.

In some embodiments, the HDAC inhibitor is a reversible inhibitor and is administered for a period prior to and/or during the administration of radiation and/or chemotherapy, and optionally continuing for a period after radiation and/or chemotherapy. In some embodiments, the HDAC inhibitor is chosen from among the compounds selected from the group consisting of trichostatin A, FR, M344, SAHA, combinations thereof, and the like. Methods for determining HDAC activity in vivo or in vitro are known.

In some embodiments, HDAC inhibitors are used in combination therapy with chemical agents that are understood to mimic the effects of radiotherapy and/or that function by direct contact with DNA, such as, for example, DNA alkylating agents. In some embodiments, agents for use in combination with HDAC inhibitors in methods provided include cisplatinum, adriamycin (Doxirubicin), topoisomerase inhibitors (Etoposide), 5-FU, and taxol.

According to this aspect, HDAC inhibitors are used synergistically at effective amounts that result in concentrations in the fluid of a target tissue that are less than about twice the $IC_{50}$ concentration for the particular compound. In some embodiments, the effective amount is about equal to the $IC_{50}$ concentration. In another embodiment, the HDAC inhibitors are administered at lower amounts such as about 50% of the $IC_{50}$ concentration, or less, at the target tissue. Furthermore, in other embodiments, the HDAC inhibitor is administered locally so that the concentration at the target tissue is in the effective range and lower elsewhere.

In some other embodiments, any inhibitor of HDAC that provides a synergistic effect in combination with radiotherapy or chemotherapy is used in accordance with the methods described herein, provided that the inhibitor has acceptably low toxicity to the host.

In some embodiments, the following are desired characteristics of the HDAC inhibitory synergistic agent: high inhibitory activity at low concentrations (such as having an $IC_{50}$ of less than about 800 ng/ml, about 320 ng/ml or less, or about 60 ng/ml or less, i.e. about 5 ng/ml), reversible HDAC inhibition, low toxicity at synergistic doses, rapid clearance following termination of administration. An acceptable combination of these characteristics includes compromises in one or more categories; however the advantages of the methods and pharmaceutical compositions described are best achieved in the combination of these characteristics.

In some embodiments, the methods provided herein comprise adding at least one compound having the structure of Formula (A) or Formula (I) to a cell or a patient, and determining the effect on (1) inhibiting activity of RAD51, (2) disrupting the formation of RAD51 foci, (3) disrupting the assembly of a functional repair complex for homologous recombination of DNA, (4) DSB repair, (5) homologous recombination, (6) sensitivity to ionizing radiation, and/or (7) class switch recombination.

Representative Compounds

Selected compounds for use in the compositions and methods described herein are provided in Tables I-IV. Compounds of Formula (I) where $R^1$ and $R^3$ are hydrogen, $Ar^1$ is phenyl and $Ar^2$ and Y:

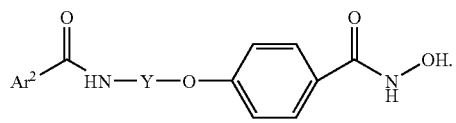

Compounds of Formula (I) where $R^1$ is hydrogen, $Ar^1$ is phenyl and $R^3$, $Ar^2$ and Y:

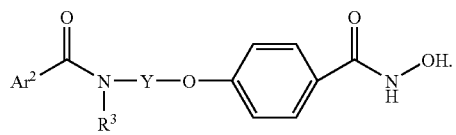

Compounds of Formula (I) where $R^1$ and $R^3$ are hydrogen, $Ar^1$ is phenyl, $Ar^2$ and Y are as defined in Table I below are:

TABLE III

| Compound No. | Z | R | Y |
|---|---|---|---|
| 198 | S | H | —CH$_2$—CH$_2$— |
| 199 | O | H | —CH$_2$—CH$_2$— |
| 200 | NH | H | —CH$_2$—CH$_2$— |
| 201 | NMe | H | —CH$_2$—CH$_2$— |
| 202 | S | H | —CH$_2$—CH$_2$—CH$_2$— |
| 203 | O | H | —CH$_2$—CH$_2$—CH$_2$— |
| 204 | S | H | —(S)—CH(i-propyl)-CH$_2$— |
| 205 | S | H | —(S)—CH(ethyl)-CH$_2$— |
| 206 | S | H | —(S)—CH(methyl)-CH$_2$— |
| 207 | S | H | —(R)—CH(methyl)-CH$_2$— |
| 208 | O | H | —(S)—CH(ethyl)-CH$_2$— |
| 209 | S | H | —(R)—CH$_2$—CH(CH$_3$)— |
| 210 | S | H | —(S)—CH$_2$—CH(CH$_3$)— |
| 211 | O | H | —(R)—CH$_2$—CH(CH$_3$)— |
| 212 | S | 6-methoxy | —CH$_2$—CH$_2$— |
| 213 | S | 5-methyl | —CH$_2$—CH$_2$— |
| 214 | S | 3-choloro | —CH$_2$—CH$_2$— |
| 215 | O | 5-methyl | —CH$_2$—CH$_2$— |
| 216 | O | 6-methyl | —CH$_2$—CH$_2$— |
| 217 | S | 4-CF$_3$ | —CH$_2$—CH$_2$— |
| 218 | S | 5-fluoro | —CH$_2$—CH$_2$— |
| 219 | S | 5-methoxy | —CH$_2$—CH$_2$— |
| 220 | O | 5-chloro | —CH$_2$—CH$_2$— |
| 221 | O | 7-methoxy | —CH$_2$—CH$_2$— |
| 222 | O | 5-methoxy | —CH$_2$—CH$_2$— |
| 223 | O | 5-(2-methoxyethoxy)- | —CH$_2$—CH$_2$— |
| 224 | O | 5-(2-morpholin-4-ylethoxy)- | —CH$_2$—CH$_2$— |
| 225 | O | 5-pyridin-3-ylmethoxy | —CH$_2$—CH$_2$— |
| 226 | O | 3-methyl | —CH$_2$—CH$_2$— |
| 227 | S | 3 methyl | —CH$_2$—CH$_2$— |
| 228 | O | 5-(2-hydroxyethoxy)- | —CH$_2$—CH$_2$— |
| 229 | O | 5-(2-N,N-dimethylaminoethoxy)- | —CH$_2$—CH$_2$— |
| 230 | O | 6-CH$_3$OCH$_2$CH$_2$O | —CH$_2$—CH$_2$— |
| 231 | O | 6-(2-morpholin-4-ylethoxy)- | —CH$_2$—CH$_2$— |
| 232 | O | 6-pyridin-3ylmethoxy- | —CH$_2$—CH$_2$— |
| 233 | O | 3-ethyl | —CH$_2$—CH$_2$— |
| 234 | NH | 5-fluoro | —CH$_2$—CH$_2$— |
| 235 | NH | 5-methoxy | —CH$_2$—CH$_2$— |
| 236 | O | 3-CH$_3$OCH$_2$ | —CH$_2$—CH$_2$— |
| 237 | O | 3-phenoxymethyl | —CH$_2$—CH$_2$— |
| 238 | NH | 5,6-dimethoxy | —CH$_2$—CH$_2$— |
| 239 | O | 3-morpholino-4-ylmethyl | —CH$_2$—CH$_2$— |
| 240 | O | 3-N,N-dimethylaminomethyl | —CH$_2$—CH$_2$— |
| 241 | O | 3-i-propoxymethyl | —CH$_2$—CH$_2$— |
| 242 | O | 7-phenoxymethyl | —CH$_2$—CH$_2$— |
| 243 | O | 7-CH$_3$OCH$_2$ | —CH$_2$—CH$_2$— |
| 244 | O | 7-morpholino-4-ylmethyl | —CH$_2$—CH$_2$— |
| 245 | O | 7-N,N-dimethylaminomethyl | —CH$_2$—CH$_2$— |
| 246 | S | 5-methyl | —CH$_2$—CH$_2$—CH$_2$— |
| 247 | S | 6-methoxy | —CH$_2$—CH$_2$—CH$_2$— |
| 248 | O | 7-CH$_3$OCH$_2$ | —CH$_2$—CH$_2$—CH$_2$— |
| 249 | O | 7-phenoxymethyl | —CH$_2$—CH$_2$—CH$_2$— |
| 250 | O | 5-CH$_3$OCH$_2$CH$_2$O | —(R)—CH$_2$—CH(CH$_3$) |
| 251 | O | H | (R)—CH(CH$_3$Smethyl)-CH$_2$— |
| 252 | O | H | (R)—CH(CH$_3$SO$_2$-methyl)-CH$_2$— |
| 253 | O | 3-(2-phenylethyl)- | —CH$_2$—CH$_2$— |
| 254 | O | 3-(N-methyl-N-benzylaminomethyl)- | —CH$_2$—CH$_2$— |
| 255 | O | 3-(N-methyl-N-2-phenylethyl-aminomethyl)- | —CH$_2$—CH$_2$— |
| 256 | O | 3-(3-hydroxypropylthiomethyl)- | —CH$_2$—CH$_2$— |
| 257 | O | 3-(3-hydroxypropylsylfinylmethyl)- | —CH$_2$—CH$_2$— |
| 258 | O | 3-(3-hydroxypropylsylfinylmethyl)- | —CH$_2$—CH$_2$— |
| 259 | O | 3-(N-methyl-N-2-indol-3-yl-ethylaminomethyl)- | —CH$_2$—CH$_2$— |

TABLE III-continued

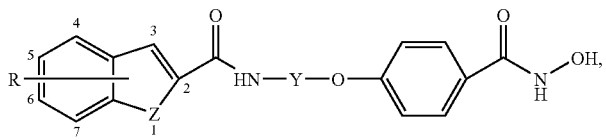

| Compound No. | Z | R | Y |
|---|---|---|---|
| 260 | O | 3-[2-(3-trifluoromethyl-phenyl)-ethyl]- | —CH₂—CH₂— |
| 261 | O | 3-[2-(3-trifluoromethoxy-phenyl)-ethyl]- | —CH₂—CH₂— |
| 262 | O | 3-(N-hydroxyaminocarbonyl-methylaminomethyl)- | —CH₂—CH₂— |
| 263 | O | 3-(2-carboxyethylamino-methyl)- | —CH₂—CH₂— |
| 264 | O | H | (RS)—CH₂CH-(phenoxymethyl)- |
| 265 | O | 3-(3-hydroxypropyloxymethyl)- | —CH₂—CH₂— |
| 266 | O | 3-(2-fluorophenoxymethyl)- | —CH₂—CH₂— |
| 267 | O | 3-(3-fluorophenoxymethyl)- | —CH₂—CH₂— |
| 268 | O | 3-(4-fluorophenoxymethyl)- | —CH₂—CH₂— |
| 269 | O | 3-(2-methoxyethyloxymethyl)- | —CH₂—CH₂— |
| 270 | O | 3-(pyridin-4-yloxymethyl)- | —CH₂—CH₂— |
| 271 | O | 3-(2,4,6-trifluorophenoxymethyl)- | —CH₂—CH₂— |
| 272 | O | 3-(2-oxopyridin-1-ylmethyl)- | —CH₂—CH₂— |
| 273 | O | 3-(2,2,2-trifluoroethoxymethyl)- | —CH₂—CH₂— |
| 274 | O | 3-(4-imidazol-1-ylphenoxymethyl)- | —CH₂—CH₂— |
| 275 | O | 3-(4-[1.2.4]-triazin-1-yl-phenoxy-methyl)- | —CH₂—CH₂— |
| 276 | O | 3-(pyrrolidin-1-ylmethyl)- | —CH₂—CH₂— |
| 277 | O | 3-(piperidin-1-ylmethyl)- | —CH₂—CH₂— |
| 278 | O | 3-(4-trifluoromethylpiperidin-ylmethyl)- | —CH₂—CH₂— |
| 279 | O | 3-(4-methylpiperazin-1-yl-methyl)- | —CH₂—CH₂— |
| 280 | O | 3-(3,3,3-trifluoropropyloxy-methyl)- | —CH₂—CH₂— |
| 281 | O | 4-methyl | —CH₂—CH₂— |
| 282 | O | 3-(4-fluorophenyithiomethyl)- | —CH₂—CH₂— |
| 283 | O | 3-(4-fluorophenylsulfinyl-methyl)- | —CH₂—CH₂— |
| 284 | O | 3-(4-fluorophenylsulfonyl-methyl)- | —CH₂—CH₂— |
| 285 | O | 3-(2,2,2-trifluoroethoxy-methyl)- | (S)—CH(ethyl)-CH₂— |
| 286 | O | 4-hydroxy | —CH₂—CH₂— |
| 287 | O | 5-chloro | (S)—CH(ethyl)-CH₂— |
| 288 | O | 5-chloro | (R)—CH₂—CH(methyl)- |
| 289 | O | 4-pyridin-3-ylmethyloxy-methyl | —CH₂—CH₂— |
| 290 | O | 4-methoxy | —CH₂—CH₂— |
| 291 | O | 4-(2-methoxyethyloxy)- | —CH₂—CH₂— |
| 292 | O | 4-pyridin-3-ylmethyloxy | —CH₂—CH₂— |
| 293 | NH | 4-methoxy | —CH₂—CH₂— |
| 294 | O | 3-(2-methoxyethyloxymethyl)- | (S)—CH(ethyl)-CH₂— |
| 295 | O | 3-(2-methoxyethyloxymethyl)- | (R)—CH₂—CH(methyl)- |
| 296 | O | 3-N,N-diethylaminomethyl | —CH₂—CH₂— |
| 297 | O | 5-(2-methoxyethyloxy)- | (S)—CH(ethyl)-CH₂— |
| 298 | O | 5-tetrahydropyran-4-yloxy | —CH₂—CH₂— |
| 299 | O | 5-tetrahydropyran-4-yloxy | (S)—CH(ethyl)-CH₂— |
| 300 | O | 5-tetrahydropyran-4-yloxy | (R)—CH₂—CH(methyl)- |
| 301 | O | 5-(2,2,2-trifluoroethyloxy)- | —CH₂—CH₂— |
| 302 | O | 5-(2-pyrrolidin-1-ylethyloxy)- | —CH₂—CH₂— |
| 303 | O | 5-(2-pyrrolidin-1-ylethyloxy)- | (S)—CH(ethyl)-CH₂— |
| 304 | O | 5-(2-pyrrolidin-1-ylethyloxy)- | (R)—CH₂—CH(methyl)- |
| 305 | O | 5-(piperidin-4-yloxy)- | —CH₂—CH₂— |
| 306 | O | H | (S)—CH(2-CH₃Sethyl)-CH₂— |
| 307 | O | H | (S)—CH(2-CH₃SO₂ethyl)-CH₂— | and are named as: N-hydroxy-4-[2-(benzothiophen-2-ylcarbonylamino)ethoxy]-benzamide; N-hydroxy-4-[2-(benzofuran-2-ylcarbonylamino)ethoxy]-benzamide; N-hydroxy-4-[2-(1H-indol-2-ylcarbonylamino)ethoxy]-benzamide; N-hydroxy-4-[2-(1-methylindol-2-ylcarbonylamino)ethoxy]-benzamide; N-hydroxy-4-[3-(benzothiophen-2-ylcarbonylamino)propoxy]-benzamide; N-hydroxy-4-[3-(benzofuran-2-ylcarbonylamino)propoxy]-benzamide; N-hydroxy-4-[2S-(benzothiophen-2-ylcarbonylamino)-3-methylbutoxy]-benzamide; N-hydroxy-4-[2S-(benzothiophen-2-ylcarbonylamino)butoxy]-benzamide; N-hydroxy-4-[2S-(benzothiophen-2-ylcarbonylamino)-propoxy]-benzamide; N-hydroxy-4-[2R-(benzothiophen-2-ylcarbonylamino)-propoxy]-benzamide; N-hydroxy-4-[2S-(benzofuran-2-ylcarbonylamino)butoxy]-benzamide; N-hydroxy-4-[2-(benzothiophen-2-ylcarbonylamino)-1R-methylethoxy]-benzamide; N-hydroxy-4-[2-(benzothiophen-2-ylcarbonylamino)-1S-methylethoxy]-benzamide; N-hydroxy-4-[2-(benzofuran-2-ylcarbonylamino)-1R-methylethoxy]-benzamide; N-hydroxy-4-[2-(6-methoxybenzothiophen-2-ylcarbonylamino)ethoxy]-benzamide; N-hydroxy-4-[2-(5-methylbenzothiophen-2-ylcarbonylamino)ethoxy]-benzamide; N-hydroxy-4-[2-(3-chlorobenzothiophen-2-ylcarbonylamino)ethoxy]-benzamide; N-hydroxy-4-[2-(5-methylbenzofuran-2-ylcarbonylamino)ethoxy]-benzamide; N-hydroxy-4-[2-(6-methylbenzofuran-2-ylcarbonylamino)ethoxy]-benzamide; N-hydroxy-4-[2-(4-trifluoromethylbenzothiophen-2- ylcarbonylamino)ethoxy]-benzamide; N-hydroxy-4-[2-(5-fluorobenzothiophen-2-ylcarbonylamino)ethoxy]-benzamide; N-hydroxy-4-[2-(5-methoxybenzothiophen-2-ylcarbonylamino)ethoxy]-benzamide; N-hydroxy-4-[2-(5-chlorobenzofuran-2-ylcarbonylamino)ethoxy]-benzamide; N-hydroxy-4-[2-(7-methoxybenzofuran-2-ylcarbonylamino)ethoxy]-benzamide; N-hydroxy-4-[2-(5-methoxybenzofuran-2-ylcarbonylamino)ethoxy]-benzamide; N-hydroxy-4-{2-[5-(2-methoxyethoxy)benzofuran-2-ylcarbonylamino]ethoxy}-benzamide; N-hydroxy-4-{2-[5-(2-morpholin-4-ylethoxy)benzofuran-2-ylcarbonylamino]ethoxy}-benzamide; N-hydroxy-4-{2-[5-(pyridin-3-ylmethoxy)benzofuran-2-ylcarbonylamino]ethoxy}-benzamide; N-hydroxy-4-[2-(3-methylbenzofuran-2-ylcarbonylamino)ethoxy]-benzamide; N-hydroxy-4-[2-(3-methylbenzothiophen-2-ylcarbonylamino)ethoxy]-benzamide; N-hydroxy-4-{2-[5-(2-hydroxyethoxy)benzofuran-2-ylcarbonylamino]ethoxy}benzamide; N-hydroxy-4-{2-[5-(2-N,N-dimethylaminoethoxy)benzofuran-2-ylcarbonylamino]-ethoxy}-benzamide; N-hydroxy-4-{2-[6-(2-methoxyethoxy)benzofuran-2-ylcarbonylamino]ethoxy}-benzamide; N-hydroxy-4-{2-[6-(2-morpholin-4-ylethoxy)benzofuran-2-ylcarbonylamino]ethoxy}-benzamide; N-hydroxy-4-{2-[6-(pyridin-3-ylmethoxy)benzofuran-2-ylcarbonylamino]ethoxy}-benzamide; N-hydroxy-4-[2-(3-ethylbenzofuran-2-ylcarbonylamino)ethoxy]-benzamide; N-hydroxy-4-[2-(5-fluoroindol-2-ylcarbonylamino)ethoxy]-benzamide; N-hydroxy-4-[2-(5-methoxyindol-2-ylcarbonylamino)ethoxy]-benzamide; N-hydroxy-4-{2-[3-(methoxymethyl)benzofuran-2-ylcarbonylamino]ethoxy}benzamide; N-hydroxy-4-{2-[3-(phenoxymethyl)benzofuran-2-ylcarbonylamino]ethoxy}benzamide; N-hydroxy-4-[2-(5,6-dimethoxyindol-2-ylcarbonylamino)ethoxy]-benzamide; N-hydroxy-4-{2-[3-(morpholin-4-ylmethyl)benzofuran-2-ylcarbonylamino]ethoxy-benzamide; N-hydroxy-4-{2-[3-(N,N-dimethylaminomethyl)benzofuran-2-ylcarbonylamino]ethoxy}-benzamide; N-hydroxy-4-{2-[3-(i-propoxymethyl)benzofuran-2-ylcarbonylamino]ethoxy}benzamide; N-hydroxy-4-{2-[7-(phenoxymethyl)benzofuran-2-ylcarbonylamino]ethoxy}benzamide; N-hydroxy-4-{2-[7-(methoxymethyl)benzofuran-2-ylcarbonylamino]ethoxy}benzamide; N-hydroxy-4-{2-[7-(morpholin-4-ylmethyl)benzofuran-2-ylcarbonylamino]ethoxy}-benzamide; N-hydroxy-4-{2-[7-(N,N-dimethylaminomethyl)benzofuran-2-ylcarbonylamino]ethoxy}-benzamide; N-hydroxy-4-{3-[5-(methyl)benzothiophen-2-ylcarbonylamino]propoxy}-benzamide; N-hydroxy-4-{3-[6-(methoxy)benzothiophen-2-ylcarbonylamino]propoxy}-benzamide; N-hydroxy-4-{3-[7-(methoxymethyl)benzofuran-2-ylcarbonylamino]propoxy}-benzamide; N-hydroxy-4-{3-[7-(phenoxymethyl)benzofuran-2-ylcarbonylamino]propoxy}-benzamide; N-hydroxy-4-{2-[5-(2-methoxyethoxy)benzofuran-2-ylcarbonylamino]-1R-methylethoxy}benzamide; N-hydroxy-4-(2R-benzofuran-2-ylcarbonylamino-3-methylthiopropoxy)benzamide; N-hydroxy-4-(2R-benzofuran-2-ylcarbonylamino-3-methylsulfonylpropoxy)benzamide; N-hydroxy-4-{2-[3-(2-phenylethyl)benzofuran-2-ylcarbonylamino]ethoxy}benzamide; N-hydroxy-4-{2-[3-(N-methyl-N-benzylaminomethyl)benzofuran-2-ylcarbonylamino]-ethoxy}benzamide; N-hydroxy-4-{2-[3-(N-methyl-N-2-phenylethylaminomethyl)benzofuran-2-ylcarbonylamino]-ethoxy}benzamide; N-hydroxy-4-{2-[3-(3-hydroxypropylthiomethyl)benzofuran-2-ylcarbonylamino]-ethoxy}benzamide; N-hydroxy-4-{2-[3-(3-hydroxypropylsulfinylmethyl)benzofuran-2-ylcarbonylamino]-ethoxybenzamide; N-hydroxy-4-{2-[3-(3-hydroxypropylsulfonylmethyl)benzofuran-2-ylcarbonylamino]-ethoxy}benzamide; N-hydroxy-4-{2-[3-(N-methyl-N-2-indol-3-ylethylaminomethyl)benzofuran-2-ylcarbonylamino]-ethoxy}benzamide; N-hydroxy-4-{2-[3-(2-(3-trifluoromethylphenyl)ethyl)benzofuran-2-ylcarbonylamino]-ethoxy}benzamide; N-hydroxy-4-{2-[3-(2-(3-trifluoromethoxyphenyl)ethyl)benzofuran-2-ylcarbonylamino]-ethoxy}benzamide; N-hydroxy-4-{2-[3-(N-hydroxyaminocarbonylmethylaminomethyl)benzofuran-2-ylcarbonylamino]ethoxy}benzamide; N-hydroxy-4-{2-[3-(2-carboxyethylaminomethy)benzofuran-2-ylcarbonylamino]-ethoxy}benzamide; N-hydroxy-4-{2-(benzofuran-2-ylcarbonylamino)-1RS-phenoxymethylethoxy}-benzamide; N-hydroxy-4-{2-[3-(3-hydroxypropoxymethyl)benzofuran-2-ylcarbonylamino]ethoxy}-benzamide; N-hydroxy-4-{2-[3-(2-fluorophenoxymethyl)benzofuran-2-ylcarbonylamino]ethoxy}-benzamide; N-hydroxy-4-{2-[3-(3-fluorophenoxymethyl)benzofuran-2-ylcarbonylamino]ethoxy}-benzamide; N-hydroxy-4-{2-[3-(4-fluorophenoxymethyl)benzofuran-2-ylcarbonylamino]ethoxy}-benzamide; N-hydroxy-4-{2-[3-(2-methoxyethyloxymethyl)benzofuran-2-ylcarbonylamino]ethoxy}-benzamide; N-hydroxy-4-{2-[3-(pyridin-4-yloxymethyl)benzofuran-2-ylcarbonylamino]ethoxy}-benzamide; N-hydroxy-4-{2-[3-(2,4,6-trifluorophenoxymethyl)benzofuran-2-ylcarbonylamino]-ethoxy}benzamide; N-hydroxy-4-{2-[3-(2-oxopyridin-1-ylmethyl)benzofuran-2-ylcarbonylamino]ethoxy}-benzamide; N-hydroxy-4-{2-[3-(2,2,2-trifluoroethoxymethyl)benzofuran-2-ylcarbonylamino]-ethoxy}benzamide; N-hydroxy-4-{2-[3-(4-imidazol-1-ylphenoxymethyl)benzofuran-2-ylcarbonylamino]-ethoxy}benzamide; N-hydroxy-4-{2-[3-(4-[1.2.4]-triazin-1-ylphenoxymethyl)benzofuran-2-ylcarbonyl-amino]ethoxy}benzamide; N-hydroxy-4-{2-[3-(pyrrolidin-1-methyl)benzofuran-2-ylcarbonylamino]ethoxy}-benzamide; N-hydroxy-4-{2-[3-(piperidin-1-methyl)benzofuran-2-ylcarbonylamino]ethoxy}-benzamide; N-hydroxy-4-{2-[3-(4-trifluoromethylpiperidin-1-methyl)benzofuran-2-ylcarbonylamino]-ethoxy}benzamide; N-hydroxy-4-{2-[3-(4-methylpiperazin-1-methyl)benzofuran-2-ylcarbonylamino]-ethoxy}benzamide; N-hydroxy-4-{2-[3-(3,3,3-trifluoropropyloxymethyl)benzofuran-2-ylcarbonylamino]-ethoxy}benzamide; N-hydroxy-4-[2-(4-methylbenzofuran-2-ylcarbonylamino)-ethoxy}benzamide; N-hydroxy-4-{2-[3-(4-fluorophenylthiomethyl)benzofuran-2-ylcarbonyl-amino]-ethoxy}-benzamide; N-hydroxy-4-{2-[3-(4-fluorophenylsulfinylmethyl)benzofuran-2-ylcarbonylamino]-ethoxy}benzamide; N-hydroxy-4-{2-[3-(4-fluorophenylsulfonylmethyl)benzofuran-2-ylcarbonylamino]-ethoxy}benzamide; N-hydroxy-4-{2S-[3-(2,2,2-trifluoroethoxymethyl)benzofuran-2-ylcarbonylamino]-butoxy}benzamide; N-hydroxy-4-[2-(4-hydroxybenzofuran-2-ylcarbonylamino)ethoxy]benzamide; N-hydroxy-4-[2S-(5-chlorobenzofuran-2-ylcarbonylamino)butoxy]benzamide; N-hydroxy-4-[2-(5-chlorobenzofuran-2-ylcarbonylamino]-1R-methylethoxy]benzamide; N-hydroxy-4-[2-(4-pyridin-3-ylmethyloxymethylbenzofuran-2-ylcarbonylamino)-ethoxy]benzamide; N-hydroxy-4-[2-(4-methoxybenzofuran-2-ylcarbonylamino)ethoxy]benzamide; N-hydroxy-4-{2-[4-(2-methoxyethyloxy)benzofuran-2-ylcarbonylamino)ethoxy}-benzamide; N-hydroxy-4-[2-(4-pyridin-3-ylmethyloxybenzofuran-2-ylcarbonylamino-)-ethoxy]benzamide; N-hydroxy-4-[2-(4-methoxyindol-2-ylcarbonylamino)ethoxy]benzamide; N-hydroxy-4-{2S-[3-(2-methoxyethyloxymethyl)benzofuran-2-ylcarbonylamino]-butoxy}benzamide; N-hydroxy-4-{2-[3-

(2-methoxyethyloxymethyl)benzofuran-2-ylcarbonylamino]-1R-methyl -ethoxy}benzamide; N-hydroxy-4-{2-[3-(N,N-diethylaminomethyl)benzofuran-2-ylcarbonylamino]ethoxy}-benzamide; N-hydroxy-4-{2S-[5-(2-methoxyethyloxy)benzofuran-2-ylcarbonylamino]butoxy}-benzamide; N-hydroxy-4-{2-[5-(tetrahydropyran-4-yloxy)benzofuran-2-ylcarbonylamino]ethoxy}-benzamide; N-hydroxy-4-{2S-[5-(tetrahydropyran-4-yloxy)benzofuran-2-ylcarbonylamino]butoxy}-benzamide; N-hydroxy-4-{2-[5-(tetrahydropyran-4-yloxy)benzofuran-2-ylcarbonylamino]-1R-methyl-ethoxy}benzamide; N-hydroxy-4-{2-[5-(2,2,2-trifluoroethyloxy)benzofuran-2-ylcarbonylamino]ethoxy}-benzamide; N-hydroxy-4-{2-[5-(2-pyrrolidin-1-ylethyloxy)benzofuran-2-ylcarbonylamino]ethoxy}-benzamide; N-hydroxy-4-{2S-[5-(2-pyrrolidin-1-ylethyloxy)benzofuran-2-ylcarbonylamino]butoxy}-benzamide; N-hydroxy-4-{2-[5-(2-pyrrolidin-1-ylethyloxy)benzofuran-2-ylcarbonylamino]-1R-methyl-ethoxy}benzamide; N-hydroxy-4-{2-[5-(piperidin-4-yloxy)benzofuran-2-ylcarbonylamino]ethoxy}-benzamide; N-hydroxy-4-[2S-(benzofuran-2-ylcarbonylamino)-4-methylthiobutoxy]benzamide; and N-hydroxy-4-[2S -(benzofuran-2-ylcarbonylamino)-4-methylsulfonylbutoxy]benzamide.

Compounds of Formula (I) where $R^1$ and $R^3$ are hydrogen, $Ar^1$ is isoxazol-5-yl and $Ar^2$ and Y:

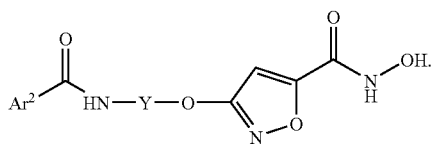

Certain Embodiments

Certain embodiments are described below:
I. Group I of compounds of Formula (I) is that:

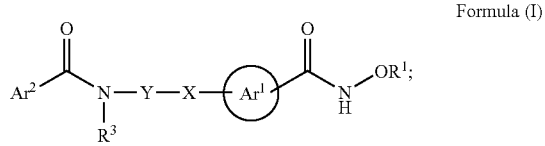

Formula (I)

wherein:
$R^1$ is hydrogen or alkyl;
X is —O—, —$NR^2$—, or —$S(O)_n$— where n is 0-2 and $R^2$ is hydrogen or alkyl;
Y is alkylene optionally substituted with cycloalkyl, optionally substituted phenyl, alkylthio, alkysulfonyl, optionally substituted phenylalkylthio, optionally substituted phenylalkylsulfonyl, or hydroxy;
$Ar^1$ is phenylene or heteroarylene wherein said $Ar^1$ is optionally substituted with one or two groups independently selected from alkyl, halo, hydroxy, alkoxy, haloalkoxy, or haloalkyl;
$R^3$ is hydrogen, alkyl, hydroxyalkyl, or optionally substituted phenyl; and
$Ar^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl.

Within this group I:
(A) A group of compounds is that wherein $R^1$ and $R^3$ are hydrogen, X is —O— and Y is ethylene or n-propylene. In one embodiment, Y is ethylene.
(B) Another group of compounds is that wherein $R^1$ and $R^3$ are hydrogen, X is —O— and Y is —$CH(C_2H_5)CH_2$—, —$CH(i-C_3H_7)CH_2$—, or —$CH(CH_3)CH_2$— and the stereochemistry at the chiral carbon is (S). In one embodiment, Y is —$CH(C_2H_5)CH_2$—.
(C) Yet another group of compounds is that wherein $R^1$ and $R^3$ are hydrogen, X is —O— and Y is —$CH_2CH(CH_3)$— and the stereochemistry at the chiral carbon is (R).
(i) Within the groups (A)-(C), a group of compounds is that wherein $Ar^1$ is phenylene in which the hydroxamate and the X group are para to each other and $Ar^2$ is aryl. In some embodiments, $Ar^2$ is phenyl and is optionally substituted with one or two substituents independently selected from methoxy, ethoxy, phenyl, methyl, tert-butyl, pyrrol-1-yl, cyclohexene-3-oxy, pyridin-3-yl, pyridin-2-yl, benzoylamino, fluoro, chloro, or thiophen-2-ylmethoxy. In some embodiments, $Ar^2$ is phenyl, 4-biphenyl, 3-biphenyl, 4-tert-butylphenyl, 4-pyrrol-1-ylphenyl, 4-(cyclohexene-3-oxy)phenyl, 4-(pyridin-2-yl)phenyl, 4-(pyridin-3-yl)-phenyl, 2,4-difluorophenyl, 3,4-dimethoxyphenyl, 3,5-dimethoxyphenyl, 3,4-difluorophenyl, 2,5-dimethylphenyl, 2,3-dichlorophenyl, 2,3-dimethylphenyl, 4-chloro-2-methoxyphenyl, 3-ethoxyphenyl, 4-methoxy-2-methylphenyl, 3-fluoro-4-methoxyphenyl, 2-thiophen-2-ylmethoxyphenyl, 3-thiophen-2-ylmethoxyphenyl, 2-biphenyl, or 2-pyrrol-1-ylphenyl.

(ii) Within the groups (A)-(C), another group of compounds is that wherein $Ar^1$ is phenylene in which the hydroxamate and the X group are para to each other and $Ar^2$ is trans aryl-CH=CH—. In some embodiments, $Ar^2$ is trans phenyl-CH=CH— and is optionally substituted with alkoxy. In one embodiment, $Ar^2$ is trans phenyl-CH=CH— substituted with methoxy. In one embodiment, $Ar^2$ is trans phenyl-CH=CH—.

(iii) Within the groups (A)-(C), another group of compounds is that wherein $Ar^1$ is phenylene in which the hydroxamate and the X group are para to each other and $Ar^2$ is heteroaryl-CH=CH—. In one embodiment, $Ar^2$ is pyridinyl-CH=CH—. In one embodiment, $Ar^2$ is trans 5-bromothiophen-2-yl-CH=CH— or trans indol-3-yl-CH=CH—.

(iv) Within the groups (A)-(C), another group of compounds is that wherein $Ar^1$ is phenylene in which the hydroxamate and the X group are para to each other and $Ar^2$ is heteroaryl. In some embodiments, $Ar^2$ is pyridin-3-yl, thiophen-2-yl, quinolin-6-yl, thiazol-2-yl, benzthiazol-2-yl, benzoxazol-2-yl, furanyl, pyrrol-2-yl, indol-5-yl, indol-3-yl, indazol-3-yl, quinolin-3-yl, quinolin-1-yl, quinolin-8-yl, benzotriazol-4-yl, benzofuran-5-yl, isoquinolin-1-yl, isoquinolin-3-yl, quinoxalin-2-yl, quinolin-2-yl, or benzimidazol-5-yl wherein said rings are optionally substituted with phenyl, pyridin-4-yl, methyl, methoxy, or dimethylaminomethyl.

(v) Within the groups (A)-(C), another group of compounds is that wherein $Ar^1$ is phenylene in which the hydroxamate and the X group are para to each other and $Ar^2$ is indol-2-yl, benzofuran-2-yl or benzothiophen-2-yl which are optionally substituted with alkyl, alkoxy, halo, haloalkyl, alkoxyalkyloxy, optionally substituted heterocycloalkylalkyloxy, optionally substituted heteroaralkyloxy, hydroxyalkoxy, aminoalkyl, aminoalkyloxy, alkoxyalkyloxy, alkoxyalkyl, optionally substituted phenyloxyalkyl, or optionally substituted heterocycloalkylalkyl. In some embodiments, $Ar^2$ is benzofuran-2-yl or benzothiophen-2-yl wherein benzofuran-2-yl or benzothiophen-2-yl is optionally substituted with methoxy, methyl, chloro, trifluoromethyl, fluoro, 2-methoxyethoxy, 2-morpholin-4-ylethoxy, pyridin-3-ylmethoxy, 2-hydroxyethoxy, 2-N,N-dimethylaminoethoxy, ethyl, methoxymethyl, 2-propyloxymethyl, phenoxymethyl, morpholin-4-ylmethyl, or N,N-dimethylaminomethyl which is located at the 3-position or 5-position. In one embodiment, $Ar^2$ is optionally substituted at the 3-position of the benzothiophen-2-yl or benzofuran-2-yl ring. In one embodiment, $Ar^2$ is benzofuran-2-yl, 3-N,N-dimethylaminomethylbenzofuran-2-yl, or 3-phenoxymethylbenzofuran-2-yl.

(vi) Within the groups (A)-(C), another group of compounds is that wherein $Ar^1$ is phenylene in which the hydroxamate and the X group are para to each other and $Ar^2$ is indol-2-yl, benzofuran-2-yl or benzothiophen-2-yl and is substituted with phenyloxyalkyl, substituted heteroaryloxyalkyl, substituted heterocycloalkyloxyalkyl, or haloalkoxyalkyl which are located at the 3-position of the benzothiophen-2-yl and benzofuran-2-yl rings. In one embodiment, $Ar^2$ is 3-(2,2,2-trifluoroethyloxymethyl)benzofuran-2-yl.

(vii) Within the groups (A)-(C), another group of compounds is that wherein $Ar^1$ is heteroarylene and $Ar^2$ is aryl. In some embodiments, $Ar^1$ is five membered heteroarylene ring containing one, two, or three heteroatoms independently selected from N, O or S. In some embodiments, $Ar^1$ is isoxazolyl where the hydroxamate and the X groups are located at the 5- and 3-position of the isoxazolyl ring, the oxygen atom in the ring being position 1 and $Ar^2$ is aryl. In some embodiments, $Ar^2$ is phenyl that is optionally substituted with one or two substituents independently selected from methoxy, ethoxy, and phenyl optionally substituted with ethoxy or methyl, methyl, tert-butyl, pyrrol-1-yl, cyclohexene-3-oxy, pyridin-3-yl, pyridin-2-yl, benzoylamino, fluoro, chloro, or thiophen-2-ylmethoxy. In some embodiments, $Ar^2$ is phenyl, 4-biphenyl, 3-biphenyl, 2-(2-ethoxyphenyl)phenyl, 3-methylbiphen-4-yl, 4-tert-butylphenyl, 4-pyrrol-1-ylphenyl, 4-(cyclohexene-3-oxy)phenyl, 4-(pyridin-2-yl)phenyl, 4-(pyridin-3-yl)-phenyl, 2,4-difluorophenyl, 3,4-dimethoxyphenyl, 3,5-dimethoxyphenyl, 3,4-difluorophenyl, 2,5-dimethylphenyl, 2,3-dichlorophenyl, 2,3-dimethylphenyl, 4-chloro-2-methoxyphenyl, 3-ethoxyphenyl, 4-methoxy-2-methylphenyl, 3-fluoro-4-methoxyphenyl, 2-thiophen-2-ylmethoxyphenyl, 3-thiophen-2-ylmethoxyphenyl, 2-biphenyl, or 2-pyrrol-1-ylphenyl.

(viii) Within the groups (A)-(C), another group of compounds is that wherein $Ar^1$ is heteroarylene and $Ar^2$ is aryl-CH═CH—. In some embodiments, $Ar^1$ is five membered heteroarylene ring containing one, two, or three heteroatoms independently selected from N, O or S. In some embodiments, $Ar^1$ is isoxazolyl where the hydroxamate and the X groups are located at the 5- and 3-position of the isoxazolyl ring, the oxygen atom in the ring being position 1 and $Ar^2$ is phenyl-CH═CH— and is optionally substituted with alkoxy.

(ix) Within the groups (A)-(C), another group of compounds is that wherein Ar is heteroarylene and $Ar^2$ is heteroaryl-CH═CH—. In some embodiments, $Ar^1$ is five membered heteroarylene ring containing one, two, or three heteroatoms independently selected from N, O or S. In some embodiments, $Ar^1$ is isoxazolyl where the hydroxamate and the X groups are located at the 5- and 3-position of the isoxazolyl ring, the oxygen atom in the ring being position 1 and $Ar^2$ is pyridinyl-CH═CH—.

(x) Within the groups (A)-(C), another group of compounds is that wherein $Ar^1$ is heteroarylene and $Ar^2$ is heteroaryl. In some embodiments, $Ar^1$ is five membered heteroarylene ring containing one, two, or three heteroatoms independently selected from N, O or S. In some embodiments, $Ar^1$ is isoxazolyl where the hydroxamate and the X groups are located at the 5- and 3-position of the isoxazolyl ring, the oxygen atom in the ring being position 1 and $Ar^2$ is pyridin-3-yl, thiophen-2-yl, quinolin-6-yl, thiazol-2-yl, benzthiazol-2-yl, benzoxazol-2-yl, furanyl, pyrrol-2-yl, indol-5-yl, indol-3-yl, indazol-3-yl, quinolin-3-yl, quinolin-8-yl, benzotriazol-4-yl, isoquinolin-1-yl, isoquinolin-3-yl, quinoxalin-2-yl, quinolin-2-yl, or benzimidazol-5-yl wherein said rings are optionally substituted with phenyl, pyridin-4-yl, methyl, methoxy, or dimethylaminomethyl.

(xi) Within the groups (A)-(C), another group of compounds is that wherein $Ar^1$ is heteroarylene and $Ar^2$ is indol-2-yl, benzofuran-2-yl or benzothiophen-2-yl which are optionally substituted with alkyl, alkoxy, halo, haloalkyl, alkoxyalkyloxy, optionally substituted heterocycloalkylalkyloxy, optionally substituted heteroaralkyloxy, hydroxyalkoxy, aminoalkyloxy, alkoxyalkyloxy, alkoxyalkyl, optionally substituted phenyloxyalkyl, or optionally substituted heterocycloalkylalkyl. In some embodiments, $Ar^1$ is a five membered heteroarylene ring containing one, two, or three heteroatoms independently selected from N, O or S. In some embodiments, $Ar^1$ is isoxazolyl where the hydroxamate and the X groups are located at the 5- and 3-position of the isoxazolyl ring, the oxygen atom in the ring being position 1 and $Ar^2$ is benzofuran-2-yl and benzothiophen-2-yl which are optionally substituted with methoxy, methyl, chloro, trifluoromethyl, fluoro, 2-methoxyethoxy, 2-morpholin-4-ylethoxy, pyridin-3-ylmethoxy, 2-hydroxyethoxy, 2-N,N-dimethylaminoethoxy, ethyl, methoxymethyl, phenoxymethyl, morpholin-4-ylmethyl, or dimethylaminomethyl and are located at the 3-position of the benzothiophen-2-yl and benzofuran-2-yl rings. In one embodiment, $Ar^2$ is benzofuran-2-yl or 3-phenoxymethylbenzofuran-2-yl.

(xii) Within the groups (A) and (B), another group of compounds is that wherein $Ar^2$ is substituted with alkoxyalkyloxy, optionally substituted heterocycloalkylalkyloxy, hydroxyalkoxy, aminoalkyloxy, alkoxyalkyloxy, alkoxyalkyl, optionally substituted phenyloxyalkyl, optionally substituted heteroaryloxyalkyl, or optionally substituted heterocycloalkylalkyl. Within this group, a group of compounds is that wherein $Ar^1$ and $Ar^2$ are as described in embodiments above.

II. Group II of compounds of Formula (I) is that wherein X is —O— and $R^1$ and $R^3$ are hydrogen.

III. Group III of compounds of Formula (I) is that wherein X is —S(O)$_n$ and $R^1$ and $R^3$ are hydrogen.

Within the above Groups II and III, in some embodiments, Y is alkylene.

Within the above Groups II and III, in some embodiments, Y is alkylene substituted with cycloalkyl, optionally substituted phenyl, alkylthio, alkylsulfinyl, alkysulfonyl, optionally substituted phenylalkylthio, optionally substituted phenylalkylsulfonyl, hydroxyl, or optionally substituted phenoxy.

Within the above Groups II and III, in some embodiments, $Ar^1$ is phenylene.

Within the above Groups II and III, in some embodiments, $Ar^1$ is heteroarylene.

Within the above Groups II and III, in some embodiments, $Ar^1$ is phenylene. In some embodiments, —CONHOH and X groups are at the 1 and 4 position of the phenylene ring.

IV. Group IV of compounds of Formula (I) is that wherein $Ar^1$ is phenylene, X is —O—, $R^1$ and $R^3$ are hydrogen, and —CONHOH and X groups are at the 1 and 4 position of the phenylene ring.

Within the above Group IV, in some embodiments, Y is alkylene.

Within the above Group IV, in some embodiments, Y is alkylene substituted with cycloalkyl, optionally substituted phenyl, alkylthio, alkylsulfinyl, alkysulfonyl, optionally substituted phenylalkylthio, optionally substituted phenylalkylsulfonyl, hydroxyl, or optionally substituted phenoxy.

(i) Within the above Groups II, III, and IV above, and specific groups described therein, in some embodiments, $Ar^2$ is aryl($C_{2-3}$)alkenyl. In some embodiments, $Ar^2$ is represented by the formulae:

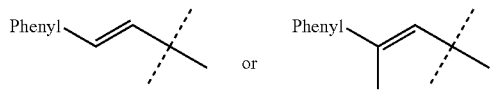

where phenyl is optionally substituted with one or two substituents independently selected from alkyl, alkoxy, methylenedioxy, dialkylamino, or hydroxy. In some embodiments, the substituents are selected from the group consisting of alkyl, alkoxy, methylenedioxy, or hydroxy.

In some embodiments, $Ar^2$ is trans phenyl-CH═CH—, trans 4-MeO-phenyl-CH═CH—, trans 3,4-methylenedioxyphenylCH═CH—, trans 3-hydroxyphenyl-CH═CH—, trans 4-hydroxyphenyl-CH═CH—, trans 2-methoxyphenyl-CH═CH—, trans 3-methoxyphenyl-CH═CH—, trans 3-tolyl-CH═CH—, trans 4-tolyl-CH═CH—, trans 4-dimethylaminophenyl-CH═CH—, trans 2-tolyl-CH═CH—, or trans 2-hydroxyphenyl-CH═CH—.

(ii) Within the above Groups II, III, and IV, and groups described therein, in some embodiments, $Ar^2$ is heteroaryl ($C_{2-3}$)alkenyl. In some embodiments, $Ar^2$ is trans heteroaryl-CH═CH— or trans heteroaryl-C($CH_3$)═CH—. In some embodiments, the heteroaryl ring of $Ar^2$ is pyridinyl, benzofuranyl, thienyl (thiophene), furanyl, or indolyl optionally substituted with one or two substituents selected from hydroxyl, alkoxy, halo, or optionally substituted heterocycloalkoxy.

In some embodiments, $Ar^2$ is trans pyridin-3-yl-CH═CH—, trans 5-hydroxybenzofuran-2-yl-C($CH_3$)═CH—, trans 5-(1-cyclopropylpiperidin-4-yloxy)benzofuran-2-yl-C($CH_3$)═CH—, trans 5-methoxybenzofuran-2-yl-C($CH_3$)═CH—, trans benzofuran-2-yl-CH═CH—, trans 5-bromothiophen-2-yl-CH═CH—, trans furan-3-yl-CH═CH—, trans thiophen-3-yl -CH═CH—, trans thiophen-2-yl-CH═CH—, trans benzofuran-2-yl-C($CH_3$)═CH—, cis benzofuran-2-yl-C($CH_3$)═CH—, trans indol-3-yl-CH═CH—, trans 7-methoxybenzofuran-2-yl-CH═CH—, trans 5-methoxybenzofuran-2-yl-C($CH_3$)═CH—, or trans furan-2-yl-CH═CH.

(iii) Within the above Groups II, III, and IV, and groups described therein, in some embodiments, $Ar^2$ is aryl. In some embodiments, the substituents on the aryl ring are independently selected from optionally substituted phenyl, alkyl, alkoxy, halo, optionally substituted heteroaryl, optionally substituted cycloalkenyloxy, optionally substituted heteroaralkyloxy, optionally substituted heterocycloalkyl, optionally substituted phenylcarbonylamino, or methylenedioxy. In some embodiments, $Ar^2$ is phenyl, 4-biphenyl, 3-biphenyl, 4-tert-butylphenyl, 4-pyrrol-1-ylphenyl, 4-(pyridin-3-yl)phenyl, 4-(pyridin-2-yl)phenyl, 4-(benzoylamino) phenyl, 2,4-difluorophenyl, 3,4-methylenedioxyphenyl, 3,4-dimethoxyphenyl, 3,5-dimethoxyphenyl, 3,4-difluorophenyl, 2,5-dimethylphenyl, 2,3-dichlorophenyl, 2,3-dimethylphenyl, 4-chloro-2-methoxyphenyl, 3-ethoxyphenyl, 4-methoxy-2-methylphenyl, 3-fluoro -4-methoxyphenyl, 2-(thiophen-2-ylmethoxy)phenyl, 3-(thiophen-2-ylmethoxy)-phenyl, 2-biphenyl, naphth-1-yl, 2-pyrrol -1-yl-phenyl, 4-fluoronaphth-1-yl, 3-MeO-naphth-2-yl, 2-MeO-naphth-1-yl, naphth-2-yl, 4-(2-pyridin-4-ylthiazol-5-yl) phenyl, 4-[2-(4-methylpiperazin-1-yl)thiazol-5-yl]-phenyl, 4-(2-pyridin-4-ylaminothiazol-5-yl)phenyl, 4-(4-methylpiperazin-1-yl)phenyl, 4-(4-hydroxypiperidin-1-yl)phenyl, 4-(4-morpholin-4-ylmethylthiazol-2-yl)phenyl, 4-[2-(4-methylpiperazin-1-ylmethyl)thiazol-5-yl]phenyl, 1-methoxynaphth-2-yl, 3'-(2-hydroxyethyl)biphen-4-yl, 3'-(2-hydroxyethyl)biphen-3-yl, 2'-(2-hydroxyethyl)biphen-4-yl, 2'-(2-hydroxyethyl)biphen-3-yl, or 4-[2-(2-morpholin-4-yl -ethyl)thiazol-2-yl]phenyl.

(iv) Within the above Groups II, III, and IV, and groups described therein, in some embodiments, $Ar^2$ is heteroaryl. In some embodiments, $Ar^2$ is heteroaryl optionally substituted with one or two substituents independently selected from alkyl, halo, haloalkyl, alkoxy, alkoxyalkyl, hydroxyalkoxy, hydroxyalkoxyalkyl, alkoxyalkyloxy, alkoxyalkyloxyalkyl, aminoalkyl, aminoalkoxy, haloalkoxy, haloalkoxyalkyl, optionally substituted phenylalkyl, optionally substituted phenyloxyalkyl, optionally substituted heteroaryl, optionally substituted heteroaralkyloxy, optionally substituted heteroaryloxyalkyl, optionally substituted heterocycloalkylalkyl, optionally substituted heterocycloalkyloxy, optionally substituted heterocycloalkylalkyloxy, -alkylene-S(O)$_n$R$^a$ (where n is 0 to 2 and R$^a$ is hydroxyalkyl or optionally substituted phenyl), -alkylene-NR$^e$-alkyleneCONR$^c$R$^d$ (where R$^c$ is hydroxyl and R$^d$ and R$^e$ are independently hydrogen or alkyl), or carboxyalkylaminoalkyl.

In some embodiments, $Ar^2$ is thiophen-2-yl, pyridin-3-yl, quinolin-6-yl, benzothiazol-2-yl, benzoxazol-2-yl, benzofuran-2-yl, benzofuran-5-yl, benzothien-2-yl, furan-2-yl, 1H-benzimidazol-2-yl, 1H-pyrrol-2-yl, thiazol-2-yl, 1H -indol-2-yl, 1H-indol-5-yl, 1H-indol-3-yl, quinolin-3-yl, quinolin-8-yl, 1H-indazol-3-yl, 1H-benzotriazol-5-yl, isoquinolin-1-yl, isoquinolin-3-yl, quinoxalin-2-yl, quinolin-2-yl, 1H-benzimidazol-5-yl, quinolin-1-yl, pyridin-2-yl, pyridine-2-yl, quinolin-2-yl, furan-3-yl, thiophen-2-yl, or thiophen-3-yl. In some embodiments, $Ar^2$ is benzofuran-2-yl, or benzothien-2-yl that is optionally substituted with one or two substituents described in the paragraph immediately above.

In some embodiments, $Ar^2$ is benzofuran-2-yl and is monosubstituted at the 3-, 4-, or 5-position or disubstituted at the 4 and 7 positions. In some embodiments, the benzofuran-2-yl of $Ar^2$ is monosubstituted at the 3 or 5 position with a substituent described in the paragraph immediately above. In some embodiments, the substituents are independently selected from chloro, fluoro, trifluoromethyl, methyl, ethyl, methoxy, 1-cyclopropylpiperidin-4-yloxy, 1-(2,2,2-trifluoroethyl)piperidin-4-yloxy, N,N-dimethylaminomethyl, N,N-diethylaminomethyl, 2-methoxyethoxymethyl, phenoxymethyl, 2-methoxyethoxy, 2-morpholin-4-ylethoxy, pyridin-3-ylmethoxy, 2-hydroxyethoxy, 2-N,N -dimethylaminoethoxy, methoxymethyl, 3-1-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 4-[1,2,4-triazin-1-yl-phenoxymethyl, 2-phenylethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, pyridin-3-ylmethyloxymethyl, tetrahydropyran-4-yloxy, 2,2,2-trifluoroethyloxy, 2-pyrrolidin-1-ylethyloxy, piperidin-4-yloxy, N-methyl-N-benzylaminomethyl, N-methyl-$N^2$-phenylethylaminomethyl, 3-hydroxypropylthiomethyl, 3-hydroxypropylsulfinylmethyl, 3-hydroxypropylsulfonyl-methyl, N-methyl-$N^2$-indol-3-ylethylaminomethyl, 2-(4-trifluoromethylphenyl)ethyl, 2-(3-trifluoromethoxyphenyl)ethyl, N-hydroxyaminocarbonyl-methylaminomethyl, or 3-(2-carboxyethylamino-methyl).

In some embodiments, $Ar^2$ is benzofuran-2-yl that is substituted at the 3-position with N,N-dimethylaminomethyl, N,N-diethylaminomethyl, 2-fluorophenoxymethyl, 3-fluorophenoxymethyl, 4-fluorophenoxymethyl, pyridin-4-yloxymethyl, 2,4,6-trifluorophenoxy-methyl, 2-oxopyridin-1-ylmethyl, 2,2,2-trifluoroethoxy-methyl, 4-imidazol-1-ylphenoxy-methyl, 4-[1,2,4]-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trifluoromethyl-piperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenylethyl)-, N-methyl-N-benzyl-aminomethyl, N-methyl-N-2-phenylethylaminomethyl, 3-hydroxypropylthiomethyl, 3-hydroxypropylsulfinyl-methyl, 3-hydroxypropylsulfonylmethyl, N-methyl-$N^2$-indol-3-ylethylaminomethyl, 2-(4-trifluoromethylphenyl)ethyl, N-hydroxyaminocarbonyl-methylaminomethyl, or 2-carboxyethylamino-methyl.

In some embodiments, $Ar^2$ is benzofuran-2-yl that is substituted at the 5-position with 1-cyclopropylpiperidin-4-yloxy, piperidin-4-yloxy, tetrahydropyran-4-yloxy, 2,2,2-trifluoroethoxy, 2-pyrrolidin-1-ylethyloxy, or 1-(2,2,2-trifluoroethyl)piperidin-4-yloxy.

In some embodiments, $Ar^2$ is 7-chloro-4-methylbenzofuran-2-yl, 4-methyl-benzofuran-2-yl, 7-fluoro-4-methylbenzofuran-2-yl, or 7-fluoro-4-phenoxymethylbenzofuran-2-yl.

In some embodiments, $Ar^2$ is thiophen-2-yl, pyridin-3-yl, 5-phenylthiophen-2-yl, quinolin-6-yl, 4-phenylthiazol-2-yl, benzothiazol-2-yl, benzoxazol-2-yl, furan-2-yl, 1H-benzimidazol-2-yl, 1H-pyrrol-2-yl, 4-(pyridin-4-yl)-thiazol-2-yl, 1H-indol-5-yl, 1H-indol-3-yl, quinolin-3-yl, quinolin-8-yl, 1H-indazol-3-yl, 1H-benzotriazol-5-yl, isoquinolin-1-yl, isoquinolin-3-yl, quinoxalin-2-yl, quinolin-2-yl, 1H-benzimidazol-5-yl, 1-methyl-indol-3-yl, 4-MeO-quinolin-2-yl, quinolin-4-yl, 4-hydroxyquinolin-2-yl, pyridin-2-yl, 3-hydroxypyridin-2-yl, 6-hydroxypyridin-2-yl, 6-(4-nitrophenoxy)pyridin-2-yl, 4-(2-methoxyethoxy)quinolin-2-yl, 4-(2-dimethylaminoethoxy)quinolin-2-yl, 6-bromopyridin-2-yl, 5-bromopyridin-3-yl, 4-methoxyquinolin-2-yl, 5-phenylpyridin-3-yl, 6-benzyloxypyridin-2-yl, 6-(2-methylpropyloxy)-pyridin-2-yl, 6-(2-phenylethyloxy)pyridin-2-yl, 4-(3,3,3-trifluoropropyloxy)quinolin-2-yl, 5-thiophen-3-ylpyridin-3-yl, 6-(4-acetylaminophenoxy)-pyridin-2-yl, 6-(4-aminophenoxy)-pyridin-2-yl, or 5-(4-dimethylaminophenyl)pyridin-3-yl.

V. Group V of compounds of Formula (I) is that wherein $Ar^2$ is heteroaryl. In some embodiments, $Ar^2$ is heteroaryl optionally substituted with one or two substituents independently selected from alkyl, halo, haloalkyl, alkoxy, alkoxyalkyl, hydroxyalkoxy, hydroxyalkoxyalkyl, alkoxyalkyloxy, alkoxyalkyloxyalkyl, aminoalkyl, aminoalkoxy, haloalkoxy, haloalkoxyalkyl, optionally substituted phenylalkyl, optionally substituted phenyloxyalkyl, optionally substituted heteroaryl, optionally substituted heteroaralkyloxy, optionally substituted heteroaryloxyalkyl, optionally substituted heterocycloalkylalkyl, optionally substituted heterocycloalkyloxy, optionally substituted heterocycloalkylalkyloxy, -alkylene-S(O)$_n$$R^a$ (where n is 0 to 2 and $R^a$ is hydroxyalkyl or optionally substituted phenyl), -alkylene-N$R^e$-alkyleneCON$R^c$$R^d$ (where $R^cC$ is hydroxyl and $R^d$ and $R^e$ are independently hydrogen or alkyl), or carboxyalkylaminoalkyl.

In some embodiments, $Ar^2$ is thiophen-2-yl, pyridin-3-yl, quinolin-6-yl, benzothiazol-2-yl, benzoxazol-2-yl, benzofuran-2-yl, benzofuran-5-yl, benzothien-2-yl, furan-2-yl, 1H-benzimidazol-2-yl, 1H-pyrrol-2-yl, thiazol-2-yl, 1H-indol-2-yl, 1H-indol-5-yl, 1H-indol-3-yl, quinolin-3-yl, quinolin-8-yl, 1H-indazol-3-yl, 1H-benzotriazol-5-yl, isoquinolin-1-yl, isoquinolin-3-yl, quinoxalin-2-yl, quinolin-2-yl, 1H-benzimidazol-5-yl, quinolin-1-yl, pyridin-2-yl, pyridine-2-yl, quinolin-2-yl, furan-3-yl, thiophen-2-yl, or thiophen-3-yl. In some embodiments, $Ar^2$ is benzofuran-2-yl, or benzothien-2-yl that is optionally substituted with one or two substituents described in the paragraph immediately above.

In some embodiments, $Ar^2$ is benzofuran-2-yl and is monosubstituted at the 3-, 4- or 5-position or disubstituted at the 4 and 7 positions. In some embodiments, the benzofuran-2-yl of $Ar^2$ is monosubstituted at the 3 or 5 position with a substituent described in the paragraph immediately above. In some embodiments, the substituents are independently selected from chloro, fluoro, trifluoromethyl, methyl, ethyl, methoxy, 1-cyclopropylpiperidin-4-yloxy, 1-(2,2,2-trifluoroethyl)piperidin-4-yloxy, N,N-dimethylaminomethyl, N,N-diethylaminomethyl, 2-methoxyethoxymethyl, phenoxymethyl, 2-methoxyethoxy, 2-morpholin-4-ylethoxy, pyridin-3-methoxy, 2-hydroxyethoxy, 2-N,N-dimethylaminoethoxy, methoxymethyl, 3-i-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 4-[1,2,4-triazin-1-yl-phenoxymethyl, 2-phenylethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, pyridin-3-ylmethyloxymethyl, tetrahydropyran-4-yloxy, 2,2,2-trifluoroethyloxy, 2-pyrrolidin-1-ylethyloxy, piperidin-4-yloxy, N-methyl-N-benzylaminomethyl, N-methyl-N-2-phenylethylaminomethyl, 3-hydroxypropylthiomethyl, 3-hydroxypropylsulfinylmethyl, 3-hydroxypropylsulfonyl-methyl, N-methyl-N-2-indol-3-ylethylaminomethyl, 2-(4-trifluoromethylphenyl)ethyl, 2-(3-trifluoromethoxyphenyl)ethyl, N-hydroxyaminocarbonyl-methylaminomethyl, or 3-(2-carboxyethylamino-methyl).

In some embodiments, $Ar^2$ is benzofuran-2-yl that is substituted at the 3-position with N,N-dimethylaminomethyl, N,N-diethylaminomethyl, 2-fluorophenoxymethyl, 3-fluorophenoxymethyl, 4-fluorophenoxymethyl, pyridin-4-yloxymethyl, 2,4,6-trifluorophenoxy-methyl, 2-oxopyridin-1-ylmethyl, 2,2,2-trifluoroethoxy-methyl, 4-imidazol-1-ylphenoxy-methyl, 4-[1.2.4]-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trufluoromethyl-piperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenylethyl)-, N-methyl-N-benzyl-aminomethyl, N-methyl-$N^2$-phenylethylaminomethyl, 3-hydroxypropylthiomethyl, 3-hydroxypropylsulfinyl-methyl, 3-hydroxypropylsulfonylmethyl, N-methyl-$N^2$-indol-3-ylethylaminomethyl, 2-(4-trifluoromethylphenyl)ethyl, N-hydroxyaminocarbonyl-methylaminomethyl, or 2-carboxyethylamino-methyl.

In some embodiments, $Ar^2$ is benzofuran-2-yl that is substituted at the 5-position with 1-cyclopropylpiperidin-4-yloxy, piperidin-4-yloxy, tetrahydropyran-4-yloxy, 2,2,2-trifluoroethoxy, 2-pyrrolidin-1-ylethyloxy, or 1-(2,2,2-trifluoroethyl)piperidin-4-yloxy.

In some embodiments, $Ar^2$ is 7-chloro-4-methylbenzofuran-2-yl, 4-methyl-benzofuran-2-yl, 7-fluoro-4-methylbenzofuran-2-yl, or 7-fluoro-4-phenoxymethylbenzofuran-2-yl.

In some embodiments, $Ar^2$ is thiophen-2-yl, pyridin-3-yl, 5-phenylthiophen-2-yl, quinolin-6-yl, 4-phenylthiazol-2-yl, benzothiazol-2-yl, benzoxazol-2-yl, furan-2-yl, 1H-benzimidazol-2-yl, 1H-pyrrol-2-yl, 4-(pyridin-4-yl)-thiazol-2-yl, 1H-indol-5-yl, 1H-indol-3-yl, quinolin-3-yl, quinolin-8-yl, 1H-indazol-3-yl, 1H-benzotriazol-5-yl, isoquinolin-1-yl, isoquinolin-3-yl, quinoxalin-2-yl, quinolin-2-yl, 1H-benzimidazol-5-yl, 1-methyl-indol-3-yl, 4-MeO-quinolin-2-yl, quinolin-4-yl, 4-hydroxyquinolin-2-yl, pyridin-2-yl, 3-hydroxypyridin-2-yl, 6-hydroxypyridin-2-yl, 6-(4-nitrophenoxy)pyridin-2-yl, 4-(2-methoxyethoxy)quinolin-2-yl, 4-(2-dimethylaminoethoxy)quinolin-2-yl, 6-bromopyridin-2-yl, 5-bromopyridin-3-yl, 4-methoxyquinolin-2-yl, 5-phenylpyridin-3-yl, 6-benzyloxypyridin-2-yl, 6-(2-methylpropyloxy)-pyridin-2-yl, 6-(2-phenylethyloxy)pyridin-2-yl, 4-(3,3,3-trifluoropropyloxy)quinolin-2-yl, 5-thiophen-3-ylpyridin-3-yl, 6-(4-acetylaminophenoxy)-pyridin-2-yl, 6-(4-aminophenoxy)-pyridin-2-yl, or 5-(4-dimethylaminophenyl)pyridin-3-yl.

Within the above Groups II, III, IV, and V, and groups described therein, in some embodiments, Y is straight alkylene. In some embodiments, Y is ethylene or n-propylene. In some embodiments, Y is ethylene.

Within the above Groups II, III, IV, and V, and groups described therein, in some embodiments, Y is branched alkylene. In some embodiments, Y is —CH($C_2H_5$)$CH_2$—, —CH(i-$C_3H_7$)$CH_2$—, or —CH($CH_3$)$CH_2$— and the stereochemistry at the chiral carbon is (S). In some embodiments, Y is —CH($C_2H_5$)$CH_2$—.

Within the above Groups II, III, IV, and V, and groups described therein, in some embodiments, Y is —$CH_2$CH($CH_3$)— and the stereochemistry at the chiral carbon is (R).

Within the above Groups II, III, IV, and V, and groups described therein, in some embodiments, Y is —CH($CH_2$R')$CH2$— or —CH($CH_2CH_2$R')$CH_2$— where R' is alkylthio, alkysulfonyl, optionally substituted phenylalkylthio, optionally substituted phenylalkylsulfonyl, hydroxy, or optionally substituted phenoxy. In some embodiments, R' is phenyl, phenoxy, 4-chlorophenyl, cyclohexyl, benzylthio, benzylsulfonyl, methylthio, methylsulfonyl, or hydroxy.

VI. Group VI of compounds of Formula (I) is that wherein X is —O—, $R^1$ and $R^3$ are hydrogen, $Ar^1$ is phenylene, $Ar^2$ is aralkenyl, Y is branched alkylene, and the —CONHOH and X are at the 1 and 4 position of the phenylene ring. In some embodiments, $Ar^2$ is trans phenyl-CH=CH— wherein the phenyl is optionally substituted with one or two substituents independently selected from alkyl, alkoxy, methylenedioxy, or hydroxyl.

The scope of the terms contained in groups II-VI above, are as defined in the definition section of this application.

Reference to the embodiments set forth above is meant to include all combinations of particular groups unless stated otherwise.

General Synthesis

In one embodiment, compounds having the structure of Formula (A) or Formula (I) are prepared by the methods depicted in the reaction scheme shown below. United States Patent Application Publication 2005/0187261 describes methods of preparing hydroxamates, the methods which are herein incorporated by reference.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by known methods following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991), *March's Advanced Organic Chemistry*, (John Wiley and Sons, 4th Edition) and *Larock's Comprehensive Organic Transformations* (VCH Publishers Inc., 1989). These schemes are merely illustrative of some methods by which the compounds of Formula (A) or Formula (I) are synthesized, and in some embodiments, various modifications to these schemes are made.

In other embodiments, the starting materials and the intermediates of the reaction are isolated and purified if desired using conventional techniques, including but not limited to filtration, distillation, crystallization, chromatography and the like. In other embodiments, such materials are characterized using conventional means, including physical constants and spectral data.

Unless specified to the contrary, the reactions described herein take place at atmospheric pressure over a temperature range from about −78° C. to about 150° C., from about 0° C. to about 125° C., or at about room (or ambient) temperature, e.g., about 20° C.

Compounds of Formula (I) where X is —O— or —S(O)$_n$— where n is 0 to 2 and other groups are as described herein and in some embodiments are prepared by the procedure illustrated and described in Scheme A below.

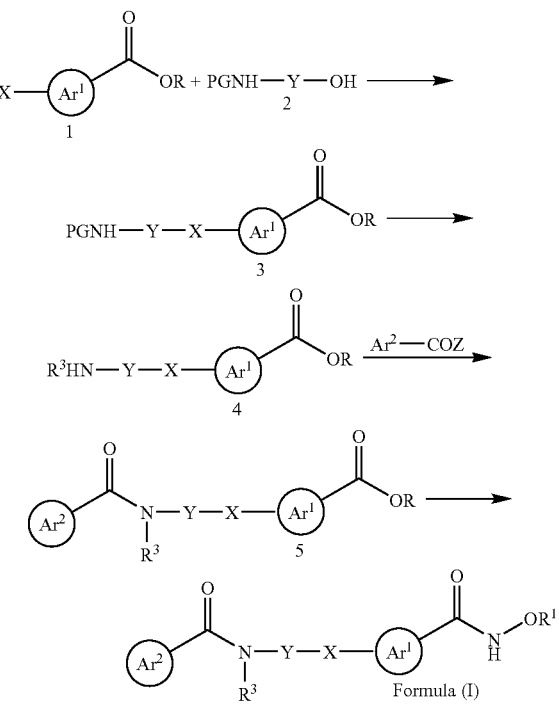

Scheme A

Reaction of a compound of Formula 1 where R is alky, X is —O— or —S— and $Ar^1$ is as defined herein with an aminoalcohol of Formula 2 where PG is a suitable amino protecting group provides a compound of Formula 3. The reaction is carried out in the presence of triphenylphosphine and diisopropyl azodicarboxylate in a suitable organic solvent such as tetrahydrofuran, and the like.

Compounds of Formula 1 such as methyl 4-hydroxybenzoate, methyl 4-mercaptobenzoate, and methyl 3-hydroxyisoxazole-5-carboxylate are commercially available. In some embodiments, compounds of Formula 2 are prepared from commercially available aminoalcohols by reacting the amine with a suitable amino protecting group such as benzyloxycarbonyl, tert-butoxycarbonyl and the like under suitable reaction conditions. In some embodiments, detailed descriptions of suitable amino protecting groups and reaction conditions for their preparation are found in T. W. Greene, *Protecting Groups in Organic Synthesis*, John Wiley & Sons, Inc. 1981 the list of suitable amino protecting groups and reaction conditions of which is incorporated herein by reference. Aminoalcohols such as 2-ethanolamine, 2-amino-1-propanol, 2-methylaminoethanol, 2-amino-2-methyl-1-propanol, 2-amino-1-propanol, 4-amino-2-butanol, and 1-amino-2-butanol are commercially available. In one embodiment, compounds of Formula 2 are prepared from commercially available aminoacids by protecting the amino group with a suitable protecting group followed by reduction of the acid group to the hydroxy group with a suitable reducing agent under standard conditions. In some embodiments where compounds of Formula (I) having X as —$SO_2$—, the corresponding compound of Formula 3 wherein X is —S— is treated with an oxidizing agent such as OXONE®, m-chloroperbenzoic acid, and the like.

Removal of the amino protecting group in 3 provides a compound of Formula 4. The reaction conditions employed for removal of the amino protecting group depend on the nature of the protecting group. For example, in some embodiments, wherein the protecting group is tert-butoxycarbonyl, it is removed under acid reaction conditions. Suitable acids are trifluoroacetic acid, hydrochloric acid, and the like in a suitable organic solvent such as methanol, dioxane, tetrahydrofuran, and the like. In some embodiments where the protecting group is benzyl or benzyloxycarbonyl, it is removed under catalytic hydrogenation reaction conditions. Suitable catalyst are palladium based catalysts and other suitable catalysts. In other embodiments, other suitable reaction conditions for their removal are found in T. W. Greene, *Protecting Groups in Organic Synthesis*, John Wiley & Sons, Inc. 1981. The reaction is carried out in an inert organic solvent methylene chloride, tetrahydrofuran, dioxane, and the like.

Reaction of 4 with an acid or acid derivative (e.g., acid halide) of formula $Ar^2$-COZ where Z is hydroxy or halo provides a compound of Formula 5. Again, the reaction conditions employed depend on the nature of the Z group. In some embodiments wherein Z is hydroxy, the reaction is typically carried out in the presence of a suitable coupling agent e.g., benzotriazole-1-yloxytrispyrrolidino-phosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyluronium hexafluorophosphate (HATU), 1-(3-dimethylaminopropyl)-3-ethylcarbodiimide hydrochloride (EDC.HCl), or 1,3-dicyclohexylcarbodiimide (DCC), optionally in the presence of 1-hydroxybenzotriazole hydrate (HOBt-$H_2O$), and a base such as N,N-diisopropylethylamine, triethylamine, N-methylmorpholine, and the like. In some embodiments, the reaction is carried out at about 20 to 30° C. In some embodiments, the reactions are carried out at about 25° C., and requires about 2 to about 24 hours to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. In some embodiments, the reaction is carried out with HOBt-$H_2O$, EDC.HCl in dichloromethane or N,N-dimethylformamide.

When $Ar^2$-COZ is an acid halide, the reaction is carried out in the presence of a suitable base (e.g. triethylamine, diisopropylethylamine, pyridine, and the like). Suitable reaction solvents are polar organic solvents such as tetrahydrofuran, acetonitrile, N,N-dimethylformamide (DMF), dichloromethane, or any suitable mixtures thereof. In a further embodiment, the acid halide such as acid chloride is prepared by reacting the corresponding acids with a halogenating agent such as oxalyl chloride, thionyl chloride, phosphorus oxychloride, and the like. In yet a further embodiment, acids of formula $Ar^2$-COZ are either commercially available or they are prepared from commercially available starting materials by standard methods. For example, benzoic acid, cinnamic acid, phenylacetic acid, nicotinic acid, isonicotinic acid, 3-methylbenzofuran-2-carboxylic acid, and benzofuran-2-carboxylic acid are commercially available. Others such as 3-phenoxymethylbenzofuran-2-carboxylic acid are readily prepared from commercially available 3-methylbenzofuran-2-carboxylic acid by first converting it to 2-bromomethylbenzofuran-2-carboxylic acid (brominating it with N-bromosuccinimide under standard conditions) followed by reacting with phenol. In other embodiments, compound 5 where $R^3$ is hydrogen is optionally converted to a corresponding compound of Formula 5 where $R^3$ is other than hydrogen by reacting it with an alkylating agent under standard alkylating conditions.

Compound 5 is then converted to a compound of Formula (I) by reacting it with aqueous hydroxylamine in the presence of a base such as sodium hydroxide and a mixture of organic solvents such as tetrahydrofuran and methanol. In one embodiment, the acid group in 5 is first activated with a suitable coupling agent such as 1-(3-dimethylaminopropyl)-3-ethylcarbodiimide hydrochloride (EDC.HCl), or 1,3-dicyclohexylcarbodiimide (DCC), optionally in the presence of 1-hydroxybenzotriazole hydrate (HOBt-$H_2O$) in a suitable organic solvent such as dimethylformamide, and the like, and then reacted with hydroxylamine hydrochloride in the presence of a base such as N,N-diisopropylethylamine, triethylamine, N-methylmorpholine, and the like. In other embodiments, compounds of Formula (I) are prepared from Compound 5 by the methods disclosed in U.S. Pat. No. 5,998,412, the preparation methods of which are incorporated herein by reference.

In yet a further embodiment, compound of Formula (I) is converted to other compounds of Formula (I). For example, a compound of Formula (I) where $Ar^1$ is phenylene, X is —O—, Y is ethylene, $Ar^2$ is 3-dimethylaminomethyl-benzofuran-2-yl, $R^1$ and $R^3$ are hydrogen are prepared by reacting a compound of formula 4 where $Ar^1$ is phenylene, X is —O—, Y is ethylene, and R is alkyl with 3-methylbenzofuran-2-carboxylic acid as described above to give a compound of Formula 5 where $Ar^2$ is 3-methylbenzofuran-2-yl. Bromination of the methyl group with a suitable brominating agent such as N-bromosuccinimide, followed by reaction with dimethylamine provides the corresponding 3-dimethylaminobenzofuran-2-yl compound which is then converted to the desired compound under the reaction conditions described above.

Administration and Pharmaceutical Compositions

In general, compounds having the structure of Formula (A) or Formula (I) are administered in a therapeutically effective amount by any of the accepted modes of administration for agents that serve similar utilities. The actual amount of the compound of Formula (A) or Formula (I), i.e., the active ingredient, will depend upon numerous factors such as the severity of the disease, disorder, or condition to be treated, the age and relative health of the subject, the potency of the compound used, the route and form of administration, and other factors.

In one embodiment, pharmaceutical compositions are formulated in a conventional manner using one or more physiologically acceptable carriers including excipients and auxiliaries which facilitate processing of the active compounds into preparations which are used pharmaceutically. Proper formulation is dependent upon the route of administration chosen. A summary of pharmaceutical compositions described herein are found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and Pharmaceutical Dosage Forms and Drug Delivery Systems, Seventh Ed. (Lippincott Williams & Wilkins 1999), the summary of which is herein incorporated by reference.

Provided herein are pharmaceutical compositions that include a compound described herein, such as, compounds of Formula (A) or Formula (I), and a pharmaceutically acceptable diluent(s), excipient(s), or carrier(s). In addition, the compounds described herein are administered as pharmaceutical compositions in which compounds described herein are mixed with other active ingredients, as in combination therapy. In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutically valuable substances.

In certain embodiments, compositions also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

A pharmaceutical composition, as used herein, refers to a mixture of at least one compound described herein, such as, for example, compounds of Formula (A) or Formula (I), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount varies widely depending on the severity of the disease, disorder, or condition, the age and relative health of the subject, the potency of the compound used and other factors. In some embodiments, the compounds are used singly or in combination with one or more therapeutic agents as components of mixtures.

In other embodiments, the pharmaceutical formulations described herein are administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In other embodiments, pharmaceutical compositions including a compound described herein are manufactured in a conventional manner, such as, by way of example only, by means of conventional mixing, dissolving, granulating, dragee-making, levigating, emulsifying, encapsulating, entrapping or compression processes.

The pharmaceutical compositions include at least one compound described herein, such as, for example, a compound of Formula (A) or Formula (I), as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some embodiments, compounds of Formula (A) or Formula (I) exist as tautomers. All tautomers are included within the scope of the compounds presented herein. Additionally, in some embodiments, the compounds described herein exist in unsolvated as well as solvated forms with pharmaceutically acceptable solvents such as water, ethanol, and the like. The solvated forms of the compounds presented herein are also considered to be disclosed herein.

"Bioavailability" refers to the percentage of the weight of compounds disclosed herein, such as, compounds of Formula (A) or Formula (I), that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which compounds disclosed herein, such as, compounds of Formula (A) or Formula (I), are absorbed into the general circulation when the pharmaceutical composition is taken orally as compared to intravenous injection.

"Blood plasma concentration" refers to the concentration of compounds disclosed herein, such as, compounds of Formula (A) or Formula (I), in the plasma component of blood of a subject. In some embodiments, it is understood that the plasma concentration of compounds of Formula (A) or Formula (I) will vary significantly between subjects, due to variability with respect to metabolism and/or possible interactions with other therapeutic agents. In accordance with one embodiment disclosed herein, the blood plasma concentration of the compounds of Formula (A) or Formula (I) will vary from subject to subject. Likewise, in another embodiment, values such as maximum plasma concentration ($C_{max}$) or time to reach maximum plasma concentration ($T_{max}$), or total area under the plasma concentration time curve ($AUC_{(0-\infty)}$) will vary from subject to subject. Due to this variability, in other embodiments, the amount necessary to constitute "a therapeutically effective amount" of a compound of Formula (A) or Formula (I) will vary from subject to subject.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

A "measurable serum concentration" or "measurable plasma concentration" describes the blood serum or blood plasma concentration, typically measured in mg, μg, or ng of therapeutic agent per ml, dl, or l of blood serum, absorbed into the bloodstream after administration. As used herein, measurable plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

As used herein, the term "subject" is used to mean an animal, such as a mammal, including a human or non-human. In some embodiments, the terms patient and subject are used interchangeably. In further embodiments, pharmaceutical compositions described herein, which include a compound of Formula (A) or Formula (I), are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Examples of Methods of Dosing and Treatment Regimens

In one aspect, the compositions containing the compound(s) described herein are administered for prophylactic and/or therapeutic treatments. In therapeutic applications, the compositions are administered to a patient already suffering from a disease, disorder, or condition, in an amount sufficient to cure or at least partially arrest the symptoms of the disease, disorder, or condition. Amounts effective for this use will depend on the severity and course of the disease, disorder, or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. In some embodiments, when used in a patient, effective amounts for this use depend on the severity and course of the disease, disorder or condition, previous therapy, the patient's health status and response to the drugs, and the judgment of the treating physician.

In some embodiments, the case wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease, disorder, or condition.

In some embodiments, wherein the patient's status does improve, upon the doctor's discretion the administration of the compounds are given continuously; alternatively, the dose of drug being administered is temporarily reduced or temporarily suspended for a certain length of time (i.e., a "drug holiday"). In other embodiments, the length of the drug holiday varies between 2 days and 1 year, including by way of example only, about 2 days, about 3 days, about 4 days, about 5 days, about 6 days, about 7 days, about 10 days, about 12 days, about 15 days, about 20 days, about 28 days, about 35 days, about 50 days, about 70 days, about 100 days, about 120 days, about 150 days, about 180 days, about 200 days, about 250 days, about 280 days, about 300 days, about 320 days, about 350 days, or about 365 days. In further embodiments, the dose reduction during a drug holiday is from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's condition has occurred, a maintenance dose is administered if necessary. Subsequently, in other embodiments, the dosage or the frequency of administration, or both, are reduced, as a function of the symptoms, to a level at which the improved disease, disorder or condition is retained. In further embodiments, patients will, however, require intermittent treatment on a long-term basis upon any recurrence of symptoms.

In other embodiments, the amount of a given agent that corresponds to such an amount varies depending upon factors such as the particular compound, disease, disorder, or condition and its severity, the identity (e.g., weight) of the subject or host in need of treatment, but nevertheless is routinely determined in a manner according to the particular circumstances surrounding the case, including, e.g., the specific agent being administered, the route of administration, the condition being treated, and the subject or host being treated. In some embodiments, however, doses employed for adult human treatment are typically in the range of about 0.02 to about 5000 mg per day or about 1 to about 1500 mg per day. In further embodiments, the desired dose is conveniently presented in a single dose or as divided doses administered simultaneously (or over a short period of time) or at appropriate intervals, for example as two, three, four or more sub-doses per day.

In some embodiments, the pharmaceutical composition described herein are in unit dosage forms suitable for single administration of precise dosages. In unit dosage form, the formulation is divided into unit doses containing appropriate quantities of one or more compound. in other embodiments, the unit dosage is in the form of a package containing discrete quantities of the formulation. Non-limiting examples are packaged tablets or capsules, and powders in vials or ampoules. In another embodiment, aqueous suspension compositions are packaged in single-dose non-reclosable containers. In further embodiments, multiple-dose reclosable containers are used, in which case it is typical to include a preservative in the composition. By way of example only, formulations for parenteral injection are presented in unit dosage form, which include, but are not limited to ampoules, or in multi-dose containers, with an added preservative.

The daily dosages appropriate for the compounds described herein described herein are from about 0.01 to about 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to about 50 mg active ingredient. The foregoing ranges are merely suggestive, as the number of variables in regard to an individual treatment regime is large, and considerable excursions from these recommended values are not uncommon. In further embodiments, such dosages are altered depending on a number of variables, not limited to the activity of the compound used, the disease, disorder, or condition to be treated, the mode of administration, the requirements of the individual subject, the severity of the disease, disorder, or condition being treated, and the judgment of the practitioner.

In yet further embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and in some embodiments is expressed as the ratio between $LD_{50}$ and $ED_{50}$. In other embodiments, the data obtained from cell culture assays and animal studies is used in formulating a range of dosage for use in human. In some embodiments, the dosage of such compounds lies within a range of circulating concentrations that include the $ED_{50}$ with minimal toxicity. In yet further embodiments, the dosage varies within this range depending upon the dosage form employed and the route of administration utilized.

Combination Treatments

In general, the compositions described herein and, in embodiments where combinational therapy is employed, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds having the structure of Formula (A) or Formula (I) with other anti-cancer or chemotherapeutic agents are intended to be covered. In some embodiments, examples of such agents are found in *Cancer Principles and Practice of Oncology* by V. T. Devita and S. Hellman (editors), $6^{th}$ edition (Feb. 15, 2001), Lippincott Williams & Wilkins Publishers. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, agents that interfere with receptor tyrosine kinases (RTKs), integrin blockers, NSAIDs, PPAR agonists, inhibitors of inherent multidrug resistance (MDR), anti-emetic agents, agents useful in the treatment of anemia, agents useful in the treatment of neutropenia, immunologic-enhancing drugs, biphosphonates, aromatase inhibitors, agents inducing terminal differentiation of neoplastic cells, γ-secretase inhibitors, cancer vaccines, and any combination thereof.

"Estrogen receptor modulators" refers to compounds that interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

In some embodiments, estrogen receptor modulators are tamoxifen and raloxifene.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonaVanti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine) -mu-[diamine-platinum(II)]bis[diamine-(chloro)platinum(II)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, ammubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)-benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)-ethyl]-(20S)camptothecin, BNP1350, BNPI1100, BN80915, BN80942, etoposide phosphate, teniposide, sobuzoxane, 2'-dimethylamino-2'-deoxy -etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)colchic(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)-amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2-, 1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxy-cytidine, N-[5-(2,3-dihydrobenzofuryl)sulfonyl]-N'(3,4-dichlorophenyl)urea, N6-[4-deoxy-4-[$N^2$-[2(E), 4(E)-tetradecadienoyl]-glycylamino]-L-glycero-B-L-manno -heptopyranosyl]-adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetra cyclo(7,4,1,0,0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which in some embodiments are delivered via recombinant virus-mediated gene transfer.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chloropheny-1)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethyl-phenyl)-4-[11-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)-methyl]-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[11-(4-cyanobenzyl)-2-methyl-5-imidazolylmethyl]-2-piperazinone, 1-(2,2-diphenylethyl)-3-[N-(1-(4-cyanobenzyl)-1H-imidazol-5-yl-ethyl)carbamoyl]-piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl) benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-31H-imidazol-4-ylmethyl}benzonitrile, 18,19-dihydro-19-oxo-5H,17H-6, 10:12,16-dimetheno-1H-imidazo[4,3-c][1,11,4] dioxa-azacyclononadecine-9-carbonitrile, (O)-19,20-dihydro-19-oxo-5H-18,21-ethano-12,14-etheno-6,10-metheno-22H-benzo[d]imidazo[4,3-k][1,6,9,12]-oxatriazacyclooctadecine-9-carbonitrile, 19,20-dihydro-19-oxo-5H, 17H-18,21-ethano-6,10: 12,16-dimetheno-22H-imidazo[3, 4-h][1,8,11,14]oxatriazacyclo-eicosine-9-carbonitrile, and (O)-19,20-dihydro-3-methyl-19-oxo-5H-18,21-ethano-12, 14-etheno-6,10-metheno-22H-benzo[d]imidazo[4,3-k][1,6, 9,12]oxa-triazacyclooctadecine-9-carbonitrile.

"HMG-CoA reductase inhibitors" refers to inhibitors of 3-hydroxy-3-methylglutaryl-CoA reductase. In some embodiments, compounds which have inhibitory activity for HMG-CoA reductase are readily identified by using known assays. The terms "HMG-CoA reductase inhibitor" and "inhibitor of HMG-CoA reductase" have the same meaning when used herein.

In some embodiments, examples of HMG-CoA reductase inhibitors that are used include but are not limited to lovastatin (MEVACOR®), simvastatin (ZOCOR®), pravastatin (PRAVACHOL®), fluvastatin (LESCOL®), atorvastatin (LIPITOR®) and cerivastatin (also known as rivastatin and BAYCHOL®). In some embodiments, the structural formulas of these and additional HMG-CoA reductase inhibitors that are used in the instant methods are described at page 87 of M. Yalpani, "Cholesterol Lowering Drugs", Chemistry & Industry, pp. 85-89 (Feb. 5, 1996) and U.S. Pat. Nos. 4,782, 084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is intended to be covered.

In some embodiments, in HMG-CoA reductase inhibitors where an open-acid form exists, salt and ester forms are formed from the open-acid, and all such forms are included within the meaning of the term "HMG-CoA reductase inhibitor" as used herein. In some embodiments, the HMG-CoA reductase inhibitor is selected from lovastatin and simvastatin. In one embodiment, the HMG-CoA reductase inhibitor is simvastatin.

Herein, the term "pharmaceutically acceptable salts" with respect to the HMG-CoA reductase inhibitor shall mean non-toxic salts of the compounds employed which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. In other embodiments, further examples of salt forms of HMG-CoA reductase inhibitors include, but are not limited to, acetate, benzenesulfonate, benzoate, bicarbonate, bisulfate, bitartrate, borate, bromide, calcium hydroxyl, camsylate, carbonate, chloride, clavulanate, citrate, dihydrochloride, hydroxyl, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

In other embodiments, ester derivatives of the described HMG-CoA reductase inhibitor compounds act as prodrugs which, when absorbed into the bloodstream of a warm-blooded animal, cleave in such a manner as to release the drug form and permit the drug to afford improved therapeutic efficacy.

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232, 632. Examples of reverse transcriptase inhibitors include delaviridine, efavirenz, GS-840, HBY097, lamivudine, nevirapine, AZT, 3TC, ddC, and ddI. It has been reported that HIV protease inhibitors, such as indinavir or saquinavir, have potent anti-angiogenic activities and promote regression of Kaposi sarcoma.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib, valecoxib, and rofecoxib, carboxyamidotriazole, combretastatin A-4, squalamine, 6-O-chloroacetyl-carbonyl)-fumagillol, thalidomide, angiostatin, troponin-1, angiotensin II antagonists, and antibodies to VEGF.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]-methyl]-1H-1,2,3-triazole-4-carboxamide, CM101, squalamine, combretastatin, RP14610, NX31838, sulfated mannopentose phosphate, 7,7-(carbonyl-bis[imino-N -methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PDK (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD -098059) and inhibitors of mTOR (for example Wyeth CCI-779 and Ariad AP23573). Such agents include small molecule inhibitor compounds and antibody antagonists.

"Apoptosis inducing agents" include, but not limited to, activators of TNF receptor family members (including the TRAIL receptors).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include, but not limited to, tyrosine kinase inhibitors such as inhibitors of c-Kit, Eph, PDGF, Flt3 and c-Met. Further agents include inhibitors of RTKs. Examples of "tyrosine kinase inhibitors" include, but not limited to, N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]-quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-
methyl -9,12-epoxy-1H-diindolo[1,2,3-fg:3',2',1'-kl]pyrrolo [3,4-i][1,6]benzodiazocin-1-one, SH268, genistein, ST 1571, CEP2563, 4-(3-chlorophenylamino)-5,6-dimethyl-7-H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, SU1 1248, ST1571A, N-4-chlorophenyl-4-(4-pyridylmethyl)-1-phthalazinamine, and EMD121974.

HDAC inhibitors are also useful in combination with platelet fibrinogen receptor (GP Iib/IIIa) antagonists, such as tirofiban, to inhibit metastasis of cancerous cells. Tumor cells also activate platelets largely via thrombin generation. This activation is associated with the release of VEGF. The release of VEGF enhances metastasis by increasing extravasation at points of adhesion to vascular endothelium (Amirkhosravi, 1999, *Platelets* 10: 285-292). Therefore, in some embodiments, HDAC inhibitors serve to inhibit metastasis, in combination with GP Iib/IIIa) antagonists. Examples of other fibrinogen receptor antagonists include abciximab, eptifibatide, sibrafiban, lamifiban, lotrafiban, cromofiban, and CT50352.

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$; $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. More recently, PPAR-γ agonists have been shown to inhibit the angiogenic response to VEGF in vitro; both troglitazone and rosiglitazone maleate inhibit the development of retinal neovascularization in mice. Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NPO110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782, 856), and 2(R)-7-(3-(2-chloro-4-(4-fluorophenoxy) phenoxy)propoxy)-2-ethylchromane-2-carboxylic acid.

In some embodiments, the compounds having the structure of Formula (A) or Formula (I) are used in combination with gene therapy for the treatment of cancer. In other embodiments, gene therapy is used to deliver any tumor suppressing gene. Examples of such genes include, but are not limited to, p53, which in some embodiments is delivered via recombinant virus-mediated gene transfer, Duc-4, NF-I, NF-2, RB, WT1, BRCA1, BRCA2, a uPA/uPAR antagonist.

In other embodiments, the compounds having the structure of Formula (A) or Formula (I) are also administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

In some embodiments, the compounds having the structure of Formula (A) or Formula (I) are employed in conjunction with anti-emetic agents to treat nausea or emesis, including acute, delayed, late-phase, and anticipatory emesis, which result from the use of a compound of Formula (A) or Formula (I), alone or with radiation therapy. In further embodiments, for the prevention or treatment of emesis, a compound of Formula (A) or Formula (I) is used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that results upon administration of the instant compounds.

In other embodiments, the compounds having the structure of Formula (A) or Formula (I) are also administered with an agent useful in the treatment of anemia. Such an anemia treatment agent is, for example, a continuous eythropoiesis receptor activator (such as epoetin-α).

In further embodiments, the compounds having the structure of Formula (A) or Formula (I) are also administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

In some embodiments, the compounds having the structure of Formula (A) or Formula (I) are also administered with an immunologic-enhancing drug, such as levamisole, *bacillus* Calmette-Guerin, octreotide, isoprinosine and Zadaxin.

In other embodiments, the compounds having the structure of Formula (A) or Formula (I) are also useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate(Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

In further embodiments, the compounds having the structure of Formula (A) or Formula (I) are also useful for treating or preventing breast cancer in combination with aromatase inhibitors. Examples of aromatase inhibitors include but are not limited to: anastrozole, letrozole and exemestane.

In some embodiments, the compounds having the structure of Formula (A) or Formula (I) are also useful for treating or preventing cancer in combination with siRNA or RNAi therapeutics.

In some other embodiments, the compounds having the structure of Formula (A) or Formula (I) are also useful for treating or preventing cancer in combination with compounds which induce terminal differentiation of the neoplastic cells. Suitable differentiation agents include the following compounds: (a) Polar compounds; (b) Derivatives of vitamin D and retinoic acid; (c) Steroid hormones; (d) Growth factors; (e) Proteases; (f) Tumor promoters; and (g) inhibitors of DNA or RNA synthesis.

"DNA methyltransferase inhibitor" refers to compounds which inhibit the methylation of the DNA base cytosine at the C-5 position of that base by the DNA methyltransferase enzyme. Examples of such DNA methyltransferase inhibitor include DNA methyltransferase inhibitors include 5-azacytosine and Zebularine®, Examples of an antineoplastic agent include, in general, microtubule-stabilizing agents (such as paclitaxel (also known as Taxol®), docetaxel (also known as Taxotere®, epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, caminomycin, daunorubicin, aminopterin, methotrexate, methopterin, dichloro-methotrexate, mitomycin C, porfiromycin, Herceptin®, Rituxan®, 5-fluorouracil, 6-mercaptopurine, gemcitabine, cytosine arabinoside, podophyllotoxin or podo-phyllotoxin derivatives such as colchicines, etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins. In some embodiments, the antineoplastic agents are the taxanes and the antineoplastic agent is paclitaxel.

Radiation Therapy

Radiotherapy, also called radiation therapy, is the treatment of cancer and other diseases with ionizing radiation. Ionizing radiation deposits energy that injures or destroys cells in an area being treated (a "target tissue") by damaging their genetic material, making it impossible for these cells to continue to grow. Although radiation damages both cancer cells and normal cells, the latter are better able to repair themselves and function properly. In some embodiments, radiotherapy is used to treat localized solid tumors, such as cancers of the skin, tongue, larynx, brain, breast, prostate, colon, uterus and/or cervix. In some embodiments, it is also used to treat leukemia and lymphoma (cancers of the blood-forming cells and lymphatic system, respectively).

One type of radiation therapy commonly used involves photons, "packets" of energy. X-rays, gamma rays are both photon radiation to be used to treat cancer. Depending on the amount of energy they possess, the rays are used to destroy cancer cells on the surface of or deeper in the body. In other embodiments, the higher the energy of the ray beam, the deeper the rays go into the target tissue.

Another technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" includes all forms of radiation, including but not limited to $\alpha$, $\beta$, and $\gamma$ radiation and ultra violet light, which are capable of directly or indirectly damaging the genetic material of a cell or virus. The term "irradiation" refers to the exposure of a sample of interest to ionizing radiation. Radiotherapy with or without concurrent or sequential chemotherapy is an effective modality for head and neck, breast, skin, anogenital cancers, and certain nonmalignant diseases such as keloid, desmoid tumor, hemangioma, arteriovenous malformation, and histocytosis X. However, the therapeutic benefit is limited by radiation- and chemotherapy-induced mucosal epithelium injuries and cutaneous radiation syndrome (CRS), which include acute reactions of tissue swelling, mucositis, dermatitis, desquamation, and ulceration, and long-term effects of tissue/skin fibrosis, necrosis, and the development of life-threatening sequelae of sarcoma, squamous and basal cell carcinoma.

Provided are methods of using at least one histone deacetylase inhibitor to reduce side effect caused by at least one other therapeutic treatment, such as radiation-induced normal tissue fibrosis or chemotherapy-induced tissue necrosis, and the methods provided herein also synergistically inhibit tumor cell growth with radiotherapy and other anti-cancer agents.

It is a further aspect that compounds having the structure of Formula (A) or Formula (I) are administered in conjunction with chemical agents that are understood to mimic the effects of radiotherapy and/or that function by direct contact with DNA. In some embodiment, agents for use in combination with compounds of Formula (A) or Formula (I) for treating cancer include, but are not limited to cis-diamminedichloro platinum (II) (cisplatin), doxorubicin, 5-fluorouracil, taxol, and topoisomerase inhibitors such as etoposide, teniposide, irinotecan and topotecan. Alkylating agents include, but not limited to, BCNU, CCNU and MMS. Crosslinking agents include, but not limited to, cisplatin and carboplabim.

In some embodiments, the term "combination" is present as a fixed combination, kit-of-parts or non-fixed combination as set forth below:

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a single formulation. Another example of a "fixed combination" is a pharmaceutical combination wherein the said first active ingredient and the said second active ingredient are present in one unit without being in admixture;

A "kit-of-parts" is defined as a combination wherein the said first active ingredient and the said second active ingredient are present in more than one unit. One example of a "kit-of-parts" is a combination wherein the said first active ingredient and the said second active ingredient are present separately. In other embodiments, the components of the kit-of-parts are administered separately, sequentially, simultaneously, concurrently or chronologically staggered.

Provided are pharmaceutical compositions comprising at least one compound having the structure of Formula (A) or Formula (I), and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy, such as in therapy of certain diseases responsive or sensitive to the inhibition of histone deacetylases, or (hyper)

proliferative diseases and/or disorders responsive to induction of apoptosis, such neoplasia or any of those cancer diseases described herein.

Also provided are combination products, comprising:
(a) at least one compound having the structure of Formula (A) or Formula (I) formulated with a pharmaceutically acceptable carrier or diluent, and
(b) at least one art-known anti-cancer agent, such as e.g. one or more of those mentioned herein above, formulated with a pharmaceutically acceptable carrier or diluent.

Also provided are kit-of-parts comprising a preparation of at least one compound having the structure of Formula (A) or Formula (I), and a pharmaceutically acceptable carrier or diluent; and a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. In a further embodiment, said kit comprises instructions for its use in therapy, e.g. to treat diseases responsive or sensitive to the inhibition of histone deacetylases, such as cellular neoplasia or diseases different to cellular neoplasia as described herein, particularly cancer, such as any of those cancer diseases described herein.

In some embodiments, cancers that are treated by the methods provided herein include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia)! ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematoloqic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; and Adrenal glands: neuroblastoma.

In some embodiments, acute myelocytic leukemia (AML) and/or acute lymphocytic leukemia (ALL) are treated using compounds having the structure of Formula (A) or Formula (I) in monotherapy or combination therapy. In addition to cancer, in some embodiments, compounds having the structure of Formula (A) or Formula (I) are effective against any of a wide variety of hyperproliferative disorders including, but not limited to: autoimmune disease, arthritis, inflammatory bowel disease, proliferation induced after medical procedures, including, but not limited to, surgery, angioplasty, and the like.

Antidiabetic Agents

In some embodiments, where a subject is suffering from an insulin deficiency (e.g., type I diabetes), the subject is administered a therapeutically effective amount of a HDAC inhibitor in combination with one or more other antidiabetic agents (by the same or separate administration routes). Examples of antidiabetic agents that are useful in combination with a HDAC inhibitor include, but not limited to, insulin secretagogues or insulin sensitizers, or other antidiabetic agents. Such antidiabetic agents include, e.g., biguanides, sulfonyl ureas, glucosidase inhibitors, peroxisome proliferator activated receptor (PPAR) γ agonists, such as thiazolidinediones, PPAR α agonists such as fibric acid derivatives, aP2 inhibitors, dipeptidyl peptidase IV (DP4) inhibitors, sodium glucose co-transporter type 2 (SGLT2) inhibitors, meglitinides, insulin, and/or glucagon-like peptide-1 (GLP-1).

In further embodiments, the other antidiabetic agent is an oral antihyperglycemic agent, e.g., a biguanide such as metformin or phenformin or salts thereof.

In some other embodiments, the other antidiabetic agent is a sulfonyl urea such as glyburide (also known as glibenclamide), glimepirid, glipizide, gliclazide or chlorpropamide, other known sulfonylureas or other antihyperglycemic agents which act on the ATP-dependent channel of pancreatic β cells.

In yet another embodiment, the antidiabetic agent is also a glucosidase inhibitor such as acarbose or miglitol.

In a further embodiment, a HDAC inhibitor is employed in combination with an insulin sensitizer such as troglitazone (Rezulin™), rosiglitazone, pioglitazone, MCC-555, GL-262570, englitazone (CP-68722) or darglitazone (CP-86325), isaglitazone, JTT-501, L-895645, R-119702,N,N-2344, or YM-440.

In other embodiments, a HDAC inhibitor is employed in combination with a antihyperglycemic agent such as insulin or with glucagon-like peptide-1 (GLP-1) such as GLP1 (1-36) amide, GLP-1 (7-36) amide, GLP-1 (7-37) as well as AC2993 and LY-315902.

In another embodiment, the other antidiabetic agent is a PPAR. α/γ dual agonist such as AR-HO39242, GW-409544, KRP297 as well as those disclosed by Murakami et al, "A Novel Insulin Sensitizer Acts As a Coligand for Peroxisome Proliferation—Activated Receptor α (PPAR α) and PPARγ. Effect on PPAR α Activation on Abnormal Lipid Metabolism in Liver of Zucker Fatty Rats", *Diabetes* 47, 1841-1847 (1998).

In a further embodiment, the antidiabetic agent is an SGLT2 inhibitor.

In yet a further embodiment, the antidiabetic agent is an αP2 inhibitor such as disclosed in U.S. application Ser. No. 09/391,053, and in U.S. provisional application No. 60/127,745, employing dosages as set out herein.

In another embodiment, the antidiabetic agent is a DP4 inhibitor such as disclosed in Provisional Application 60/188,555, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S) -pyrrolidine), (tryptophyl-1,2,3,4-tetrahydro-isoquinoline-3-carboxylic acid, 2-cyanopyrrolidides and 4-cyanopyrrolidides employing dosages as set out in the above references.

Growth Hormone Secretagogues

In another embodiment, a HDAC inhibitor is used in combination with one or more growth hormone secretagogues including, but not limited to, arginine, L-3,4-dihydroxyphenylalanine (1-Dopa), glucagon, vasopressin, PACAP (pituitary adenylyl cyclase activating peptide), muscarinic receptor agonists and a synthethic hexapeptide, GHRP (growth hormone releasing peptide).

Other Indications

In further embodiments, HDAC inhibitors are used for diseases other than cancer, include systemic lupus erythematosus, rheumatoid arthritis, inflammatory diseases, and neurodegenerative diseases such as Huntington's disease.

In some embodiments, methods and pharmaceutical compositions provided herein are used for the following indications:

(i) arthropathies and osteopathological diseases such as rheumatoid arthritis, osteoarthritis, gout, polyarthritis and psoriatic arthritis;

(ii) autoimmune diseases, for example, systemic lupus erythematosus and transplant rejection;

(iii) hyperproliferative diseases such as psoriasis or smooth muscle cell proliferation including vascular proliferative disorders, atherosclerosis and restenosis;

(iv) acute and chronic inflammatory diseases and dermal diseases such as ulcerative colitis, Crohns disease, allergic rhinitis, allergic dermatitis, cystic fibrosis, chronic obstructive bronchitis and asthma;

(v) endometriosis, uterine fibroids, endometrial hyperplasia and benign prostate hyperplasia;

(vi) cardiac dysfunction;

(vii) inhibiting immunosuppressive conditions like HIV infections;

(viii) pathological conditions amenable to treatment by potentiating of endogenous gene expression as well as enhancing transgene expression in gene therapy;

(ix) neuropathological disorders like Parkinson disease, Alzheimer disease or polyglutamine related disorders.

Generally, neurodegenerative disorders to be treated by the method provided herein are grouped as follows:

I. Disorders characterized by progressive dementia in the absence of other prominent neurologic signs, such as Alzheimer's disease; Senile dementia of the Alzheimer type; and Pick's disease (lobar atrophy);

II. Syndromes combining progressive dementia with other prominent neurologic abnormalities such as (A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and (B) syndromes appearing mainly in children or young adults (e.g., Hallervorden-Spatz disease and progressive familial myoclonic epilepsy);

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de Ia Tourette syndrome;

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders);

V. Syndrome of central autonomic nervous system failure (Shy-Drager syndrome);

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia;

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy;

VIII. Syndromes of progressive visual loss such as pigmentary degeneration of the retina (retinitis pigmentosa), and hereditary optic atrophy (Leber's disease).

In other embodiments, the methods and pharmaceutical compositions provided herein are also useful in the inhibition of smooth muscle cell proliferation and/or migration and are thus useful in the prevention and/or treatment of restenosis, for example after angioplasty and/or stent implantation.

EXAMPLES

The following preparations and examples are given to more clearly understand and to practice the methods and pharmaceutical compositions described herein. They are not to be considered as limiting the scope of the description, but merely as being illustrative and representative thereof.

Biological Examples

Example 1

Inhibition of HDAC

Measurements are performed in a reaction volume of 100 μL using 96-well assay plates. HDAC-1 (200 pM final concentration) in reaction buffer (50 mM HEPES, 100 mM KCl, 0.001% Tween-20, 5% DMSO, pH 7.4) is mixed with inhibitor at various concentrations and allowed to incubate for 30 minutes, after which trypsin and acetyl-Gly-Ala -(N-acetyl-Lys)-AMC are added to final concentrations of 50 nM and 25 μM, respectively, to initiate the reaction. Negative control reactions are performed in the absence of inhibitor in replicates of eight.

The reactions are monitored in a fluorescence plate reader. After a 30 minute lag time, the fluorescence is measured over a 30 minute time frame using an excitation wavelength of 355 nm and a detection wavelength of 460 nm. The increase in fluorescence with time is used as the measure of the reaction rate. Inhibition constants are obtained using the program BatchKi (Kuzmic et al., 2000, Anal. Biochem. 286: 45-50).

Studies have shown that trichostatin A, a hydroxamic acid histone deacetylase inhibitor, demonstrates an increase in histone acetylation with increasing drug dosage. Previous studies, however, offer evidence of an increased histone acetylation following a relatively low dose of HDAC inhibitor. See e.g., Buggy et al., 2006, Mol. Cancer. Ther., 5: 1309-17. The compounds described herein provide a near maximum histone acetylation at relatively minimal dosages of compound and treatment length.

Example 2

Inhibition of HDAC in Cell Extracts

HeLa nuclear extracts (supplier: Biomol) are incubated at 60 μg/ml with $2 \times 10^{-8}$ M of radiolabeled peptide substrate. As a substrate for measuring HDAC activity a synthetic peptide, i.e. the amino acids 14-21 of histone H4, is used. The substrate is biotinylated at the $NH_2$-terminal part with a 6-aminohexanoic acid spacer, and is protected at the COOH-terminal part by an amide group and specifically [$^3H$]acetylated at lysine 16. The substrate, biotin-(6-aminohexanoic)-Gly-Ala-([.sup.3H]-acetyl-Lys-Arg-His-Arg-Lys-Val-NH.sub.2), is added in a buffer containing 25 mM Hepes, 1 M sucrose, 0.1 mg/ml BSA and 0.01% Triton X-100 at pH 7.4. After 30 min the deacetylation reaction is terminated by the addition of HCl and acetic acid. (final concentration 0.035 mM and 3.8 mM respectively). After stopping the reaction, the free $^3H$-acetate is extracted with ethylacetate. After mixing and centrifugation, the radioactivity in an aliquot of the upper (organic) phase is counted in a β-counter.

For each experiment, controls (containing HeLa nuclear extract and DMSO without compound), a blank incubation (containing DMSO but no HeLa nuclear extract or compound) and samples (containing compound dissolved in DMSO and HeLa nuclear extract) are run in parallel. In a first instance, compounds are tested at a concentration of $10^{-5}$ M. When the compounds show activity at $10^{-5}$ M, a concentration-response curve is made wherein the compounds are tested at concentrations between $10^{-5}$ M and $10^{-12}$ M. In each test the blank value is subtracted from both the control and the sample values. The control sample represents 100% of substrate deactylation. For each sample the radioactivity is expressed as a percentage of the mean value of the controls. When appropriate $IC_{50}$-values (concentration of the drug, needed to reduce the amount of metabolites to 50% of the control) are computed using probit analysis for graded data. In some embodiments, the effects of test compounds are expressed as $pIC_{50}$ (the negative log value of the $IC_{50}$-value).

Example 3

Cell Proliferation Assay In Vitro

The ability of the compounds of Formula (A) or Formula (I) to inhibit growth of tumor cells in vitro is determined as follows.

Stock cultures of the HCT116 colon carcinoma and other cell lines are maintained in RPMI medium 1640 containing 10% (v/v) fetal bovine serum, 2 mM L-glutamine, 1 mM sodium pyruvate, 50 units/ml penicillin, and 50 μg/ml streptomycin at 37° C. in 5% $CO_2$ humidified atmosphere. Cells are cultured in 75-$cm^2$ culture flasks and subcultures are established every 3 to 4 days so as not to allow the cells to exceed 90% confluence.

HCT116 clls are harvested for proliferation assays by trypsinization (0.05% trypsin/0.53 mM EDTA), washed twice in culture medium, re-suspended in appropriate volume of medium, and then counted using a hemacytometer. Cells are seeded in wells of flat-bottom 96-well plates at a density of 5,000 cell/well in 100 μl. Cells are allowed to attach for 1.5 to 2 hours at 37 C.

Compounds are diluted from 10 mM stock solutions in DMSO. Serial 3-fold dilutions are performed in medium containing 0.6% DMSO in wells (in triplicate) of a 96-well U-bottom plates starting with a 60 μM solution. After dilutions are completed, 100 μl of each compound dilution (in triplicate) is transferred to designated triplicate wells of the 96-well plate containing cells in 100 μl of medium. Final concentrations of the dose-response for compounds in assay plates range from 0.12 to 30 μM. Control wells (cells with no treatment) receive 100 μl of 0.6% DMSO in culture medium. Wells containing medium with no cells serve as the background wells. Cells are cultured with the compounds for 48 and 72 hours at 37° C. in a humidified $CO_2$ incubator.

Cell proliferation is assessed by measuring fluorescence after the addition of the fluorogenic redox indicator, Alamar Blue™ (BioSource International). Ten μl of Alamar Blue™ is added to each well of the 96-well plate(s) 3 to 4 hours prior to the end of the incubation period. Assay plates are read in a fluorescence plate reader (excitation, 530 nM; emission, 620 nM). $GI_{50}$ values (concentration at which the growth of the tumor cells is inhibited by 50%) for compounds are determined by plotting the percent control fluorescence against the logarithm of the compound concentration.

Example 4

Determination of Antiproliferative Activity on A2780 Cells

The human A2780 ovarian carcinoma cells are cultured in RPMI 1640 medium supplemented with 2 mM L-glutamine, 50 μg/ml gentamicin and 10% fetal calf serum. Cells are routinely kept as monolayer cultures at 37° C. in a humidified 5% $CO_2$ atmosphere. Cells are passaged once a week using a trypsin/EDTA solution at a split ratio of 1:40. All media and supplements are obtained from Life Technologies. Cells were free of mycoplasma contamination as determined using the Gen-Probe Mycoplasma Tissue Culture kit (BioMrieux).

Cells are seeded in NUNC™ 96-well culture plates (Life Technologies) and allowed to adhere to the plastic overnight. Densities used for plating are 1500 cells per well in a total volume of 200 μl medium. After cell adhesion to the plates, the medium is changed and drugs and/or solvents are added to a final volume of 200 μL Following four days of incubation, the medium is replaced by 200 μl fresh medium and cell density and viability is assessed using an MTT-based assay. To each well, 25 μl MTT solution was added and the cells are further incubated for 2 hours at 37° C. The medium is then carefully aspirated and the blue MTT-formazan product is solubilized by addition of 25 μl glycine buffer followed by 100 μl of DMSO. The microtest plates are shaken for 10 min on a microplate shaker and the absorbance at 540 nm is measured using an Emax 96-well spectrophotometer (Sopachem). Within an experiment, the results for each experimental condition are the mean of 3 replicate wells. For initial screening purposes, compounds are tested at a single fixed concentration of $10^{-6}$ M. For active compounds, the experiments are repeated to establish full concentration-response curves.

For each experiment, controls (containing no drug) and a blank incubation (containing no cells or drugs) are run in parallel. The blank value is subtracted from all control and sample values. For each sample, the mean value for cell growth (in absorbance units) is expressed as a percentage of the mean value for cell growth of the control. When appropriate, $IC_{50}$-values (concentration of the drug, needed to reduce cell growth to 50% of the control) is computed using probit analysis for graded data (Finney, D. J., *Probit Analyses*, 2nd Ed. Chapter 10, Graded Responses, Cambridge University Press, Cambridge 1962). In other embodiments, the effects of test compounds are expressed as $pIC_{50}$ (the negative log value of the $IC_{50}$-value).

Example 5

Mechanisms of Sensitivity in Primary Hematopoietic Tumors and Tumor Lines to HDAC Inhibitors A test compound having the structure of Formula (A) or Formula (I) was tested for inhibiting growth and inducing apoptosis in a variety of hematopoietic cell lines derived from B-, T- and myeloid malignancies. Growth inhibition and apoptosis were noted at drug concentrations ≤0.125 μM and were accompanied by known biochemical markers of HDAC inhibition including histone and tubulin hyperacetylation. Consistent with these results, Olive et al., found that use of a HDAC inhibitor on exponentially growing SiHa cervical and WiDr colon carcinoma cells over a relatively narrow drug concentration range resulted in maximum growth inhibition. These results are in contrast to other hydroxamates such as suberoylanilide hydroxamic acid (SAHA), which are dose-dependent. See Olive et al., 2007, *Clin. Cancer Res.*, 13(22). The test compound was also active in animal xenograft models of hematopoietic disease. The test compound has good pharmacokinetic and pharmacodynamic profiles in animal models and in humans. To demonstrate the potential clinical utility of the test compound in hematologic tumors, primary leukemia samples were isolated from patients and screened for resistance to the test compound in vitro. Of these 19 primary samples (10 acute myelogenous leukemia (AML) and 9 acute lymphocytic leukemia (ALL)), some of which were derived from patients who had failed standard therapy, none were resistant to the test compound at 0.5 uM and only 2 (1 AML and 1 ALL) were considered resistant at 50 nM. Gene expression analysis using DNA microarrays from these primary tumors revealed alterations of gene expression consistent with HDAC inhibition and defined potential pathways of activity for this compound in these tumors. Several of these pathways were analyzed biochemically and the results indicate that although there are many commonalities, different mechanisms for induction of apoptosis are operative in different cell lines and primary tumors.

These results demonstrate that the test compound is highly active in hematopoietic tumor-derived cell lines in vitro as well as in vivo preclinical models. Furthermore, the high sensitivity of primary leukemic tumors to treatment with the test compound in vitro coupled with the predicted pharmacokinetics in humans suggests that in some embodiments patients with hematopoietic malignancies, particularly AML and ALL, are highly responsive to treatment with HDAC inhibitors in the clinic.

Example 6

Inhibition of Homologous Recombination and Disruption of RAD51 Foci by HDAC Inhibitor To investigate the specific effects of a test compound having the structure of Formula (A) or Formula (I) on Double Strand Break Repair (DSBR), we evaluated cell lines with altered DNA repair pathways that have resulted from either genetic alterations or small molecule inhibitors. CHO cells lacking Ku86 (xrs5), a key protein in Non-Homologous End Joining (NHEJ) were analyzed by clonogenic survival following treatment with varying doses of the test compound. The xrs5 cell line showed an 8-fold decrease in clonogenic survival when compared to the parental CHO-K1 cell line. In contrast, cell lines with a deficiency in Homologous recombination (HR), such as BRCA1 mutant cells, showed no such difference. Use of 1,5-Isoquinolinediol (IQD), which inactivates the base excision repair protein poly-ADP ribose polymerase (PARP) generates lesions that are thought to be repaired by HR. IQD given in combination with the test compound to Ramos cells resulted in a synergistic effect on cell death as measured by AnnexinV/Propidium iodide positive cells. Together, these results suggest that the test compound acts by specifically inhibiting HR. These results are consistent with the Olive et al. study which demonstrated that a histone deacetylase inhibitor described herein did not appear to affect non-homologous end joining as evidenced by no change in the initial rates of repair kinetics.

To explore this further, we analyzed levels of RAD51, an essential protein in HR, by Western blotting and immunofluorescence. Following exposure of HCT116 cells to doses of the test compound ranging from 0.2 μM to 2.0 μM, RAD51 levels decreased to 20% of control by 24 hr, but remained unchanged at 6 hr. Real time PCR analysis demonstrated that RAD51 transcript levels also decreased in both HCT116 cells and DLD-1 cells. Finally, RAD51 nuclear foci were visualized following γ-irradiation. Pretreatment with the test compound at 0.2 μM resulted in complete inhibition of RAD51 foci formation and complete exclusion of RAD51 from the nucleus.

These observations suggest that the test compound inhibits HR by both downregulating RAD51 gene expression, and also by affecting the ability of the cell to form RAD51 foci at the site of the lesion. These observations suggest that, in some embodiments, a compound having the structure of Formula (A) or Formula (I) used in combination with therapeutic agents that generate lesions repaired by HR, such as γ-irradiation, cisplatin, and oxaliplatin, shows the usefulness of using RAD51 as a biomarker to predict clinical efficacy.

Example 7

Biomarkers Associated with the Antiproliferative Effect of an HDAC Inhibitor

The antiproliferative effect of a compound of Formula (A) or Formula (I) on HCT116 cell proliferation is assayed in an Alamar Blue™ fluorometric assay as described by deFries and Mitsuhashi (1995). Briefly, HCT116 cells (5000 in 100 μl per well) are plated in 96-well plates in complete media (RPMI medium 1640 containing 10% (v/v) fetal bovine serum, 2 mM L-glutamine, 1 mM sodium pyruvate). The test compound is diluted from 20 mM stock solutions in DMSO. Serial dilutions are performed in medium containing 0.6% DMSO in wells (in triplicate) of a 96-well U-bottom plates starting with a 60 μM solution. After dilutions are completed, 100 mL of the test compound dilution (in triplicate) is transferred to designated triplicate wells of the 96-well plate containing cells in 100 mL of medium. Control wells (cells with no treatment) receive 100 mL of 0.6% DMSO in culture medium. The final DMSO concentration in each well was 0.3%. Wells containing medium with no cells served as the background wells. Cells are cultured with the test compound for 48 h.

Cell proliferation is assessed by measuring fluorescence after the addition of the fluorogenic redox indicator, Alamar Blue™ (BioSource International). Ten μL of Alamar Blue™ is added to each well of the 96-well plate(s) 4 hr prior to the end of the incubation period. Assay plates are read in a fluorescence plate reader (excitation, 530 nM; emission, 620 nM). The $GI_{50}$ value (concentration at which the growth of the tumor cells was inhibited by 50%) is determined by plotting the percent control fluorescence against the logarithm of the test compound concentration.

Next, the duration of exposure necessary to reach the $GI_{50}$ is determined. Briefly, HCT116 cells are plated in 96-well plates as described for the proliferation assay and pulsed with the test compound (0.3% final DMSO concentration) for varying lengths of time, washed and then incubated in drug-free media for the duration of the 48 h assay and the $GI_{50}$ values are calculated.

To understand the biochemical events associated with the antiproliferative effects of the test compound, cellular levels of acetylated tubulin, phospho-H2AX and cytokeratin 18 fragment aa 387-397 are determined. Importantly, acetylated tubulin is a marker of HDAC inhibition while phospho-H2AX and cytokeratin 18 fragment aa 387-397 are early markers of apoptosis.

For this purpose, HCTL 16 cells are pulsed for varying lengths of time (i.e., 5 mins, 15 mins, 1 h, 2 h, 6 h, 12 h and 18 h) with increasing concentrations of the test compound (0.01 μM, 0.1 μM, 0.5 μM, 5 μM and 10 μM; 0.2% final DMSO concentration) in 24-well plates. After treatment, the cells are collected and lysed in M-Per lysis buffer (Pierce) containing protease and phosphatase inhibitors as per the manufacturer's specifications. Lysates (20 μg total protein) are solubilized in SDS-PAGE reducing sample buffer, boiled and electrophoresed in 16% Tris-glycine gels (Invitrogen). The gels are then blotted onto nikocellulose (22 um membrane; Invikogen) and probed with either a monoclonal anti-acetylated tubulin antibody (Clone 6-11B-1; Sigma) or a polyclonal anti-phospho-H2AX antibody (Catalog number 2577, Phospho-Histone H2AX, Ser 139 Antibody; Cell Signaling). The blots probed with anti-acetylated tubulin antibody are then incubated with an anti-mouse peroxidase-conjugated secondary antibody (Pierce) and the blots are developed for enhanced chemiluminescence with the SuperSignal West Femto Maximum Sensitivity Substrate (Pierce) as per the manufacturer's specifications. The blots probed with anti-phospho-H2AX antibody are then incubated with a peroxidase-conjugated anti-rabbit secondary antibody and the blots were developed for enhanced chemiluminescence with the SuperSignal West Pico Kit (Pierce) as per the manufacturer's specifications. For detection of cytokeratin 18 fragment aa 387-397, a M30 Apoptosense ELISA kit (Peviva, Sweden, distributed by Alexis Biochemicals) is used in which cell lysates (5 fig total protein) are evaluated as per the manufacturer's specifications.

Example 8

Early Biomarker Associated with the Anti-tumor Response of an HDAC Inhibitor To understand the early biochemical events associated with the antiproliferative effects of a test compound having the structure of Formula (A) or Formula (I), cellular levels of phospho-H2AX is determined. Importantly, phospho-H2AX is an early marker of apoptosis. The accumulation of γ-H2AX, as an early indication of anti-tumor response, after administration of a test compound to HCT 116 and HeLaS3 cells is determined.

To better understand the accumulation of γ-H2AX at earlier timepoints, two cll lines, HCT-116 and HeLaS3 are treated with the HDAC inhibitor test compound and monitored for γ-H2AX by both Western blotting and cellular immunoflourescence. Both HCT-116 and HeLaS3 cells are grown in complete medium (McCoy's with 10% FBS and 1× Pen/Strep for HCT116 and DME/Ham F12 1:1 mix with 10% FBS, 2 mM L-Glutamine and 1× Pen/Skep for HeLaS3) in a 24 well dish or 4-well chamberslide overnight (18 h) then treated with the test compound from a mM stock solution in DMSO to reach a final concentration of either 0, 0.1, 1, 3, or 10 μM in the well. The cells are grown incubated with compound for either one hour or two hours, at which point the media is removed and the cells washed once with phosphate buffered saline (PBS). For Western blot analysis, lysates from the heated and untreated cells (20 μg total protein) are electrophoresed and bloted onto PVDF, and the blots are probed with a polyclonal anti-phospho-H2AX antibody (purchased from Cell Signaling) at 1:1000 dilution. The blots are then incubated with an anti-rabbit IgG HRP-coupled secondary antibody at 1:10,000 dilution and developed for enhanced chemiluminescence detection. For cellular immunofluorescence staining, treated cells are washed once with PBS and the fxed and permeabilized cells are stained with monoclonal anti-phospho-H2AX antibody (from Upstate) at 1:500 dilution. The slides are then incubated with anti-mouse IgG AF488 (from Molecular Probes) at 1:2000 and mounted with Profound Gold Anti-fade with DAPI for immunofluorescence imaging.

Example 9

Immunofluorescent Staining of Human Cells

Monolayer cultures of different cells are grown in Dulbecco's MEM medium supplemented with 10% fetal bovine serum and antibiotics. The cells are detached from culture flasks by gentle trypsinization, pelleted and resuspended in phosphate buffered saline (PBS; 136 mM NaCl, 2 mM KCG, 10.6 mM $NaHPO_4$, 1.5 mM $KH_2PO_4$ [pH 7.3]) prewarmed at 37° C. (Haaf, et al., 1995, *Proc. Natl. Acad. Sci. USA* 92: 2298-2302). Cultured cells are washed and resuspended in PBS. The density of somatic cells is adjusted to about $10^5$ cells per ml in PBS. Aliquots (0.5 ml) of the cell suspension are centrifuged onto clean glass slides at 800 rpm for 4 min, in a Cytospin (Shandon, Pittsburg). Immediately after cytocentrifugation, the slides are fixed in –20° C. methanol for 30 min and then immersed in ice-cold acetone for a few seconds to permealize the cells for antibody staining. Following three washes with PBS, the preparations are incubated at 37° C. with rabbit anti-HsRad51 antiserum, diluted 1:50 with PBS containing 0.5% bovine serum albumin, in a humidified incubator for 30 min. The slides are washed three times for 10 min each and then incubated for 30 min with fluorescein-isothiocyanate (FITC)-conjugated anti-rabbit IgG diluted 1:20 with PBS. After three washes with PBS, the preparations are counterstained with 4',6-diamidino-2-phenylindole (DAPI; 0.1 ug/ml for 1 min) and mounted in antifade {90% (vovvol) glycerol/0.1 m tris-HCG pH 8.0)/2.3% 1,4-diazabicyclo [2.2.2]octane (DABCO)}.

Images are taken with a Zeiss epifluorescence microscope with a thermo-electronically cooled charge coupled device (CCD) camera (model PM512; Photometrics, Tucson, Ariz.) which is controlled by an Apple Macintosh computer. Grey scale source images are captured separately with filter sets for fluorescein and DAPI. Gray scale source images are pseudo-colored and merged using Oncor Image and Adobe Photoshop software. Although a CCD imaging system is used, all antibody signals were clearly visible by eye through the microscope. Immunostaining of different cell lines shows that HsRad51 is concentrated in small and discrete sites (foci) throughout nucleoplasm and is largely excluded from nucleoli and cytoplasm.

Example 10

Detection of Expression Level of RAD51 Protein by Western Blotting

For determination of protein levels by Western blot, cellular extracts are prepared as follows. Cells are harvested by scraping; washed with PBS and pelleted by centrifugation. Cell pellets (from 100 mm plate) are resuspended with 200 µl B3 buffer containing protease inhibitors shaken at 4° C. for 10 min and centrifuge at 12,000 rpm at 4° C. in Tomy microcentrifuge for 10 minutes. To make 1 liter of B3 buffer, add 1 ml of NP-40, 50 ml of 5 M NaCl, 10 ml of 0.5 ml EDTA, 50 ml of 1 M Tris HCl at pH7.5 to 889 ml dH$_2$O. The day of cell harvest protease inhibitors are added to B3 buffer (aprotinin, leupeptin and pepstatin to a final concentration of 2 µg/ml, 5 µg/ml and 0.7 µg/ml, respectively). Supernatants are saved for Western blot analysis. Sample protein concentrations are determined by the Bradford Assay (BioRad; Richmond, Calif.). Typically, 50 µg of protein are separated by electrophoresis at 120 V, 150 mAmp for 1.5 hours on a 10% SDS-polyacrylamide mini-gel (Mini Protean II, BioRad; Richmond, Calif.). Proteins are transferred to nitrocellulose (Protran nitrocellulose, Schleicher and Schuell; Keene, N.H.) by transfer for 15 min at 15V, 40 mAmp using a Trans-Blot SD Semi-dry Transfer Cell (BioRad; Richmond, Calif.). Blocking of nitrocellulose filters is conducted overnight at 4° C. in 5% milk in PBS/0.2% Triton X-100. The minimum blocking time is 10 minutes. The liquid is discarded and 5 ml of anti-RAD51 polyclonal antibody is added (Ab1 from Oncogene Research Products, Calbiochem; Cambridge, Mass.; diluted 1:500).

Nitrocellulose membranes are shaken at RT for 1 hour, washed 3 times for 5 minutes in Tris buffered saline (TBS) containing 0.2% Triton X-100, and blocked again for 10 minutes with 5% milk in TBS containing 0.2% Triton X-100. Secondary antibody (goat anti-rabbit at 1:1000 for anti-RAD51 antibody) is added in fresh TBS containing 0.2% Tritan x-100 and milk and shaken for 20-40 minutes, washed 3 times 10 minutes with TBS containing 0.2% Triton X-100. Western blots are developed using Super Signal (Pierce; Rockford, Ill.) according to kit protocol. Expose to Kodak X-OMAT AR film for 10 sec to 1 min.

Additional Methods:

Western Blot Analysis: Cell lines [al NHL except for Jurkat (T-cll leukemia) and K562 (CML)] were treated with PCI-24781 for the designated times, lysed and total protein was quantitated and western blot analysis performed. RAD51 and Actin antibodies were from Santa Cruz.

Tagman Gene Expression Assays: 10 lymphoma cell lines were treated with PCI-24781 for various times and total RNA was isolated and quantitated. Taqman assays were set up using the Taqman master mix (Applied Biosystems) and 50 ng of total RNA as template. Gene expression assay probe sets for RAD51 was purchased from Applied Biosystems.

Annexin V Staining: To determine potential synergy between PCI-24781 and the PARP inhibitor PJ34 in HCT 116 cells, cytotoxicity was evaluated using annexin-V staining after 96 h treatment with specified doses of the agents alone or in combination. The Calcusyn program (Biosoft) was used to generate a combination index that determined the presence of synergism, additivity or antagonism between the two drugs.

Tissue Microarray on primary tumors: Original diagnostic fixed and paraffin embedded histology tissue of FL and DLBCL samples from the Northwestern University Pathology Core archives was used with IRB approval to make TMAs. Slides containing 5 micron sections were stained with mouse anti-Rad511 mAB(#NA71, Calbiochem, San Diego, Calif. processed with the DakoCytomation EnVision+ System (DakoCorporation, Carpinteria, Calif.), and scored by a pathologist using an ACIS II computerized microscope.

Example 11

Baseline RAD51 Expression in Lymphoma

Figure 3:
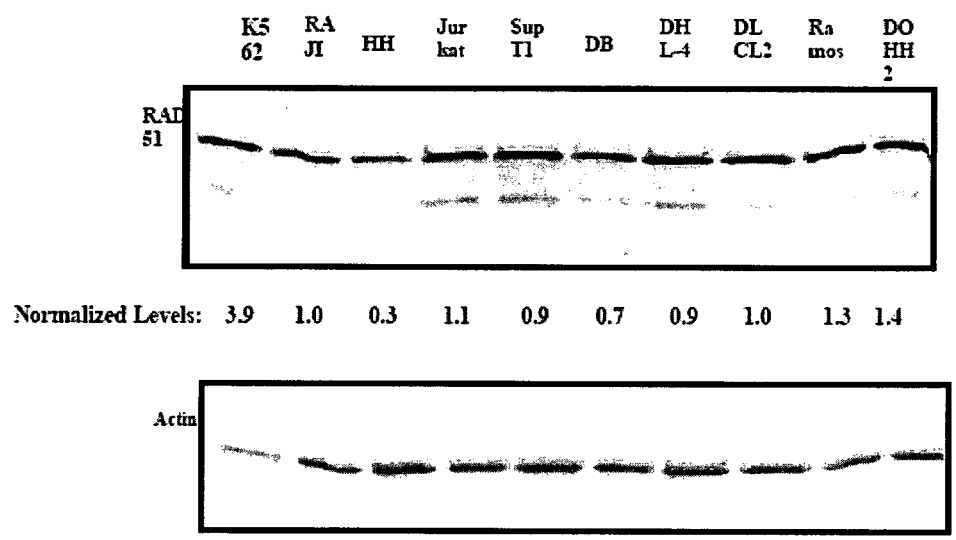
FIG. 3 shows baseline RAD51 expression levels normalized to actin in Non-Hodgkins lymphoma cells by Western blotting, with the lowest levels in HH, a cutaneous T-cell lymphoma line.

Non-Hodgkins Lymphoma (NHL) cell lines were tested (see FIG. 3) and all cell lines expressed RAD51 protein by Western blotting, with the lowest levels in HH, a cutaneous T-cell lymphoma cell line.

Example 12

Figure 2:
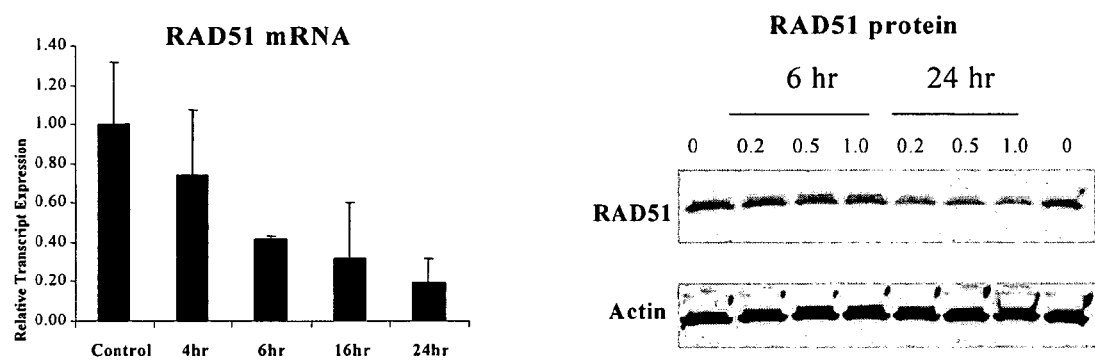
FIG. 2 shows time-course of downregulation of RAD51 by 3-((dimethylamino)methyl)-N-(2-(4-(hydroxycarbamoyl) phenoxy)ethyl)benzofuran-2-carboxamide at both mRNA (left) and protein (right) levels by 24 hrs in the HCT-116 colon tumor line in vitro. Also shown are RAD51 levels and actin levels after extraction of tumor from HCT-116 mouse xenografts with different dosing regimens. 1× animals received a single oral dose 4 hours before the end of the study; 2× animals received one oral dose 28 hours before the end of the study and received a second dose 6 hours later; 3× animals were dosed as in the 2× but also received a third dose the following morning, 24 hours after the first dose was administered and 4 hours before the end of the study. Fold changes in protein levels were quantitated by using Odyssey software and were normalized to the levels of the actin loading control.
Figure 2:
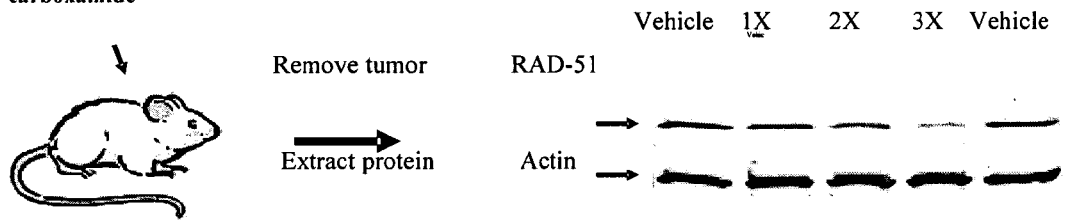

3-((dimethylamino)methyl)-N-(2-(4-(hydroxycarbamoyl)phenoxy)ethyl)benzofuran-2-carboxamide Inhibition of DNA Repair by Homologous Recombination and Sensitization 3-((dimethylamino)methyl)-N-(2-(4-(hydroxycarbamoyl)phenoxy)ethyl)benzofuran-2-carboxamide inhibited DNA repair by homologous recombination and sensitized cells to radiation and DNA-damaging agents by downregulating RAD51 as shown in FIG. 2 wherein RAD51 at both mRNA (left) and protein (right) levels by 24 hours in a HCT-116 colon tumor line in vitro as well as in vivo (not shown). 3-((dimethylamino)methyl)-N-(2-(4-(hydroxycarbamoyl)phenoxy)ethyl)benzofuran-2-carboxamide pretreatment for 24 hours also lead to complete loss of RAD51 foci in the nuclei of irradiated HCT-116 cells (not shown; see Adimoolam et al. 2007, PNAS epub Nov. 27 the experiment, which is herein incorporated by reference).

Example 13

RAD51 Tissue Microarrays

Figure 4:
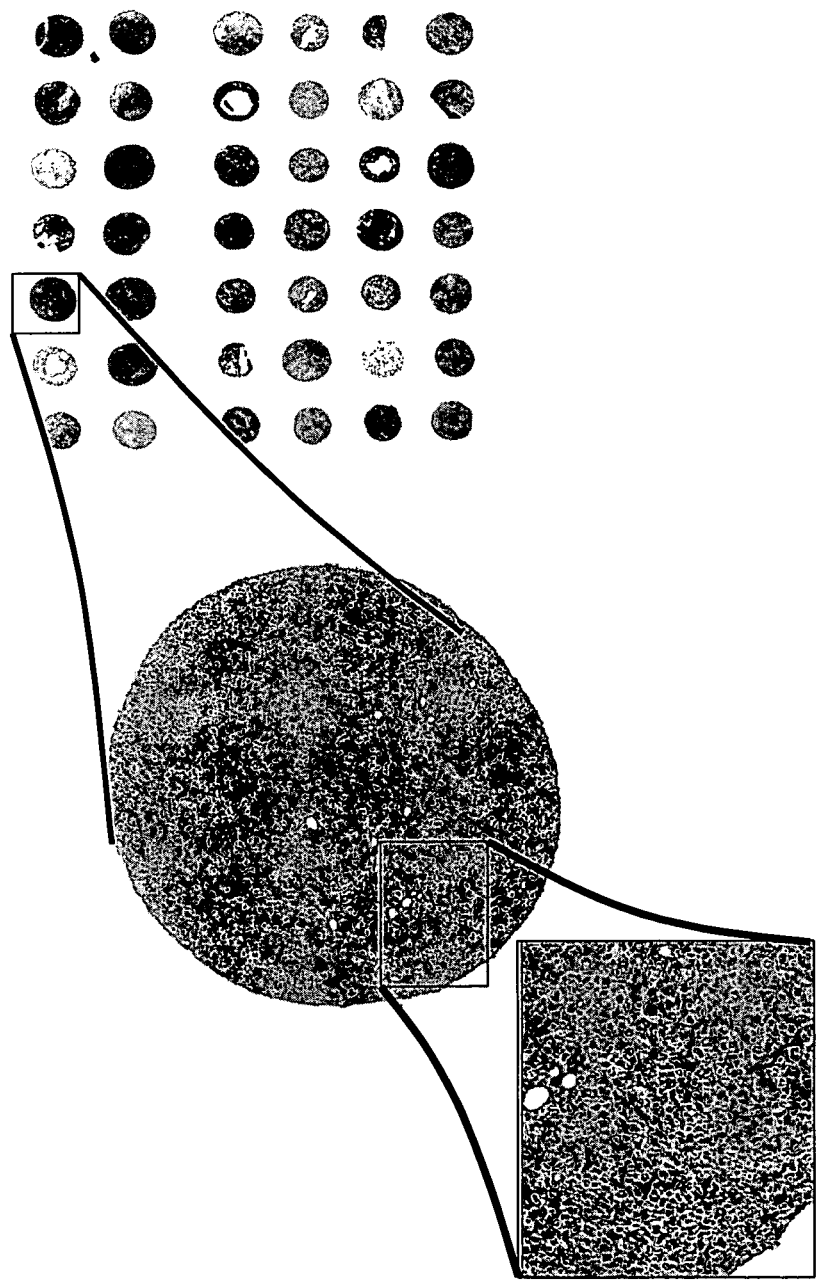
FIG. 4 shows RAD51 expression by immunohistochemical staining in a human DLBCL tumor sample from a tissue microarray (TMA) containing 229 primary tumor sections (138 follicular lymphomas and 91 DLBCL). 78% of the samples of each tumor type in the TMA expressed moderate to high levels of RAD51.

Tissue Microarrays depicted in FIG. 4 show RAD51 overexpression in multiple primary lymphoma tumors. RAD51 expression by immunohistochemical staining in a human DLBCL tumor sample from a tissue microarray (TMA) containing 229 primary tumor sections (138 follicular lymphomas and 91 DLBCL). 78% of the samples of each tumor type in the TMA expressed moderate to high levels of RAD51.

Example 14

Downreglation of RAD51 Protein in Lymphoma Cell Lines

Figure 5:
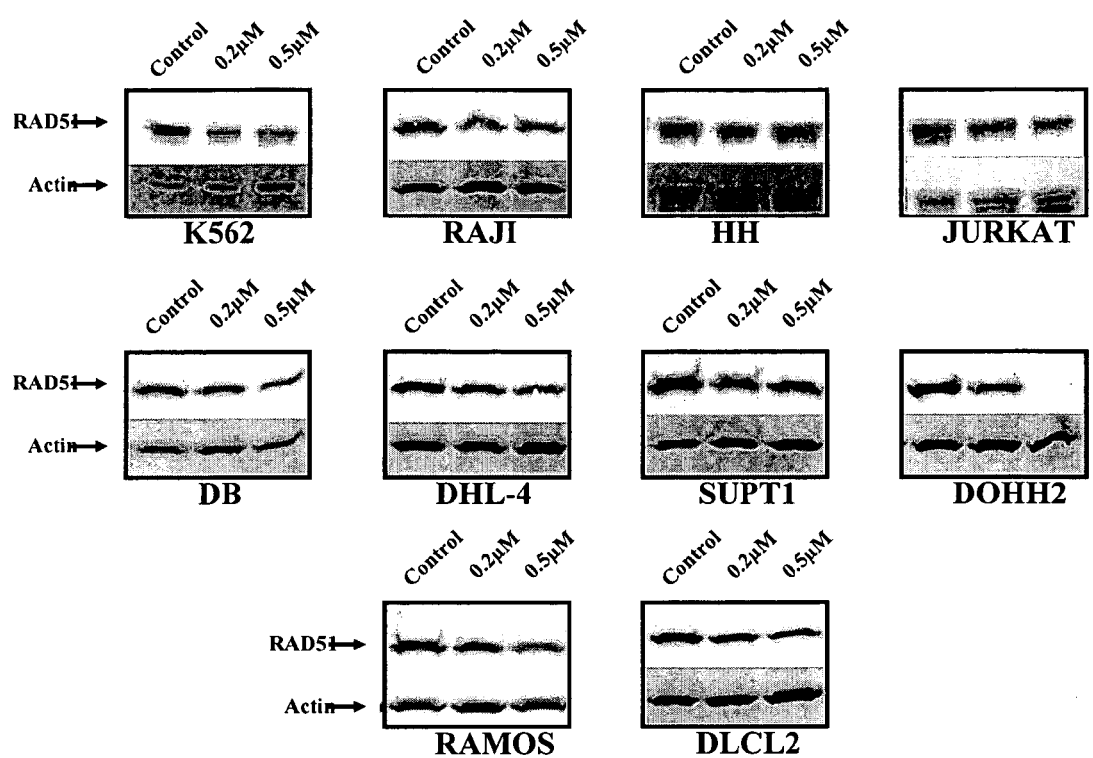
FIG. 5 shows downregulated RAD51 protein levels of NHL cell lines treated with 3-((dimethylamino)methyl)-N-(2-(4-(hydroxycarbamoyl)phenoxy)ethyl)benzofuran-2-carboxamide for 24 hrs in a dose-dependent manner, with HH showing the least effect.

Treatment of Non-Hodgkins cell lines with 3-((dimethylamino)methyl)-N-(2-(4-(hydroxycarbamoyl)phenoxy)ethyl)benzofuran-2-carboxamide treatment for 24 hours showed downregulated RAD51 protein levels in a dose-dependent manner in most of the cell lines tested. The HH cell line showed the least effect (see FIG. 5).

Example 15

RAD51 Transcript Downregulation by Quantitative RT-PCR

Figure 6:
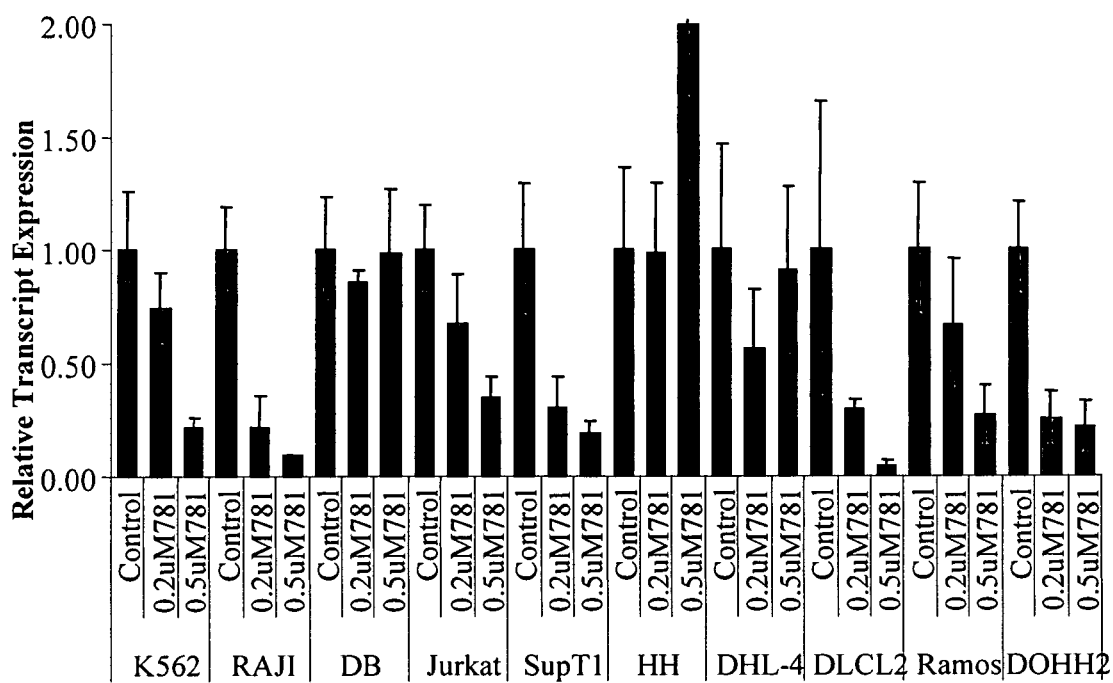
FIG. 6 shows cell lines treated with 3-((dimethylamino)methyl)-N-(2-(4-(hydroxycarbamoyl)phenoxy)ethyl)benzofuran-2-carboxamide for 24 hrs, and RAD51 mRNA then analyzed by Taqman RT-PCR. 3-((dimethylamino)methyl)-N-(2-(4-(hydroxycarbamoyl)phenoxy)ethyl)benzofuran-2-carboxamide downregulated RAD51 mRNA expression by more than 2-fold in most of the cell lines; the HH line showed no decrease in RAD51, in concordance with the Western blotting analysis.

Cell lines were treated with 3-((dimethylamino)methyl)-N-(2-(4-(hydroxycarbamoyl)phenoxy)ethyl)benzofuran-2-carboxamide for 24 hours, and RAD51 mRNA was analyzed by Taqman RT-PCR. 3-((dimethylamino)methyl)-N-(2-(4-(hydroxycarbamoyl)phenoxy)ethyl)benzofuran-2-carboxamide was found to have downregulated RAD51 mRNA expression by more than 2-fold in most of the cell lines (see FIG. 6); the HH cell line showed no decrease in RAD51, in concordance with Western blotting analysis.

Example 16

Figure 7:
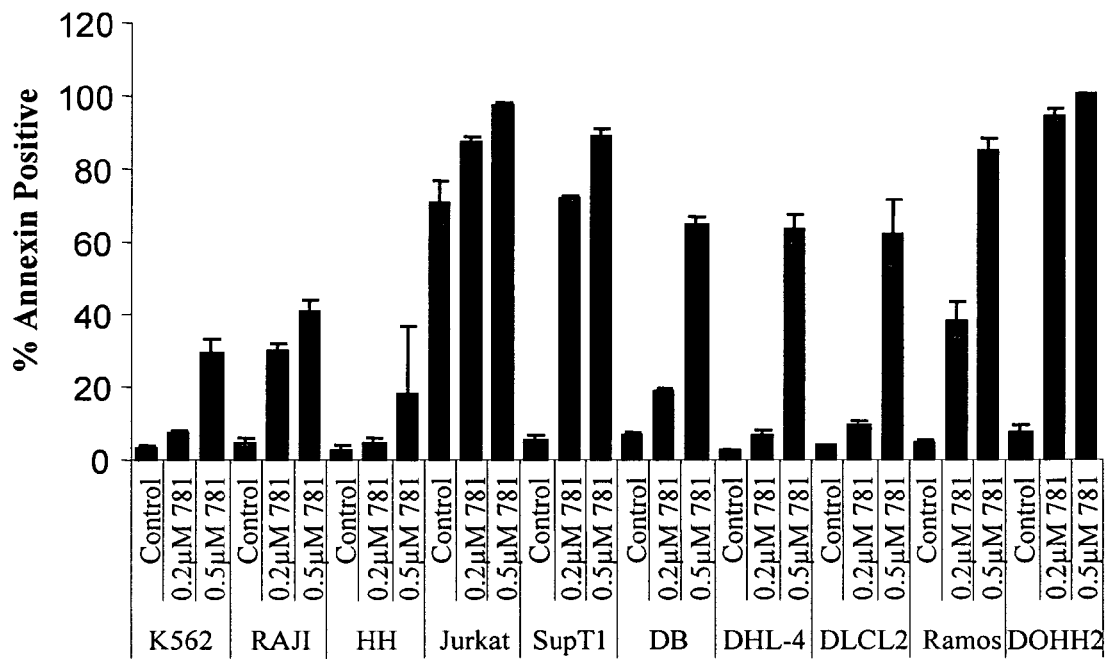
FIG. 7 shows a dose-dependent increase in apoptotic cell death was observed in all the lines with the exception of the HH lymphoma line; lower levels of apoptosis were also observed at 24 hrs in all the lines.

3-((dimethylamino)methyl)-N-(2-(4-(hydroxycarbamoyl)phenoxy)ethyl)benzofuran-2-carboxamide Induced Apoptosis 3-((dimethylamino)methyl)-N-(2-(4-(hydroxycarbamoyl)phenoxy)ethyl)benzofuran-2-carboxamide induced apoptosis in lymphoma cell lines after a 48 hour incubation measured by Annexin V-FITC flow cytometry. A dose-dependent increase in apoptotic cell death was observed in all the lines with the exception of the HH lymphoma line; lower levels of apoptosis were also observed at 24 hrs in all the lines (see FIG. 7). A decrease in the level of RAD51 expression, with each of the five cell lines with >70% apoptosis following drug treatment also showed >4 fold decrease in RAD51 mRNA. Conversely, the HH line, which has the least % apoptosis had the lowest pretreatment levels of RAD51 as well as the least decrease on treatment. Thus, both the initial level of RAD51 in tumors as well as the fold decrease after treatment are predictive for 3-((dimethylamino)methyl)-N-(2-(4-(hydroxycarbamoyl)phenoxy)ethyl)benzofuran-2-carboxamide activity, and in some embodiments is used as biomarkers in clinical studies to identify patients most likely to respond to 3-((dimethylamino)methyl)-N-(2-(4-(hydroxycarbamoyl)phenoxy)ethyl)benzofuran-2-carboxamide.

Example 17

Correlation of RAD51 Expression Biomarkers with Apoptosis

Figure 8A:
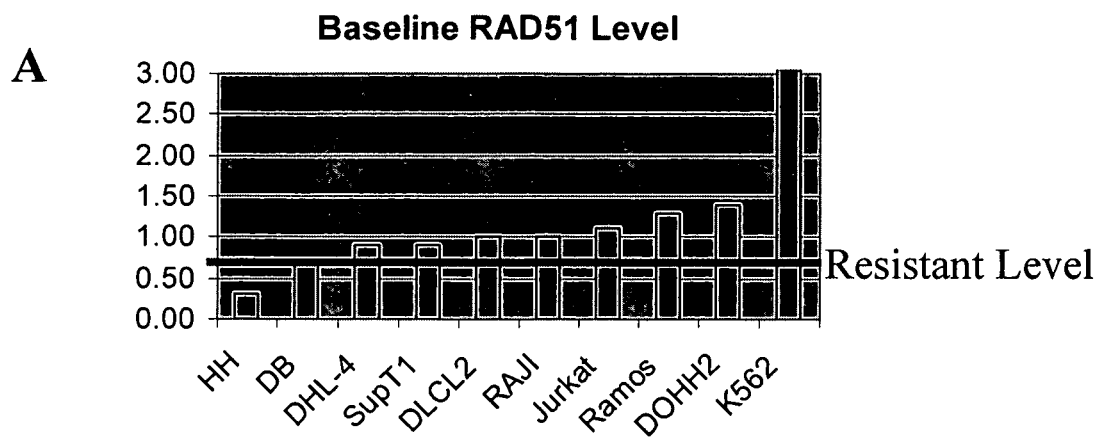
FIG. 8A shows baseline RAD51 expression levels by Western blot.
Figure 8B:
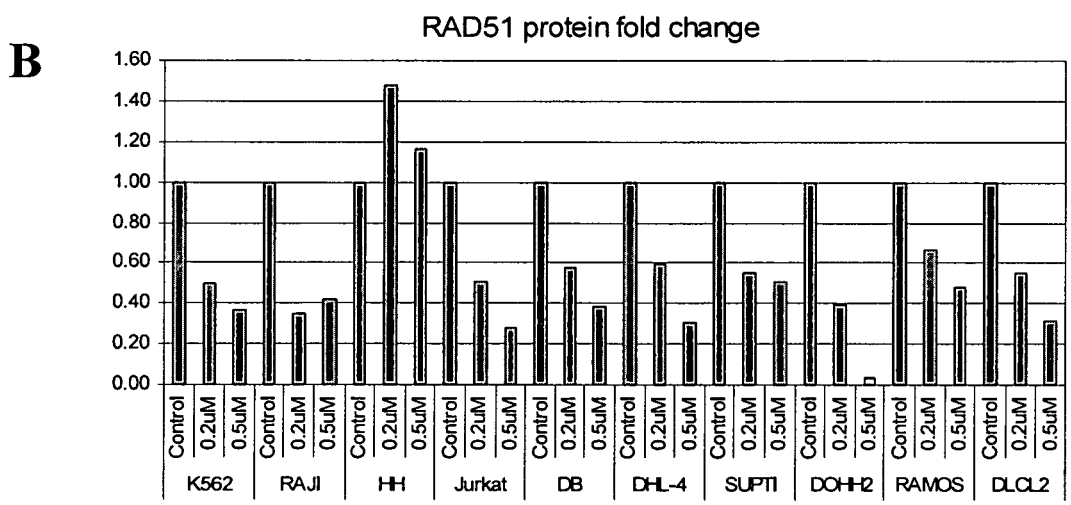
FIG. 8B shows RAD51 protein decrease levels in treated cells.
Figure 8D:
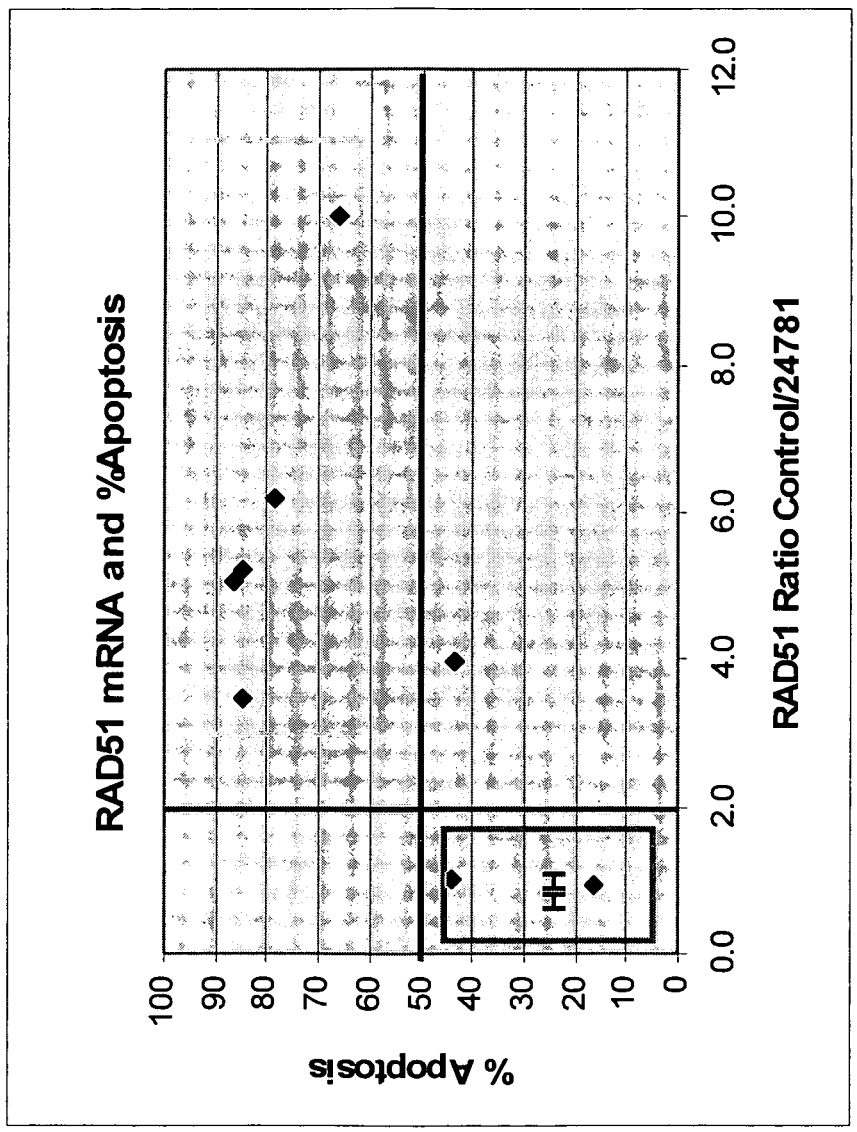
FIG. 8D shows a correlation plot of mRNA expression levels with % Apoptosis; the most sensitive and resistant lines are indicated by the boxes.
Figure 9:
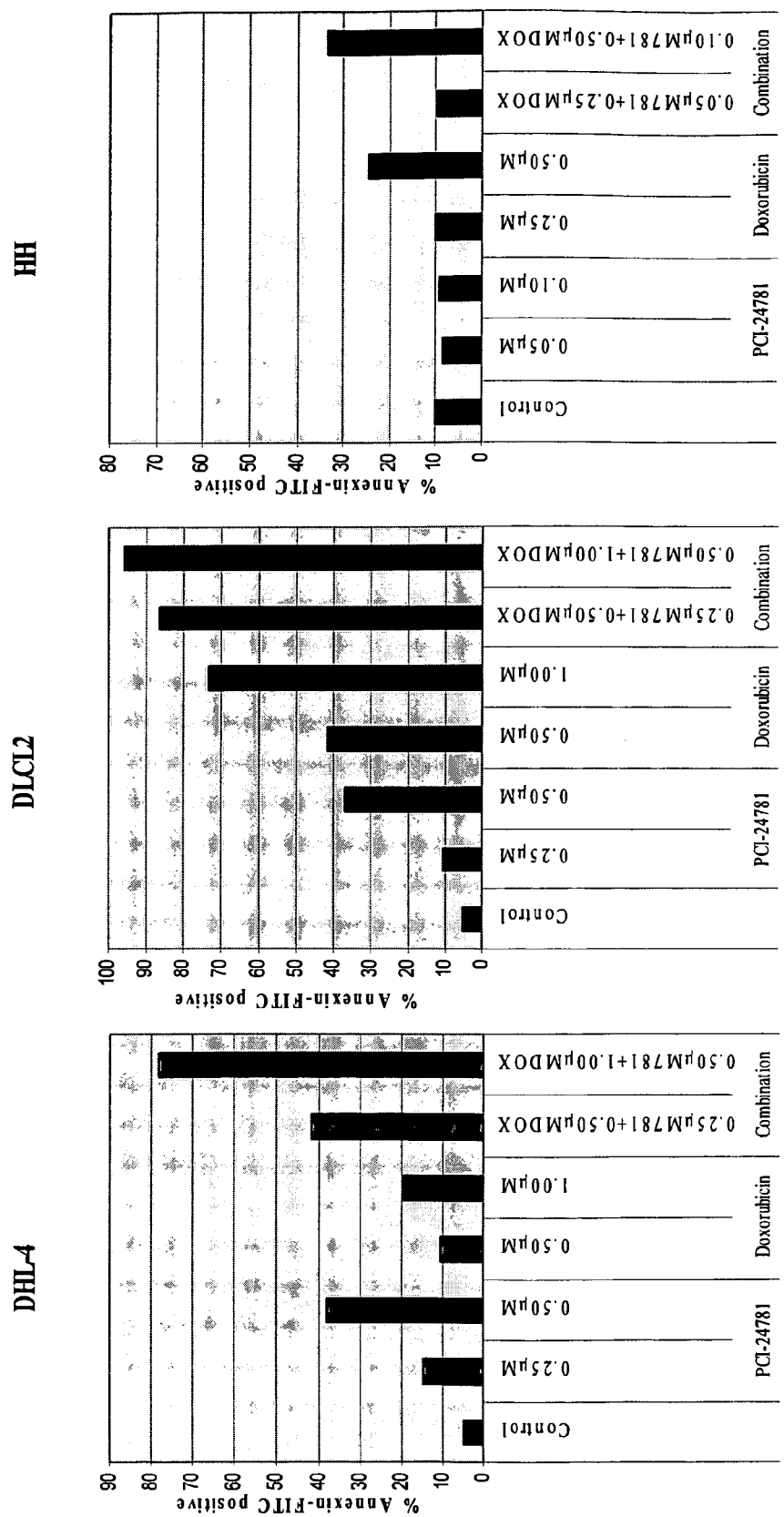
FIG. 9 shows the effects of a combination of 3-((dimethylamino)methyl)-N-(2-(4-(hydroxycarbamoyl)phenoxy)ethyl)benzofuran-2-carboxamide and doxorubicin administered simultaneously in Non-Hodgkins cell lines DHL-4 and DLCL2 and HH.

Correlation of 3-((dimethylamino)methyl)-N-(2-(4-(hydroxycarbamoyl)phenoxy)ethyl)benzofuran-2-carboxamide induced downregulation of RAD51 with % apoptosis was measured by different methods. FIG. 8A shows baseline RAD51 expression levels by Western Blot. RAD51 protein decrease was measured in cells treated with 3-((dimethylamino)methyl)-N-(2-(4-(hydroxycarbamoyl)phenoxy)ethyl)benzofuran-2-carboxamide (see FIG. 8B). It was determined that RAD51 protein and mRNA decreases after treatment with 3-((dimethylamino)methyl)-N-(2-(4-(hydroxycarbamoyl)phenoxy)ethyl)benzofuran-2-carboxamide correlated with % apoptosis (see FIG. 8C). Additionally, a correlation of mRNA expression with % apoptosis was found as shown in the correlation plot of FIG. 8D.

Example 18

Treatment of an HDAC Inhibitor and Doxorubicin

Combinations of 3-((dimethylamino)methyl)-N-(2-(4-(hydroxycarbamoyl)phenoxy)ethyl)benzofuran-2-carboxamide and doxorubicin administered simultaneously showed synergistic effects in Non-Hodgkins cell lines, DHL-4 and DLCL2, but were less than additive in the HH cell line, in which RAD51 levels were low and not decreased by 3-((dimethylamino)methyl)-N-(2-(4-(hydroxycarbamoyl)phenoxy)ethyl)benzofuran-2-carboxamide.

Throughout the specification, claims and accompanying figures, a number of embodiments have been described. Nevertheless, in some embodiments, it is understood that various modifications are made without departing from the spirit and scope of the description. Accordingly, other embodiments are within the scope of the following claims.

What is claimed is:

1. A method of inhibiting or relieving a cancer associated with a defect in non-homologous end joining of DNA in an individual in need thereof, comprising: (a) identifying the cancer as containing a defect in non-homologous end joining of DNA, wherein the defect comprises a defect in a gene selected from the group consisting of: Ku70, Ku80, Ku86, Ku, PRKDC, LIG4, XRCC4, DCLRE1C, and XLF; and (b) administering to the individual: (i) a therapeutically effective amount of 3-((dimethylamino)methyl)-N-(2-(4-(hydroxycarbamoyl)phenoxy)ethyl)benzofuran-2-carboxamide, or a pharmaceutically acceptable salt thereof; and (ii) a treatment capable of damaging cellular DNA.

2. The method of claim 1, wherein the cancer is selected from a breast cancer, colon cancer, colorectal carcinomas, non-small cell lung cancer, small-cell lung cancer, liver cancer, ovarian cancer, prostate cancer, uterine cervix cancer, urinary bladder cancer, gastric carcinomas, gastrointestinal stromal tumors, pancreas cancer, germ cell tumors, mast cell tumors, neuroblastoma, mastocytosis, testicular cancers, glioblastomas, astrocytomas, lymphomas, melanoma, myelomas, acute myelocytic leukemia (AML), acute lymphocytic leukemia (ALL), myelodysplastic syndrome, chronic myelogenous leukemia, Burkitt's lymphoma, chronic myelogenous leukemia, and B-cell lymphoma.

3. The method of claim 1, wherein the therapeutically effective amount of 3-((dimethylamino)methyl)-N-(2-(4-(hydroxycarbamoyl)phenoxy)ethyl)benzofuran-2-carboxamide is from about 0.2 mg to about 2000 mg.

4. The method of claim 1, wherein the treatment capable of damaging cellular DNA is selected from: radiotherapy, an anticancer agent, or any combination thereof.

5. The method of claim 1, wherein the treatment capable of damaging cellular DNA is radiotherapy.

6. The method of claim 1, wherein the treatment capable of damaging cellular DNA is selected from: a cytotoxic/cytostatic agent, an antiproliferative agent, a prenyl-protein transferase inhibitor, an HMG-CoA reductase inhibitor, a nitrogen mustard, a nitroso urea, an angiogenesis inhibitor, an inhibitor of a cell proliferation and survival signaling pathway, an apoptosis inducing agent, an agents that interferes with a cell cycle checkpoints, a biphosphate, or any combination thereof.

7. A method of inhibiting or relieving a cancer in which RAD51 is overexpressed in an individual in need thereof, comprising: (a) identifying the cancer as overexpressing RAD51; and (b) administering to the individual: (i) a therapeutically effective amount of 3-((dimethylamino)methyl)-N-(2-(4-(hydroxycarbamoyl)phenoxy)ethyl)benzofuran-2-carboxamide, or a pharmaceutically acceptable salt thereof; and (ii) a treatment capable of damaging cellular DNA.

* * * * *